(12) United States Patent
Klagsbrun et al.

(10) Patent No.: US 7,273,612 B2
(45) Date of Patent: Sep. 25, 2007

(54) SOLUBLE INHIBITORS OF VASCULAR ENDOTHELIAL GROWTH FACTOR AND USE THEREOF

(75) Inventors: Michael Klagsbrun, Newton, MA (US); Shay Soker, Brookline, MA (US); Michael L. Gagnon, Brighton, MA (US)

(73) Assignee: Children's Medical Center Corporation, Boston, MA (US)

( * ) Notice: Subject to any disclaimer, the term of this patent is extended or adjusted under 35 U.S.C. 154(b) by 0 days.

(21) Appl. No.: 10/104,610

(22) Filed: Mar. 22, 2002

(65) Prior Publication Data

US 2003/0104532 A1    Jun. 5, 2003

Related U.S. Application Data

(63) Continuation of application No. 09/580,989, filed on May 30, 2000, now abandoned, which is a continuation of application No. PCT/US98/26138, filed on Dec. 9, 1998.

(60) Provisional application No. 60/099,615, filed on Sep. 9, 1998, provisional application No. 60/069,687, filed on Dec. 12, 1997, provisional application No. 60/069,155, filed on Dec. 9, 1997.

(51) Int. Cl.
*A61K 39/00* (2006.01)
*A61K 38/17* (2006.01)

(52) U.S. Cl. .............................. 424/184.1; 424/185.1

(58) Field of Classification Search ............. 424/184.1, 424/185.1

See application file for complete search history.

(56) References Cited

U.S. PATENT DOCUMENTS 6,204,011 B1    3/2001    Kendall et al.

FOREIGN PATENT DOCUMENTS

WO    WO94/11499 A    5/1994
WO    WO95/33050 A    12/1995
WO    WO96/40769 A    12/1996

OTHER PUBLICATIONS

Yamada et al, Blood 97(6): 1671-8, 2001.*
Bodey et al, Anticancer Research 20: 2665-2676, 2000.*
Ezzell et al, Journal of NIH Research 7: 46-49, 1995.*
Spitler et al, Cancer Biotherapy 10: 1-3, 1995.*
Soker et al, J Biol Chem 272(50): 31582-88, Dec. 12, 1997.*
Dermer et al, Bio/Technology 12: 320, 1994.*
Gura et al, Science 278: 1041-1042, Nov. 1997.*
T. Omura et al., "Identification of a 190 kDa Vascular Endothelial Growth Factor 165 Cell Surface Binding Protein on a Human Glioma Cell Line," J. Biol. Chem., 272(37):23317-23322, 1997.
S. Soker et al., "Neuropilin-1 is expressed by endothelial and Tumor Cells as an Isoform-Specific Receptor for Vascular Endothelial Growth Factor," Cell, 92:735-745, 1998.
S. Soker et al., "Characterization of Novel Vascular Endothelial Growth factor (VEGF) Receptors on Tumor Cells that Bind VEGF165 Via it Exon 7-Encoded Domain," J. Biol. Chem., 271(10): 5761-5767, 1996.
H. Chen et al., "Neuropilin-2, A Novel Member of the Neuropilin Family, is a High Affinity receptor for the Semaphorins sema E and sema IV but not sema III," Neuron, 19:547-559, 1997.
A. L. Kolodkin et al., "Neuropilin is a Semaphorin III Receptor," Cell, 90:753-762, 1997.
Ngo et al., 1994, The Protein Folding Problem and Tertiary Structure Prediction, pp. 492-495.

* cited by examiner

*Primary Examiner*—Christina Chan
*Assistant Examiner*—Phuong Huynh
(74) *Attorney, Agent, or Firm*—Nixon Peabody LLP

(57) ABSTRACT

The present invention relates to cDNA encoding a soluble neuropilin protein (sNP) which is isolated from neuropilin (NP) producing cells or is recombinantly engineered from NP-encoding DNA. NP-1 and NP-2 are preferred NPs but any neuropilin or VEGF receptor (VEGFR), where the constituents share at least about 85% homology with either of the above $VEGF_{165}R$/NP-1 and NP-2. More preferably, such constituent shares at least 90% homology. Still more preferably, each constituent shares at least 95% homology.

2 Claims, 30 Drawing Sheets

| | | |
|---|---|---|
| 1 | MERGLPLLCAVLALVLAPAGAFRNDKCGDTIKIESPGYLTSPGYPHSYHPSEKCEWLIQAPDPYQRIMIN | 70 |
| 71 | FNPHFDLEDRDCKYDVEVFDGENENGHFRGKFCGKIAPPPVVSSGPLFIKFVSDYETHGAGFSIRYEI | 140 |
| 141 | FKRGPECSQNYTTPSGVIKSPGFPEKYPNSLECTYIVFAPKMSEIILEFESFDLEPDSNPPGGMFCRYDR | 210 |
| 211 | LEIWDGFPDVGPHIGRYCGQKTPGRIRSSSGILSMVFYTDSAIAKEGFSANYSVLQSSVSEDFKCMEALG | 280 |
| 281 | MESGEIHSDQITASSQYSTNWSAERSRLNYPENGWTPGEDSYREWIQVDLGLLRFVTAVGTQGAISKETK | 350 |
| 351 | KKYYVKTYKIDVSSNGEDWITIKEGNKPVLFQGNTNPTDVVVAVFPKPLITRFVRIKPATWETGISMRFE | 420 |
| 421 | VYGCKITDYPCSGMLGMVSGLISDSQITSSNQGDRNWMPENIRLVTSRSGWALPPAPHSYINEWLQIDLG | 490 |
| 491 | EEKIVRGIIQGGKHRENKVFMRKFKIGYSNNGSDWKMIMDDSKRKAKSFEGNNYDTPELRTFPALSTR | 560 |
| 561 | FIRIYPERATHGGLGLRMELLGCEVEAPTAGPTTPNGNLVDECDDDQANCHSGTGDDFQLTGGTTVLATE | 630 |
| 631 | KPTVIDSTIQSEFPTYGFNCEFGWGSHKTFCHWEHDNHVQLKWSVLTSKTGPIQDHTGDGNFIYSQADEN | 700 |
| 701 | QKGKVARLVSPVVYSQNSAHCMTFWYHMSGSHVGTLRVKLRYQKPEEYDQLVWMAIGHQGDHWKEGRVLL | 770 |
| 771 | HKSLKLYQVIFEGEIGKGNLGGIAVDDISINNHISQEDCAKPADLDKKNPEIKIDETGSTPGYEGEGEGD | 840 |
| 841 | KNISRKPGNVLKTLDPILITIIAMSALGVLLGAVCGVVLYCACWHNGMSERNLSALENYNFELVDGVKLK | 910 |
| 911 | KDKLNTQSTYSEA 923 | |

COMPARATIVE DEDUCED AMINO ACID SEQUENCES
OF HUMAN VEGF$_{165}$R/NP AND VEGF$_{165}$R/NP-1

```
VEGF165R/NP-2    1  MDMF-PLITW-VFLALYFSRHQVRGQPOPPCGG-RLNSK--DA------GY      50
VEGF165R/NP-1       MERGLPLLCAV-LAL------VLA-PA---GAFR-NDKCGDTIKIESPGY

NP-2            51  ITSPGYPQDY-PSHQNCEW-IVYAPEPNQKIVLNFNPEFEIEKHDCKYDF     100
NP-1                LTSPGYPHSYHPSEK-CEWLIQ-APDPYQRIMINFNPHFDLEDRDCXYDY

NP-2           101  IEIRDGDSESADLLGKHCGNIAPPTIISSGSMLYIKFTSDYARQGAGFSL    150
NP-1                VEVFDGENENGHFRGKFCGKIAPPPVVSSGPFLFIKFVSDYETHGAGFSI

NP-2           151  RYEIFKTGSEDCSKNFTSPNGTIESPGFPEKYPHN-LDCTFTIL-AKPKM    200
NP-1                RYEIFKRGPE-CSQNYTTPSGVIKSPGFPEKYP-NSLECTY-IVFA-PKM

NP-2           201  -EIILQFLIFDLEHD---PLQVGEGD-CKYDWLDIWDGIPHVGPLIGKYCG   250
NP-1                SEIILEFESFDLEPDSNPP---G-GMFCRYDRLEIWDGFPDVGPHIGRYCG

NP-2           251  TKTPSELRSSTGILSLTFHTDMAVAKDGFSARYYLVHQEPL-ENFQCNVP    300
NP-1                QKTPGRIRSSGILSMVPYTDSAIAKEGFSANYS-VLQSSVSEDFKCMEA

NP-2           301  LGMESGAIANEQISASSTYSDGRWTPQQSRLHGDDNGWTPNLDSNKEYLQ    350
NP-1                LGMESGEIHSDQITASSQYSTN-WSAERSRLNYPENGWTPGEDSYREWIQ

NP-2           351  VDL---RFLTMLTAIATQGAISRETQNGYYVKSYKLEVSTNGEDWMVYRH    400
NP-1                VDLGLURFVT---AVGTQGAISKETKKKYYVKTYKIDVSSNGEDWITIKE

NP-2           401  GKNHK-V-FQAN-NDATEVVLN---KLHAPLLTRFVRIRPQTWHSGIALR    450
NP-1                G-N-KPVLFQGNTNP-TDVVVAVFPK---PLITRFVRIKPATWETGISMR

NP-2           451  LELFGCRVTDAPCSMKLGMLSGLIADSQISASSTQEYL-WSPSAARLVSS    500
NP-1                FEVYGCKITDYPCSGMLGMVSGLISDSQIT-SSNQGDRNWMPENIRLVTS
```

FIG. 4A

```
NP-2 501  RSGWF-PRIPQAQPGE---EWLQVDLGTPKTVKGVIIQGARGGDSITAVE 550
NP-1      RSGWALP--P-A-PHSYINEWLQIDLGEEKIVRGIIIQG--GKHRENKV-

NP-2 551  ARAFVRKFKVSYSLNGKDWEYIQDP--RTQQPKLFEGNMHYDTPDIRRFD 600
NP-1      ---FMRKFKIGYSNNGSDWKMIMDDSKRKA--KSFEGNNNYDTPELRTF-

NP-2 601  PIPAQYVRV---YPERWSPA--GI-GMRLEVLGCDWTDSKPTVE--TLGP 650
NP-1      P--ALSTRFIRIYPER---AFHGGLGLRMELLGCE-------VEAPTAGP

NP-2 651  TVKSEETTTPYPTEEEATECGE---NC-SFE-DDKDLQ-----L----P- 700
NP-1      T-----T--PNGNLVD--ECDDDQANCHSGTGDDFQLTGGTTVLATEKPT

NP-2 701  ---S---------GFNCNFD------FLEEPCGWMYD-BA--KW--LRTT 750
NP-1      VIDSTIQSEFPTYGFNCEFGWGSHKTF----CHWEHDNHVQLKNSVL-T-

NP-2 751  WASSSSPN-DRTFPDDRNFLRLQSDS-QREGQYARLISPPVHLPRSPVCM 800
NP-1      --SKTGPIQDHTG-DG-NFIYSQADENQK-GKVARLVSPVVYSQNSAHCM

NP-2 801  EFQYQATG---G--RGVAL--QVVREASQESKLLWV-IREDQGGEWKHGR 850
NP-1      TFWYHMSGSHVGTLR-VKLRYQKPEEYDQ---LVWMAIGH-QGDHWKEGR

NP-2 851  IILP-SYDMEYQ-IVFEGVIGKGRSGEIAIDOIRI----STDVPLENCME 900
NP-1      VLLHKSLKL-YQVI-FEGEIGKGNLGGIAVDDISINNHISQ----EDCAK

NP-2 901  PISAFAGENFKVDIPEIHERE-G----YEDEIDDEYEVDWSNSSSATSGS 950
NP-1      P--ADLDK--KN--PEIKIDETGSTPGYEGEG--EG--DK-NISRKP-GN

NP-2 951  GAPSTDKEKSWLYTLDPILITIIAMSSLGVLLGATCAGLLLYCTCSYSGL 1000
NP-1      VL----K------TLDPILITIIAMSALGVLLGAVC-GVVLYCACWHNGM

NP-2 1001  SSR--SCTTLENYNFELYDG--LKHKVKMNHQKCCSEA 1038
NP-1       SERNLSA--LENYNFELVDGVKLK-KDKLNTQSTYSEA
```

HUMN NEUROPILIN-2 AMINO ACID SEQUENCE:

MDMFPLTWVFLALYFSRHQVRGQPDPPCGGRLNSKDAGYITSPGYPQDYPSHQN
CEWIVYAPEPNQKIVLNFNPHFEIEKHDCKYDFIEIRDGDSESADLLGKHCGNIAPP
TIISSGSMLYIKFTSDYARQGAGFSLRYEIFKTGSEDCSKNFTSPNGTIESPGFPEK
YPHNLDCTFTILAKPKMEIILQFLIFDLEHDPLQVGEGDCKYDWLDIWDGIPHVGPL
IGKYCGTKTPSELRSSTGILSLTFHTDMAVAKDGFSARYYLVHQEPLENFQCNVP
LGMESGRIANEQISASSTYSDGRWTPQQSRLHGDDNGWTPNLDSNKEYLQVDLR
FLTMLTAIATQGAISRETQNGYYVKSYKLEVSTNGEDWMVYRHGKNHKVFQANN
DATEVVLNKLHAPLLTRFVRIRPQTWHSGIALRLELFGCRVTDAPCSNMLGMLS
GLIADSQISASSTQEYLWSPSAARLVSSRSGWFPRIPQAQPGEEWLQVDLGTPK
TVKGVIIGGARGGDSITAVEARAFVRKFKVSYSLNGKDWEYIQDPRTQQPKLFEG
NMHYDTPDIRRFDPIPAQYVRVYPERWSPAGIGMRLEVLGCDWTDSKPTVETLG
PTVKSEETTTPYPTEEEATECGENCSFEDDKDLQLPSGFNCNFDFLEEPCGWMYD
HAKWLRTTWASSSSPNDRTFPDDRNFLRLQSDSQREGQYARLISPPVHLPRSPV
CMEFQYQATGGRGVALQVVREASQESKLLWVIREDQGGEWKHGRIILPSYDMEYQ
IVFEGVIGKGRSGEIAIDDIRISTDVPLENCMEPISAFAGENFKVDIPEIHEREGYED
EIDDEYEVDWSNSSSATSGSGAPSTDKEKSWLYTLDPILITIIAMSSLGVLLGAT
GAGLLLYCTCSYSGLSSRSCTTLENYNFELYDGLKHKVKMNHQKCCSEA*

FIG. 12

| FIG. 13A |
|---|
| FIG. 13B |
| FIG. 13C |

FIG. 13

```
gaattcggca cgaggggaaa ataaaagaga gaaaaacaca aagatttaaa caagaaacct    60
acgaaccag ctctggaaag agccacttc tccaaaatgg atatgtttcc tctcacctgg   120
gtttcttag ccctctactt ttcaagacac caagtgagag gccaaccaga ccaccgtgc   180
ggagtcgtt tgaattccaa agatgctggc tatatcacct ctcccggtta ccccaggac   240
taccctccc accagaactg cgatggatt gtttacgccc ccgaacccaa ccagaagatt   300
gtcctcaact tcaaccctca ctttgaaatc gagaagcacg actgcaagta tgactttatc   360
gagattcggg atggggacag tgaatccgca gacctcctgg gcaaacactg tgggaacatc   420
gccccgccca ccatcatctc ctcggctcc atgctctaca tcaagttcac ctccgactac   480
gccggcagg gggcaggctt ctctctcgc tacgagatct tcaagacagg ctctgaagat   540
tgctcaaaa acttcacaag cccaacggg accatcgaat ctcctgggtt tcctgagaag   600
tatccacaca actggactg caccttacc atcctgcca aacccaagat ggagatcatc   660
ctgcagttcc tgatctttga cctggagcat gaccctttgc agtggggaga ggggactgc   720
aagtacgatt ggctggacat ctgggatggc attccacatg ttggccccct gattggcaag   780
tactgggga ccaaaacacc ctctgaactt cgttcatga cggggatcct ctccctgacc   840
tttcacacgg acatggcggt ggccaaggat ggcttctctg cgcgttacta cctggtccac   900
caagagccac tagagaactt tcagtgcaat gttcctctgg gcatggagtc tggccggatt   960
gctaatgaac agatcagtgc ctcatctacc tactctgatg ggaggtggac ccctcaacaa  1020
agccggctcc atggtgatga caatggctgg acccccaact tggattccaa caaggagtat  1080
ctccaggtgg acctgcgctt tttaaccatg ctcacggcca tgcaacaca gggagcgatt  1140
tccagggaaa cacagaatgg ctactacgtc aaatcctaca agctgaagt cagcactaat  1200
```

FIG. 13A

```
ggagaggact  ggatggtgta  ccggcatggc  aaaaaccaca  aggtatttca  agccaacaac  1260
gatgcaactg  aggtggttct  gaacaagctc  cacgctccac  tgctgacaag  gtttgttaga  1320
atccgccctc  agacctggca  ctcagtatc   gccctccggc  tggagctctt  cggctgccgg  1380
gtcacagatg  ctccctgctc  caacatgctg  gggatgctct  caggcctcat  tgcagactcc  1440
cagatctccg  cctcttccac  ccaggaatac  ctctggagcc  ccagtgcagc  ccgcctggtc  1500
agcagccgct  cgggctggtt  ccctcgaatc  cctcaggccc  agcccggtga  ggagtggctt  1560
caggtagatc  tgggaacacc  caagacagtg  aaggtgtca   tcatccaggg  agcccgcgga  1620
ggagacagta  tcactgctgt  ggaagccaga  gcatttgtgc  gcaagttcaa  agtctcctac  1680
agcctaaacg  gcaaggactg  ggaatacatt  caggaccccca ggaccccagca  gccaaagctg  1740
ttcgaaggga  acatgcacta  tgacaccect  gacatccgaa  ggtttgaccc  cattccggca  1800
cagtatgtgc  gggtataccc  ggagaggtgg  tcgccggcgg  ggattgggat  gcggctggag  1860
gtgctgggct  gtgactggac  agactccaag  cccacggtag  agacgctggg  accactgtg   1920
aagagcaag   agacaaccac  cccctacccc  accgaagagg  aggccacaga  gtgtggggag  1980
aactgcagct  ttgaggatga  caaagatttg  cagctcccctt cgggattcaa  ttgcaacttc  2040
gatttcctcg  aggagccctg  tggtttggatg tatgaccatg  ccaagtggct  ccgaccacc   2100
tgggccagca  gctccagccc  aaacgaccgg  acgtttccag  atgacaggaa  tttcttgcgg  2160
ctgcagagtg  acagccagag  agagggccag  tatgccggc   tcatcagccc  ccctgtccac  2220
ctgcccccgaa gcccggtgtg  catggagttc  cagtaccagg  ccacggcgg   ccgcggggtg  2280
gcgctgcagg  tggtgcggga  agccagccag  gagagcaagt  tgctgtgggt  catccgtgag  2340
gaccagggcg  gcgagtggaa  gcacgggcgg  atcatcctgc  ccagctacga  catggagtac  2400
```

FIG. 13B

```
cagattgtgt tcgagggagt gatagggaaa ggacgttccg gagagattgc cattgatgac  2460
attcggataa gcactgatgt cccactggag aactgcatgg aacccatctc ggctttgca   2520
ggtgagaatt ttaaagtgga catcccagaa atacatgaga gagaaggata tgaagatgaa  2580
attgatgatg aatacgaggt ggactggagc aattcttctt ctgcaacctc agggtctggc  2640
gcccctcga  ccgacaaaga aaagagctgg ctgtacaccc tggatcccat cctcatcacc  2700
atcatcgcca tgagctcact gggcgtcctc ctgggggcca cctgtgcagg cctcctgctc  2760
tactgcacct gttcctactc gggcctgagc tcccgaagct gcaccacact ggagaactac  2820
aacttcgagc gttccactgg ccttaagcac aaggtcaaga tgaaccacca aaagtgctgc  2880
tccgaggcat tctacgatgg acctgaatcc tatctgacgt ttcattccag caagaggggc  2940
tgggaagat  gacgattgc  acctgaatcc tatctgacgt ttcattccag caagaggggc  2940
tggggaagat tacatttttt tttccttgg  aaactgaatg ccataatctc gatcaaaccg  3000
atccagaata ccgaaggtat ggacaggaca gaaaagcgag tcgcaggagg aagggagatg  3060
cagccgcaca cgggatgatt acctcctag  gctaagtcat tgcaggaacg            3120
gggctgtgtt ctctgctggg acaaaacagg agctcatctc tttggggtca cagttctatt  3180
ttgtttgtga gttgtatta  ttattattat tattattatt atattttatt tctttggtct  3240
gtgagcaact caaagaggca gaagaggaga atgactttc  cagaatagaa gtggagcagt  3300
gatcattatt ctccgctttc tctttctaat caacacttga aaagcaaagt gtctttttcag 3360
cctttccatc tttacaaata.aaactcaaaa aagctgtcca gctt                   3404
```

FIG. 13C

| FIG. 14A |
| FIG. 14B |
| FIG. 14C |
| FIG. 14E |
| FIG. 14F |

FIG. 14

| | | | | | | | | | |
|---|---|---|---|---|---|---|---|---|---|
| ATG | GAG | AGG | GGG | CTG | CCG 256 | CTC | CTC | TGC 265 | GCC | GTG 274 CTC | ATA 283 GTC | CTC | GCC 292 CCG |
| M | E | R | G | L | P | L | L | C | A | V | L | I | L | A | P |
| GCC | GGC | GCT | TTT | CGC | AAC 310 | GAT | AAA | TGT 319 | GGC | GAT 328 ACT | ATA 337 ATT | AAA | GAA | AGC 346 CCC |
| A | G | A | F | R | N | D | K | C | G | D | T | I | I | K | E | S | P |
| GGG | TAC | CTT | ACA | TCT | CCT 364 | GGT | TAT | CAT 373 | CCT | TAT 382 TAT | TCT 391 AGT | CCA | ATA | AGT | AAA | TGC 400 TGC |
| G | Y | L | T | S | P | G | Y | H | P | Y | Y | S | P | I | S | K | C |

```
733        742        751        760        769        778
TTC CCT AAA TAT AAC AGC GAA TGC ACT TAT ATT TTT GTC TTT GCG CCA
 F   P   K   Y   N   S   E   C   T   Y   I   F   V   F   A   P 787        796        805        814        823        832
AAG ATG TCA GAG ATT GGG CTG TTT TTT CCT GAG TCA GAC CCT TCA
 K   M   S   E   I   G   L   F   F   P   E   S   D   P   S 841        850        859        868        877        886
AAT CCT GGG ATG GGG TTC CGC TAC GAC CGG CTA GAA ATC TGG GAT GGA
 N   P   G   M   G   F   R   Y   D   R   L   E   I   W   D   G 895        904        913        922        931        940
TTC GAT CCT GGC GTT CAC CAT ATT GGG CGT TAC TGT GGA CAG AAA TGG GAT
 F   D   P   G   V   H   H   I   G   R   Y   C   G   Q   K   W   D 949        958        967        976        985        994
CGA TCC TCA ATT ATT TCC ATG TCC ATG GTT TAC CAG TAC ACC GAC AGC GCG
 R   S   S   I   I   S   M   S   M   V   Y   Q   Y   T   D   S   A 1003       1012       1021       1030       1039       1048
AAA GAA GGT TTC TCA GCA AAC TAC AGT GTC AGC CAG TTG TCA AGT GTC TCA
 K   E   G   F   S   A   N   Y   S   V   S   Q   L   S   S   V   S 1057       1066       1075       1084       1093       1102
TTC AAA TGT ATG GAA GCT CTG GGC ATG GAA TCA GGA GAG ATT CAT TCT
 F   K   C   M   E   A   L   G   M   E   S   G   E   I   H   S
   (a2→ Cb1)

1111       1120       1129       1138       1147       1156
ATC GCT ACA TCC CAG TAT TAT AGC ACC TGG TCT GCA GAG CGC TCC
 I   A   T   S   Q   Y   Y   S   T   W   S   A   E   R   S 1165       1174       1183       1192       1201       1210
AAC CTG TAC AAT GGG TGG ACT CCC GGA GAT TAC CGA GAG
 N   L   Y   N   G   W   T   P   G   D   Y   S   R   E
```

```
AAA CCA GCA GAC CTG GAT  AAA AAG AAC CCA GAA ATT GAT  AAA ATT GAA ACA GGG
 K   P   A   D   L   D    K   K   N   P   E   I   D    K   I   E   T   G
2677                    2686                    2695                    2704                    2713                    2722

AGC ACG CCA GGA TAC GAA  TAC GGT GAA GGT GAA GAC  AAG AAC ATC TCC AGG AAG
 S   T   P   G   Y   E    Y   G   E   G   E   D    K   N   I   S   R   K
              2731                    2740                    2749                    2758                    2767                    2776

CCA GGC AAT GTG TTG AAG  ACC TTA GAT CCC ATC CTC  ATC ACC ATA GCC ATG
 P   G   N   V   L   K    T   L   D   P   I   I    I   T   I   A   M
              2785                    2794                    2803                    2812      L→TM              2821                    2830

AGT GCC CTG GGG GTC CTC  CTG GGG GCT GTC GTG TGT  TAC CTG TGT GCC
 S   A   L   G   V   L    L   G   A   V   V   C    Y   L   C   A
              2839                    2848                    2857                    2866                    2875                    2884

TGT TGG CAT AAT GGG ATG  TCA GAA AGA AAC TTG TCT  GCC CTG GAG AAC
 C   W   H   N   G   M    S   E   R   N   L   S    A   L   E   N
              2893   C_TM    H→N_cyto              2902                    2911                    2920                    2929                    2938

TTT GAA CTT GTG GAT GGT  GTG AAG TTG AAA GAC  AAA CTG AAT ACA CAG AGT
 F   E   L   V   D   G    V   K   L   K   D    K   L   N   T   Q   S
              2947                    2956                    2965                    2974                    2983                    2997

ACT TAT TCG GAG GCA TGA  3'  (SEQ ID NO: 1)
 T   Y   S   E   A   *        (SEQ ID NO: 2)
              3001       E_cyto              3010
```

SOLUBLE INHIBITORS OF VASCULAR ENDOTHELIAL GROWTH FACTOR AND USE THEREOF

CROSS REFERENCE TO RELATED APPLICATIONS

This application is a continuation of U.S. Ser. No. 09/5 80,989 filed on May 30, 2000 now abandoned, which is a continuation of International Application PCT/US98/26138 filed on Dec. 9, 1998 which designates the U.S. and claims priority benefits of U.S. Provisional Application Ser. Nos. 60/069,155 filed on Dec. 9, 1997, 60/069,687 filed on Dec. 12, 1997 and 60/099,615 filed on Sep. 9, 1998, all of which are incorporated herein by reference.

STATEMENT REGARDING FEDERALLY SPONSORED RESEARCH

The work described herein was supported, in part, by National Institute of Health grants CA37392 and CA45548. The U.S. Government has certain rights to the invention.

FIELD OF THE INVENTION

The present invention relates to vascular endothelial growth factor (VEGF). More particularly, the invention relates to soluble inhibitors of VEGF and use of those inhibitors in the treatment of disorders that are associated with VEGF.

BACKGROUND OF THE INVENTION

Blood vessels are the means by which oxygen and nutrients are supplied to living tissues and waste products are removed from living tissue. Angiogenesis refers to the process by which new blood vessels are formed. See, for example, the review by Folkman and Shing, *J. Biol. Chem.* 267, 10931-10934 (1992), Dvorak, et al., *J. Exp. Med.,* 174, 1275-1278 (1991)). Thus, where appropriate, angiogenesis is a critical biological process. It is essential in reproduction, development and wound repair. However, inappropriate angiogenesis can have severe negative consequences. For example, it is only after many solid tumors are vascularized as a result of angiogenesis that the tumors have a sufficient supply of oxygen and nutrients that permit it to grow rapidly and metastasize. Because maintaining the rate of angiogenesis in its proper equilibrium is so critical to a range of functions, it must be carefully regulated in order to maintain health. The angiogenesis process is believed to begin with the degradation of the basement membrane by proteases secreted from endothelial cells (EC) activated by mitogens such as vascular endothelial growth factor (VEGF) and basic fibroblast growth factor (bFGF). The cells migrate and proliferate, leading to the formation of solid endothelial cell sprouts into the stromal space, then, vascular loops are formed and capillary tubes develop with formation of tight junctions and deposition of new basement membrane.

In adults, the proliferation rate of endothelial cells is typically low compared to other cell types in the body. The turnover time of these cells can exceed one thousand days. Physiological exceptions in which angiogenesis results in rapid proliferation typically occurs under tight regulation, such as found in the female reproduction system and during wound healing.

The rate of angiogenesis involves a change in the local equilibrium between positive and negative regulators of the growth of microvessels. The therapeutic implications of angiogenic growth factors were first described by Folkman and colleagues over two decades ago (Folkman, *N. Engl. J. Med.,* 285:1182-1186 (1971)). Abnormal angiogenesis occurs when the body loses at least some control of angiogenesis, resulting in either excessive or insufficient blood vessel growth. For instance, conditions such as ulcers, strokes, and heart attacks may result from the absence of angiogenesis normally required for natural healing. In contrast, excessive blood vessel proliferation can result in tumor growth, tumor spread, blindness, psoriasis and rheumatoid arthritis.

Thus, there are instances where a greater degree of angiogenesis is desirable—increasing blood circulation, wound healing, and ulcer healing. For example, recent investigations have established the feasibility of using recombinant angiogenic growth factors, such as fibroblast growth factor (FGF) family (Yanagisawa-Miwa, et al., *Science,* 257:1401-1403 (1992) and Baffour, et al., *J Vasc Surg,* 16:181-91 (1992)), endothelial cell growth factor (ECGF) (Pu, et al., *J Surg Res,* 54:575-83 (1993)), and more recently, vascular endothelial growth factor (VEGF) to expedite and/or augment collateral artery development in animal models of myocardial and hindlimb ischemia (Takeshita, et al., *Circulation,* 90:228-234 (1994) and Takeshita, et al., *J Clin Invest.* 93:662-70 (1994)).

Conversely, there are instances, where inhibition of angiogenesis is desirable. For example, many diseases are driven by persistent unregulated angiogenesis, also sometimes referred to as "neovascularization." In arthritis, new capillary blood vessels invade the joint and destroy cartilage. In diabetes, new capillaries invade the vitreous, bleed, and cause blindness. Ocular neovascularization is the most common cause of blindness. Tumor growth and metastasis are angiogenesis-dependent. A tumor must continuously stimulate the growth of new capillary blood vessels for the tumor itself to grow.

There is mounting evidence that VEGF may be a major regulator of angiogenesis (reviewed in Ferrara, et al., *Endocr. Rev.,* 13, 18-32 (1992); Klagsbrun, et al., *Curr. Biol.,* 3, 699-702 (1993); Ferrara, et al., *Biochem. Biophjs. Res. Commun.,* 161, 851-858 (1989)). VEGF was initially purified from the conditioned media of folliculostellate cells (Ferrara, et al., *Biochem. Biophjs. Res. Commun.,* 161, 851-858 (1989)) and from a variety of tumor cell lines (Myoken, et al., *Proc. Natl. Acad. Sci.* USA, 88:5819-5823 (1991); Plouet, et al., *EMBO. J.,* 8:3801-3806 (1991)). VEGF was found to be identical to vascular permeability factor, a regulator of blood vessel permeability that was purified from the conditioned medium of U937 cells at the same time (Keck, et al., *Science,* 246:1309-1312 (1989)). VEGF is a specific mitogen for endothelial cells (EC) in vitro and a potent angiogenic factor in vivo. The expression of VEGF is up-regulated in tissue undergoing vascularization during embryogenesis and the female reproductive cycle (Brier, et al., *Development,* 114:521-532 (1992); Shweiki, et al., *J. Clin. Invest.,* 91:2235-2243 (1993)). High levels of VEGF are expressed in various types of tumors, but not in normal tissue, in response to tumor-induced hypoxia (Shweiki, et al., *Nature* 359:843-846 (1992); Dvorak et al., *J. Exp. Med.,* 174:1275-1278 (1991); Plate, et al., *Cancer Res.,* 53:5822-5827; Ikea, et al., *J. Biol. Chem.,* 270:19761-19766 (1986)). Treatment of tumors with monoclonal antibodies directed against VEGF resulted in a dramatic reduction in tumor mass due to the suppression of tumor angiogeneis (Kim, et al., *Nature,* 382:841-844 (1993)). VEGF appears to play a principle role in many pathological states and processes related to neovascularization. Regulation of VEGF expression in affected tissues could therefore be key in treatment or prevention of VEGF induced neovascularization/angiogenesis.

VEGF exists in a number of different isoforms that are produced by alternative splicing from a single gene containing eight exons (Ferrara, et al., *Endocr. Rev.* 13:18-32 (1992); Tischer, et al., *J. Biol. Chem.*, 806:11947-11954 (1991); Ferrara, et al., *Trends Cardio Med.*, 3:244-250 (1993); Polterak, et al., *J. Biol. Chem.*, 272:7151-7158 (1997)). Human VEGF isoforms consists of monomers of 121, 145, 165, 189, and 206 amino acids, each capable of making an active homodimer (Polterak et al., *J. Biol. Chem*, 272:7151-7158 (1997); Houck, et al., *Mol. Endocrinol.*, 8:1806-1814 (1991)). The $VEGF_{121}$ and $VEGF_{165}$ isoforms are the most abundant. $VEGF_{121}$ is the only VEGF isoforms that does not bind to heparin and is totally secreted into the culture medium. $VEGF_{165}$ is functionally different than $VEGF_{121}$ in that it binds to heparin and cell surface heparin sulfate proteoglycans (HSPGs) and is only partially released into the culture medium (Houck, et al., *J. Biol. Chem.*, 247:28031-28037 (1992); Park, et al., *Mol. Biol. Chem.*, 4:1317-1326 (1993)). The remaining isoforms are entirely associated with cell surface and extracellular matrix HSPGs (Houck, et al., *J. Biol. Chem.*, 247:28031-28037 (1992); Park, et al., *Mol. Biol. Chem.*, 4:1317-1326 (1993)).

VEGF receptor tyrosine kinases, KDR/Flk-1 and/or Flt-1, are mostly expressed by EC (Terman, et al., *Biochem. Biophys. Res. Commun.*, 187:1579-1586 (1992); Shibuya, et al., *Oncogene*, 5:519-524 (1990); De Vries, et al., *Science*, 265:989-991 (1992); Gitay-Goran, et al., *J. Biol. Chem.*, 287:6003-6096 (1992); Jakeman, et al., *J. Clin. Invest.*, 89:244-253 (1992)). It appears that VEGF activities such as mitogenicity, chemotaxis, and induction of morphological changes are mediated by KDR/Flk-1 but not Flt-1, even though both receptors undergo phosphorylation upon binding of VEGF (Millauer, et al., *Cell*, 72:835-846 (1993); Waltenberger, et al., *J. Biol. Chem.*, 269:26988-26995 (1994); Seetharam, et al., *Oncogene*, 10: 135-147 (1995); Yoshida, et al., *Growth Factors*, 7:131-138 (1996)). Recently, Soker et al., identified a new VEGF receptor which is expressed on EC and various tumor-derived cell lines such as breast cancer-derived MDA-MB-231 (231) cells (Soker, et al., *J. Biol. Chem.*, 271:5761-5767 (1996)). This receptor requires the VEGF isoform to contain the portion encoded by exon 7. For example, although both $VEGF_{121}$ and $VEGF_{165}$; bind to KDR/Flk-1 and Flt-1, only $VEGF_{165}$ binds to the new receptor. Thus, this is an isoform-specific receptor and has been named the $VEGF_{165}$ receptor ($VEGF_{165}R$). It will also bind the 189 and 206 isoforms. $VEGF_{165}R$ has a molecular mass of approximately 130 kDa, and it binds $VEGF_{165}$ with a Kd of about $2 \times 10^{-10}$ M, compared with approximately $5 \times 10^{-12}$ M for KDR/Flk-1. In structure-function analysis, it was shown directly that $VEGF_{165}$ binds to $VEGF_{165}R$ via its exon 7-encoded domain which is absent in $VEGF_{121}$ (Soker, et al., *J. Biol. Chem.*, 271:5761-5767 (1996)). However, the function of the receptor was unclear.

The current treatment of angiogenic diseases is inadequate. Agents which prevent continued angiogenesis, e.g, drugs (TNP-470), monoclonal antibodies, antisense nucleic acids and proteins (angiostatin and endostatin) are currently being tested. See, Battegay, *J. Mol. Med.*, 73, 333-346 (1995); Hanahan et al., *Cell*, 86, 353-364 (1996); Folkman, *N. Engl. J. Med.*, 333, 1757-1763 (1995). Although preliminary results with the antiangiogenic proteins are promising, there is still a need for identifying genes encoding ligands and receptors involved in angiogenesis for the development of new antiangiogenic therapies.

SUMMARY OF THE INVENTION

We have isolated a cDNA encoding the $VEGF_{165}$ R gene (SEQ ID NO: 1) and have deduced the amino acid sequence of the receptor (SEQ ID NO:2). We have discovered that this novel VEGF receptor is structurally unrelated to Flt-1 or KDR/Flk-1 and is expressed not only by endothelial cells but by non-endothelial cells, including surprisingly tumor cells.

In ascertaining the function of the $VEGF_{165}R$ we have further discovered that this receptor has been identified as a cell surface mediator of neuronal cell guidance and called neuropilin-1. Kolodkin et al., *Cell* 90:753-762 (1997). We refer to the receptor as VEGF $_{165}$R/NP-1 or NP-1.

In addition to the expression cloning of $VEGF_{165}R$/NP-1 cDNA, we isolated another human cDNA clone whose predicted amino acid sequence was 47% homologous to that of $VEGF_{165}R$/NP-1 and over 90% homologous to rat neuropilin-2 (NP-2) which was recently cloned (Kolodkin, et al., *Cell* 90, 753-762 (1997)).

Our results indicate that these neuropilins are expressed by both endothelial and tumor cells including breast, prostate and melanoma. (FIG. 18) We have shown that endothelial cells expressing both KDR and $VEGF_{165}R$/NP-1 respond with increased chemotaxis towards $VEGF_{165}$, not $VEGF_{121}$, when compared to endothelial cells expressing KDR alone. While not wishing to be bound by theory, we believe that $VEGF_{165}R$/NP-1 functions in endothelial cells to mediate cell motility as a co-receptor for KDR.

We have also shown in the Boyden chamber motility assay that $VEGF_{165}$ stimulates 231 breast carcinoma cell motility in a dose-response manner (FIG. 15A). $VEGF_{121}$, had no effect motility of these cells (FIG. 15B). Since tumor cells such as, 231 cells, do not express the VEGF receptors, KDR or Flt-1, while not wishing to be bound by theory, we believe that tumor cells are directly responsive to $VEGF_{165}$ via $VEGF_{165}R$/NP-1.

We have also analyzed two variants of Dunning rat prostate carcinoma cells, AT2.1 cells, which are of low motility and low metastatic potential, and AT3.1 cells, which are highly motile, and metastatic. Cross-linking and Northern blot analysis show that AT3.1 cells express abundant $VEGF_{165}R$/NP-1, capable of binding $VEGF_{165}$, while AT2.1 cells don't express $VEGF_{165}R$/NP-1 (FIG. 18). Immunostaining of tumor sections confirmed the expression of $VEGF_{165}R$/NP-1 in AT3.1, but not AT2.1 tumors. Additionally, immunostaining showed that in subcutaneous AT3.1 and PC3 tumors, the tumor cells expressing $VEGF_{165}R$/NP-1 were found preferentially at the invading front of the tumor/dermis boundary. Furthermore, stable clones of AT2.1 cells overexpressing $VEGF_{165}R$/NP-1 had enhanced motility in the Boyden chamber assay. These results indicate that neuropilin expression is associated with angiogenesis and motile metastatic cancer cells, and thus is an important target for antiangiogenic and anticancer therapy.

We have now identified and cloned several neuropilin isoforms that are truncated in the C-terminal region to produce soluble neuropilin (sNP) ectodomains (FIG. 19). These isoforms were cloned after a Northern blot analysis revealed that some cell lines and tissues expressed smaller transcripts in addition to 7 kb neuropilin-1 (NP-1) and 7 kb neuropilin-2 (NP-2), that were apparently generated by alternative splicing. Intact neuropilins have a domains homologous to complement components, b domains homologous to coagulation factors, a c domain homologous to MAM, a transmembrane domain and a short 40 amino acid cytoplasmic domain (Kawakami A. et al., (1995) *J. Neurobiol.* 29: 1-17.) (FIG. 19). An isoform of neuropilin-1 was cloned that is C-terminally truncated right after the b domain. During transcription there is reading through a 5' splice donor site so that part of an intron is expressed followed by termination, with the result that the c, transmembrane and cytoplasmic domains are replaced by three intron amino acids following the b domain. In addition, a neuropilin-2 isoform was cloned in which the C-terminal part of the b domain, the c domain, the transmembrane domain and the cytoplasmic domain are replaced by 8 intron amino acids. The truncated neuropilin-1 cDNA was expressed in COS cells and proteins in conditioned medium were analyzed by Western blot using specific anti-neuropilin-1 antibodies (FIG. 20). A 90 kDa protein produced by transfection of the truncated neuropilin-1 cDNA, but not of the vector control was found in conditioned medium but not in the lysate. Thus the neuropilin-1 isoform is a soluble form of neuropilin-1 (sNP 1).

We have also expressed an engineered truncated soluble neuropilin-1 ectodomain receptor that contains the a b and c domains (designated sNP1 abc) by truncation at a site in the juxtamembrane domain.

sNPs are capable of binding to $VEGF_{165}$ or any form of VEGF that contains exon 7 (SEQ ID NO: 15) and therefore are useful for inhibiting VEGF interaction not only with neurophilins but also with KDR Flk-1 and Flt-1 as well. In addition, sNPs could also act as dominant negative receptors when expressed in cells by dimerizing with intact neurophilin receptors. Our results have shown that sNP1 protein preparations are excellent inhibitors of $^{125}I$-$VEGF_{165}$ binding to PAE NP1 and of VEGF-mediated HUVEC proliferation (FIG. 21).

One preferred sNP for use in methods of the invention is an isolated soluble neurophilin-1 comprising amino acids 227 to 587 of SEQ ID NO:2, or a fragment or a homolog thereof, that reduces $VEGF_{165}$ mediated HUVEC proliferation.

Accordingly, sNPs or nucleic acids, e.g., DNA or RNA, encoding sNPs are useful as inhibitors of VEGF and NP function and can be used to treat diseases, disorders or conditions associated with VEGF. sNPs can be used alone or in combination with other anti-VEGF strategies including, for example, those that antagonize VEGF directly (e.g. anti-VEGF antibodies, soluble VEGF receptor extracellular domains), or antagonize VEGF receptors (e.g. anti-KDR antibodies. KDR kinase inhibitors, dominant-negative VEGF receptors) (Presta L G, et al., *Cancer Res.* 57: 4593-4599 (1997), Kendall R L. et al., (1996) *Biochem. Biophys. Res. Commun.* 226: 324-328, Goldman C K, et al., (1998) *Proc. Natl. Acad. Sci. USA* 95: 8795-8800, Strawn L M, et al., (1996) *Cancer Res.* 56: 3540-3545, Zhu Z, et al., (1998). *Cancer Res.* 58: 3209-3214, Witte L, et al., (1998). *Cancer Metastasis Rev.* 17: 155-161.)

Diseases, disorders, or conditions, associated with VEGF, include, but are not limited to retinal neovascularization, hemagiomas, solid tumor growth, leukemia, metastasis, psoriasis, neovascular glaucoma, diabetic retinopathy, rheumatoid arthritis, osteoarthritis, endometriosis, mucular degeneration and retinopathy of prematurity (ROP).

In addition, the present invention relates to methods for screening for expression of naturally occurring soluble neurophilins in selected tissues. Expression can be analyzed at the RNA level (in situ hybridization with specific probes corresponding to intron sequences), or at the protein level (Western blot detection of lower molecular masses). The relative distribution of intact and truncated neurophilin isoforms can then be determined. These techniques can be used to analyze sNP distribution in cells, tissues and biological fluids such as urine. sNP1 and sNP2 both contain C-terminal intron sequences that are absent in intact neurophilins. sNP1 has 3 C-terminal terminal intron amino acids (GIK) and 28 intron bp in the cDNA. sNP-2 has 8 C-terminal intron amino acids (VGCSWRPL, residues 548-555 of SEQ ID NO: 8) and 146 intron bp in the cDNA. Thus, sNP specific probes can be prepared for in situ hybridization and to analyze for sNP distribution in tumors and normal tissue in a background of intact neurophilins.

Other aspects of the invention are disclosed infra.

2A. COS 7 cells were transfected with a primary plasmid pool (#55 of the 231 cell library) representing approximately $3 \times 10^3$ clones and one COS 7 cell binding $^{125}I$-$VEGF_{165}$ in the first round of screening is shown.

2B. Several COS 7 cells transfected with a single positive cDNA clone (A2) binding $^{125}I$-$VEGF_{165}$ after the third round of screening.

FIG. 3. The Deduced Amino Acid Sequence of Human $VEGF_{165}R$/NP-1 (SEQ ID NO:2). The deduced 923 amino acid sequence of the open reading frame of $VEGF_{165}R$/NP-1, clone A2 (full insert size of 6.5 kb) is shown. The putative signal peptide sequence (amino acids 1-21) and the putative transmembrane region (amino acids 860-883) are in boxes. The amino acid sequence obtained by N-terminal amino acid sequencing (FIG. 3, amino acids 22-39) is underlined. The arrow indicates where the signal peptide has been cleaved and removed, based on comparison of the N-terminal sequence of purified $VEGF_{165}R$/NP-1 and the cDNA sequence. The sequence of human $VEGF_{165}R$/NP-1 reported here differs from that reported by He et al. (He and Tessier-Lavigne, *Cell* 90, 739-751 (1997)) in that we find $Lys_{26}$ rather than $Glu_{26}$, and $Asp_{855}$ rather than $Glu_{855}$ $Lys_{26}$ and $Asp_{855}$ are found, however, in mouse and rat $VEGF_{165}R$/NP-1 (Kwakami et al., *J. Neurobiol.* 29, 1-17 (1995); He and Tessier-Lavigne, *Cell* 90, 739-751 1997).

FIGS. 4A and 4B show the comparison of the Deducted Amino Acid Sequence of Human $VEGF_{165}R$/NP-1 (SEQ ID NO:2) and NP-2 (SEQ ID NO:4). The deduced open reading frame amino acid sequences of $VEGF_{165}R$/NP-1 and NP-2 are aligned using the DNASIS program. Amino acids that are identical in both open reading frames are shaded. The overall homology between the two sequences is 43%.

Figure 5:
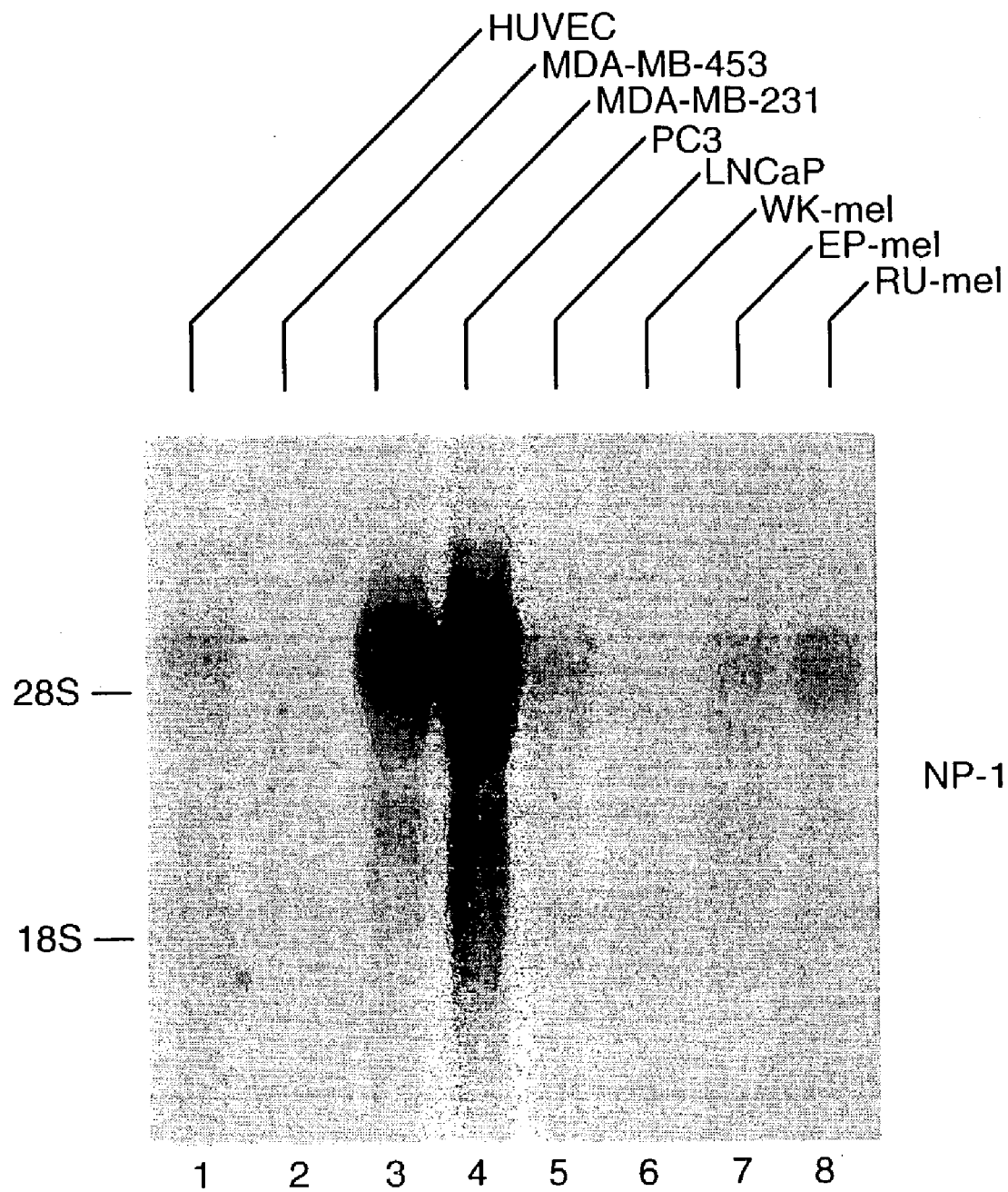

FIG. 5. Northern Blot Analysis of $VEGF_{165}R/NP-1$ Expression in Human EC and Tumor-Derived Cell Lines. Total RNA samples prepared from HUVEC (lane 1) and tumor-derived breast carcinoma, prostate carcinoma and melanoma cell lines as indicated (lanes 2-8) were resolved on a 1% agarose gel and blotted onto a GeneScreen nylon membrane. The membrane was probed with $^{32}P$-labeled $VEGF_{165}R/NP-1$ cDNA and exposed to X-ray film. Equal RNA loading was demonstrated by ethydium bromide staining of the gel prior to blotting. A major species of $VEGF_{165}R/NP-1$ mRNA of approximately 7 kb was detected in several of the cell lines.

Figure 6:
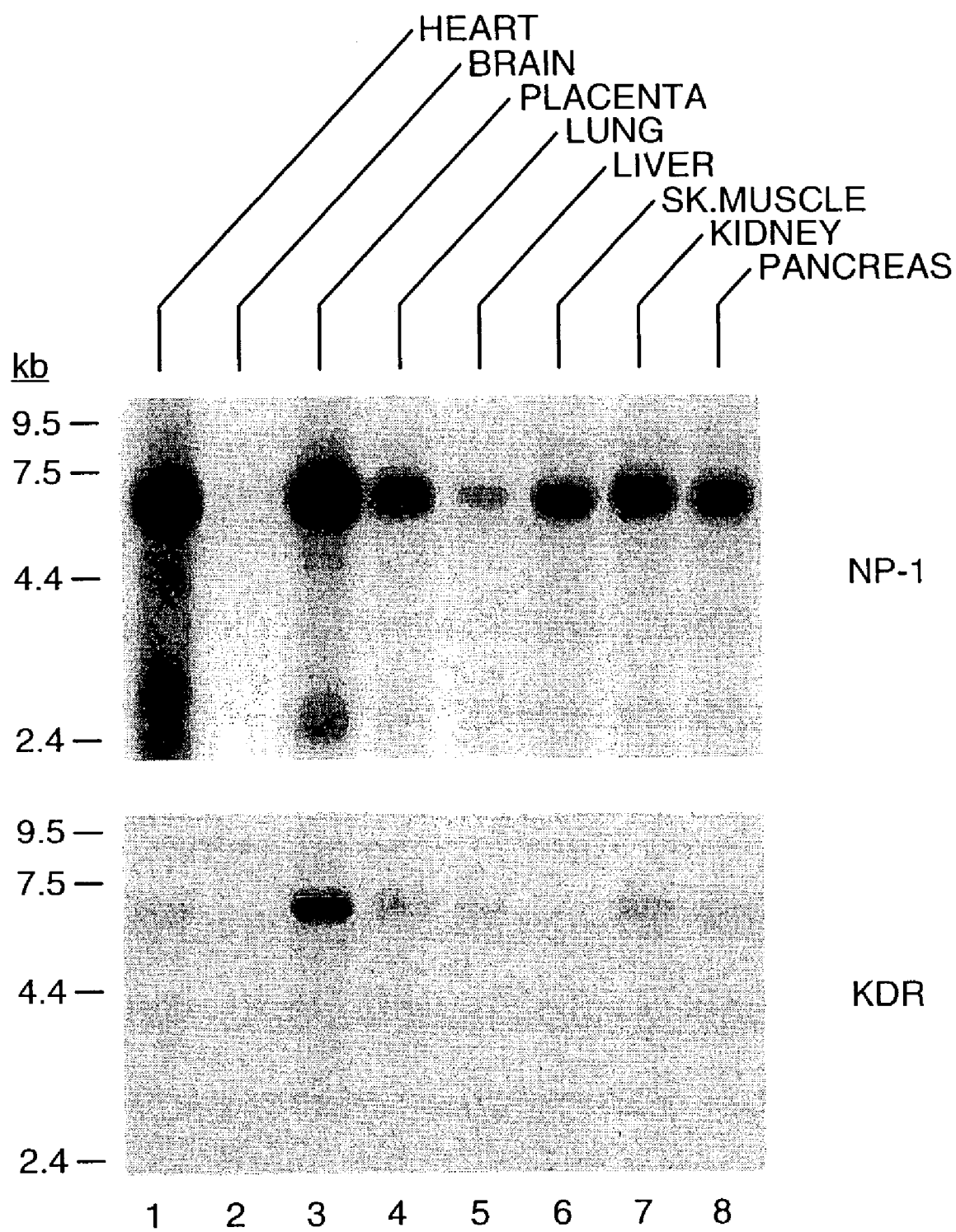

FIG. 6. Northern Blot Analysis of $VEGF_{165}R/NP-1$ and KDR mRNA in Adult Human Tissues. A pre-made Northern blot membrane containing multiple samples of human mRNA (Clonetech) was probed with $^{32}P$-labeled $VEGF_{165}R/NP-1$ cDNA (top) as described in FIG. 5, and then stripped and reprobed with $^{32}P$-labeled KDR cDNA (bottom).

Figure 7A:
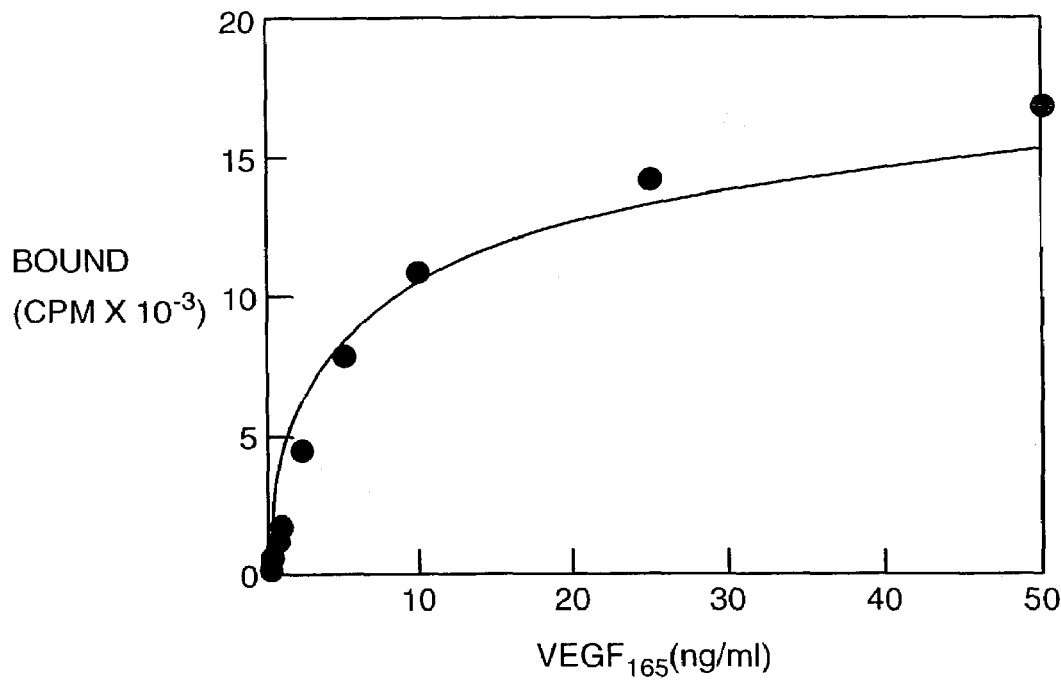
Figure 7B:
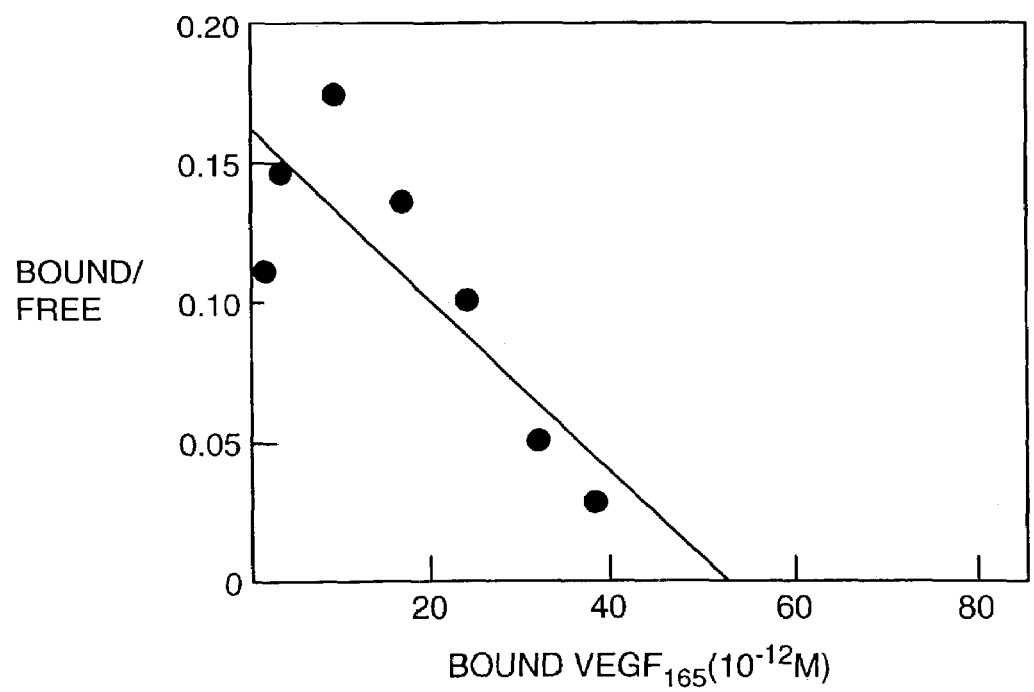

FIGS. 7A and 7B. Scatchard Analysis of $VEGF_{165}$ Binding to $VEGF_{165}R/NP-1$. 7A. Increasing amounts of $^{125}I$-$VEGF_{165}$ (0.1-50 ng/ml) were added to subconfluent cultures of PAE cells transfected with human $VEGF_{165}R/NP-1$ cDNA (PAE/NP-1 cells) in 48 well dishes. Non-specific binding was determined by competition with a 200-fold excess of unlabeled $VEGF_{165}$. After binding, the cells were washed, lysed and the cell-associated radioactivity was determined using a γ counter.

7B. The binding data shown in 7A were analyzed by the method of Scatchard, and a best fit plot was obtained with the LIGAND program (Munson and Rodbard, 1980). PAE/NP-1 cells express approximately $3 \times 10^5$ $VEGF_{165}$ binding sites per cell and bind $^{125}I$-$VEGF_{165}$ with a $K_d$ of $3.2 \times 10^{-10}$ M.

Figure 8:
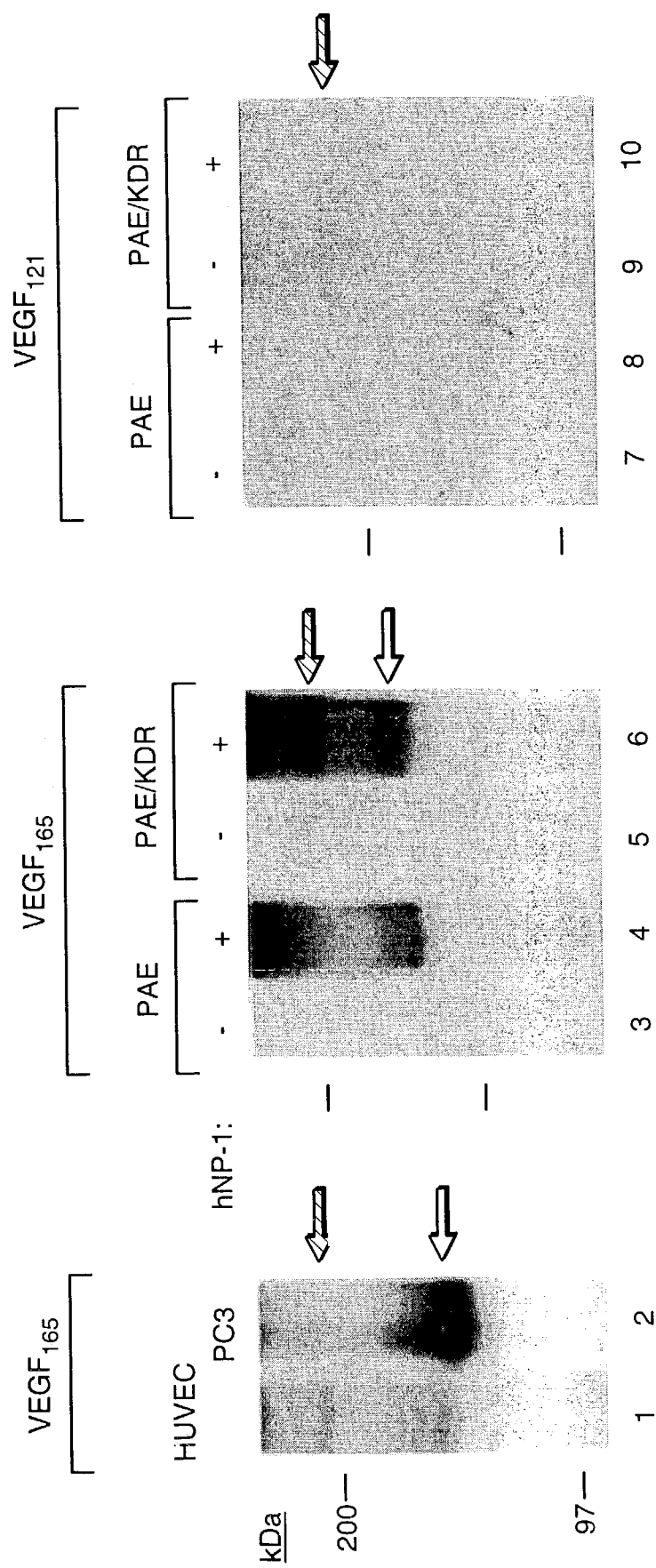

FIG. 8. Cross-linking of $VEGF_{165}$ and $VEGF_{121}$ to PAE cells Expressing $VEGF_{165}R/NP-1$ and/or KDR. $^{125}I$-$VEGF_{165}$ (5 ng/ml) (lanes 1-6) or $^{125}I$-$VEGF_{121}$ (10 ng/ml) (lanes 7-10) were bound to subconfluent cultures of HUVEC (lane 1). PC3 (lane 2), PAE (lanes 3 and 7), a clone of PAE cells transfected with human $VEGF_{165}R/NP-1$ cDNA (PAE/NP-1) (lanes 4 and 8), a clone of PAE cells transfected with KDR (PAE/KDR) (lanes 5 and 9), and a clone of PAE/KDR cells transfected with human $VEGF_{165}R/NP-1$ cDNA (PAE/KDR/NP-1) (lanes 6 and 10). The binding was carried out in the presence of 1 µg/ml heparin. At the end of a 2 hour incubation, each $^{125}I$-VEGF isoform was chemically cross-linked to the cell surface. The cells were lysed and proteins were resolved by 6% SDS-PAGE. The polyacrylamide gel was dried and exposed to X-ray film. Solid arrows denote radiolabeled complexes containing $^{125}I$-VEGF and KDR, open arrows denote radiolabeled complexes containing $^{125}I$-VEGF and $VEGF_{165}R/NP-1$.

Figure 9:
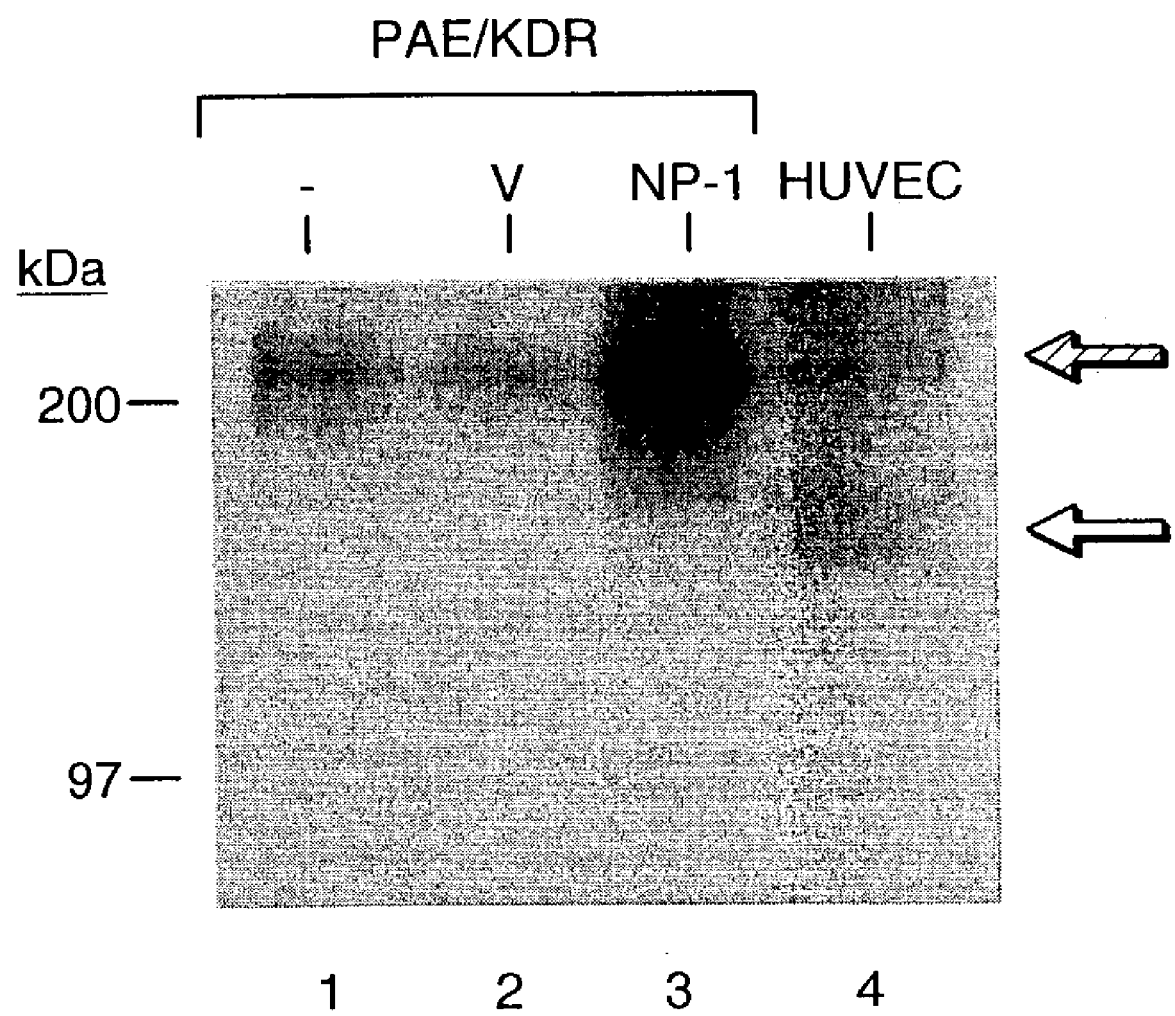

FIG. 9. Cross linking of $VEGF_{165}$ to PAE/KDR Cells Co-expressing $VEGF_{165}R/NP-1$ Transiently. PAE/KDR cells were transfected with pCPhygro or pCPhyg-NP-1 plasmids as described in "Experimental Procedures", and grown for 3 days in 6 cm dishes. $^{125}I$-$VEGF_{165}$ (5 ng/ml) was bound and cross linked to parental PAE/KDR cells (lane 1), to PAE/KDR cells transfected with pCPhygro vector control (V) (lane 2), to PAE/KDR cells transfected with pCPhyg-$VEGF_{165}R/NP-1$ plasmids ($VEGF_{165}R/NP-1$) (lane 3), and to HUVEC (lane 4). The binding was carried out in the presence of 1 µg/ml heparin. The cells were lysed and proteins were resolved by 6% SDS-PAGE as in FIG. 8. Solid arrows denote radiolabeled complexes containing $^{125}I$-$VEGF_{165}$ and KDR. Open arrows denote radiolabeled complexes containing $^{125}I$-$VEGF_{165}$ and $VEGF_{165}R/NP-1$.

Figure 10:
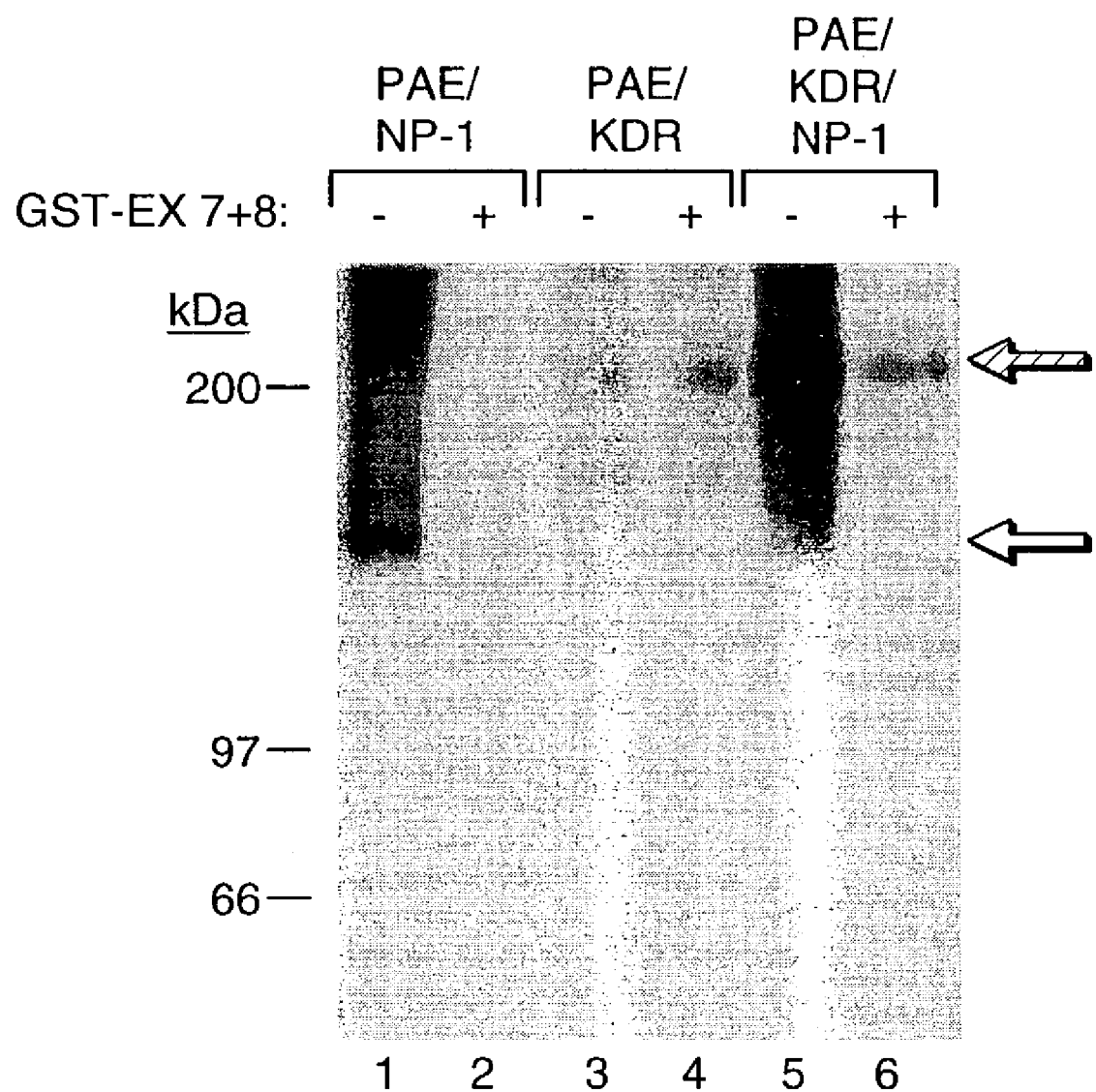

FIG. 10. Inhibition of $^{125}I$-$VEGF_{165}$ Binding to $VEGF_{165}R/NP-1$ Interferes With Its Binding to KDR. $^{125}I$-$VEGF_{165}$ (5 ng/ml) was bound to subconfluent cultures of PAE transfected with human $VEGF_{165}R/NP-1$ cDNA (PAE/NP-1) (lanes 1 and 2), PAE/KDR cells (lanes 3 and 4), and PAE/KDR cells transfected with human $VEGF_{165}R/NP-1$ cDNA (PAE/KDR/NP-1) (lanes 5 and 16) in 35 mm dishes. The binding was carried out in the presence (lanes 2, 4, and 6) or the absence (lanes 1, 3, and 5) of 25 µg/ml GST-Ex 7+8. Heparin (1 µg/ml) was added to each dish. At the end of a 2 hour incubation, $^{125}I$-$VEGF_{165}$ was chemically cross-linked to the cell surface. The cells were lysed and proteins were resolved by 6% SDS-PAGE as in FIG. 9. Solid arrows denote radiolabeled complexes containing $^{125}I$-$VEGF_{165}$ and KDR, open arrows denote radiolabeled complexes containing $^{125}I$-$VEGF_{165}$ and $VEGF_{165}R/NP-1$.

Figure 11C:
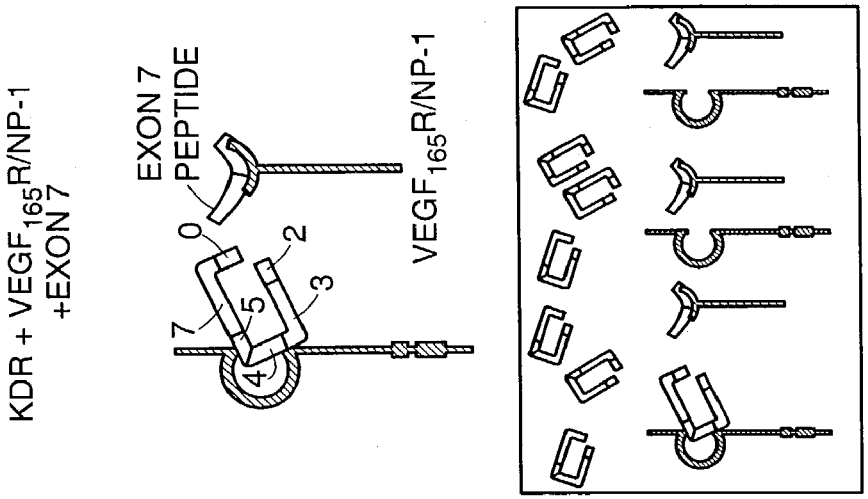
Figure 11B:
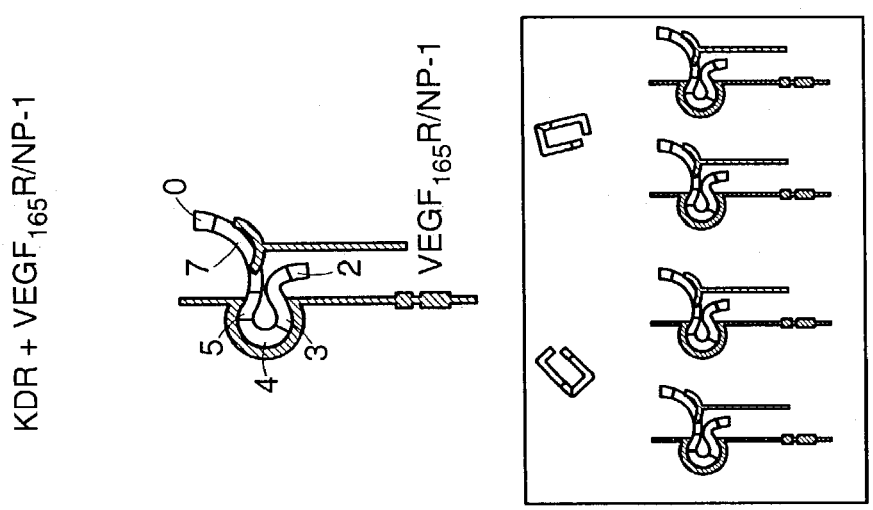
Figure 11A:
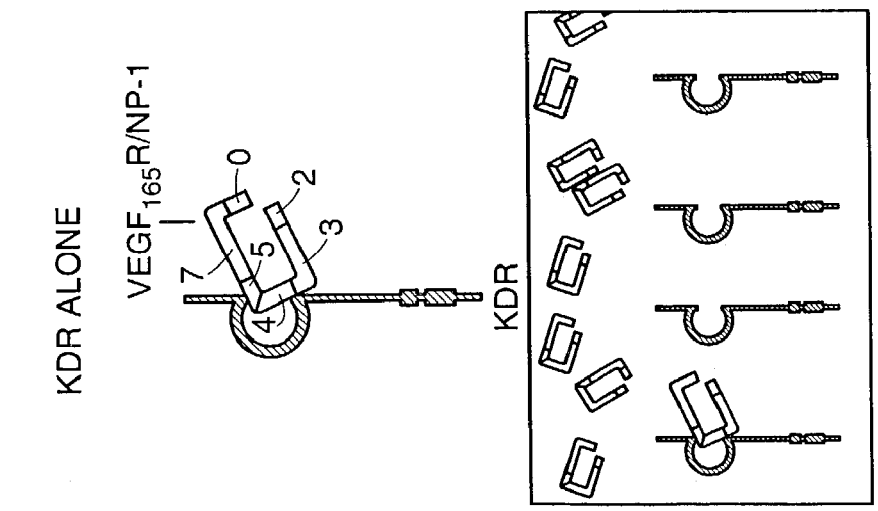

FIGS. 11A-C. A Model for $VEGF_{165}R/NP-1$ Modulation of $VEGF_{165}$ Binding to KDR. 11A.Cells expressing KDR alone. 11B.Cells co-expressing KDR and $VEGF_{165}R/NP-1$. 11C.Cells co-expressing KDR and $VEGF_{165}R/NP-1$ in the presence of GST-Ex 7+8 fusion protein.

A single KDR receptor or a KDR-$VEGF_{165}R/NP-1$ pair is shown in top panels. An expanded view showing several receptors is shown in the bottom panels. $VEGF_{165}$ binds to KDR via exon 4 and to $VEGF_{165}R/NP-1$ via exon 7 (Keyt et al. J. Biol. Chem. 271,5638-5646 (1996b); Soker et al., J. Biol. Chem. 271, 5761-5767 (1996)). A rectangular $VEGF_{165}$ molecule represents a suboptimal conformation that doesn't bind to KDR efficiently while a rounded $VEGF_{165}$ molecule represents one that fits better into a binding site. In cells expressing KDR alone, $VEGF_{165}$ binds to KDR in a suboptimal manner. In cells co-expressing KDR and $VEGF_{165}R/NP-1$, the binding efficiency of $VEGF_{165}$ to KDR is enhanced. It may be that the presence of $VEGF_{165}R/NP-1$ increases the concentration of $VEGF_{165}$ on the cell surface, thereby presenting more growth factor to KDR. Alternatively, $VEGF_{165}R/NP-1$ may induce a change in $VEGF_{165}$ conformation that allows better binding to KDR, or both might occur. In the presence of GST-Ex 7+8, $VEGF_{165}$ binding to $VEGF_{165}R/NP-1$ is competitively inhibited and its binding to KDR reverts to a sub-optimal manner.

FIG. 12. Human NP-2 amino acid sequence (SEQ ID NO:4).

FIGS. 13A, 13B and 13C show human NP-2 nucleotide sequence (SEQ ID NO:3).

Figure 14C:
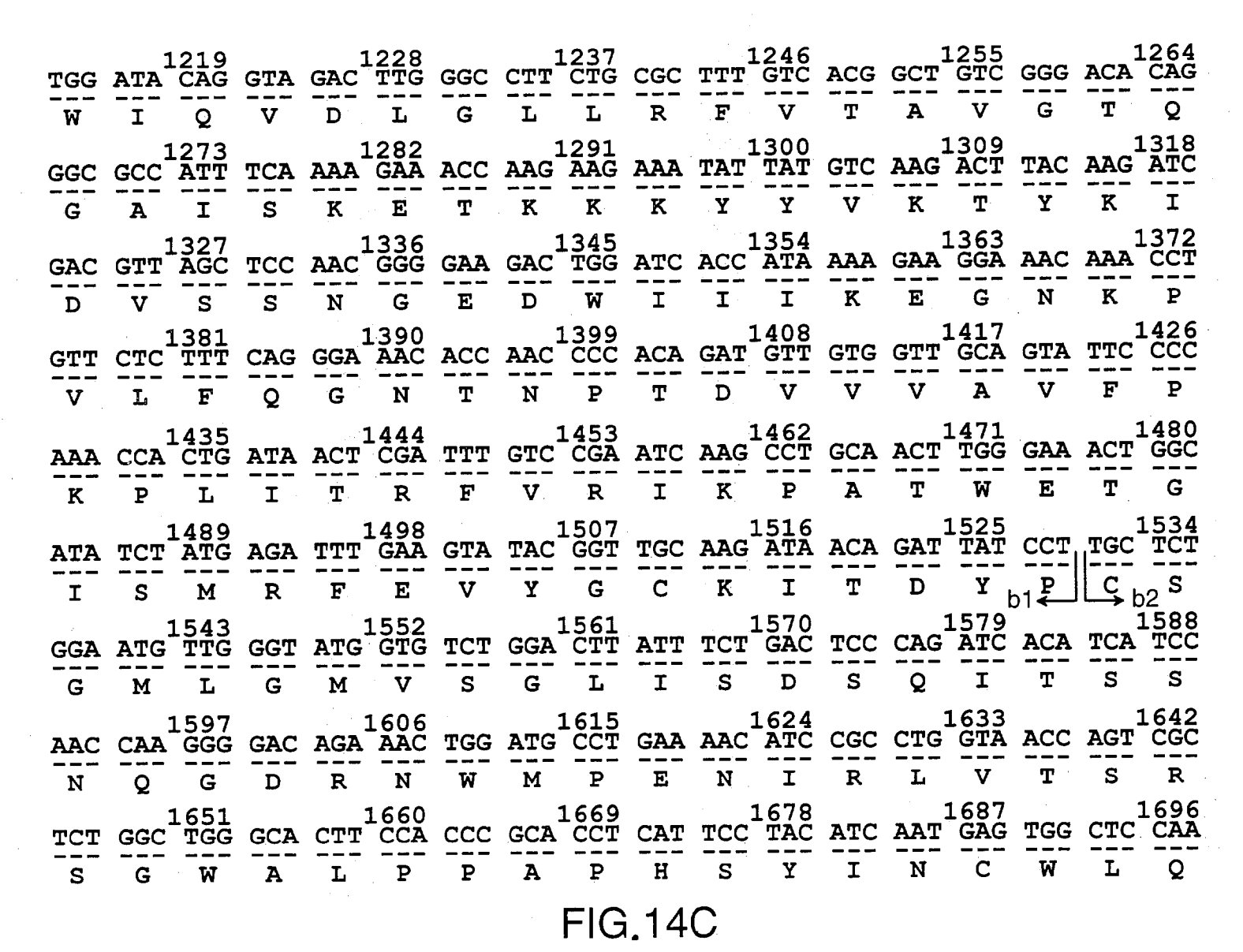
Figure 14D:
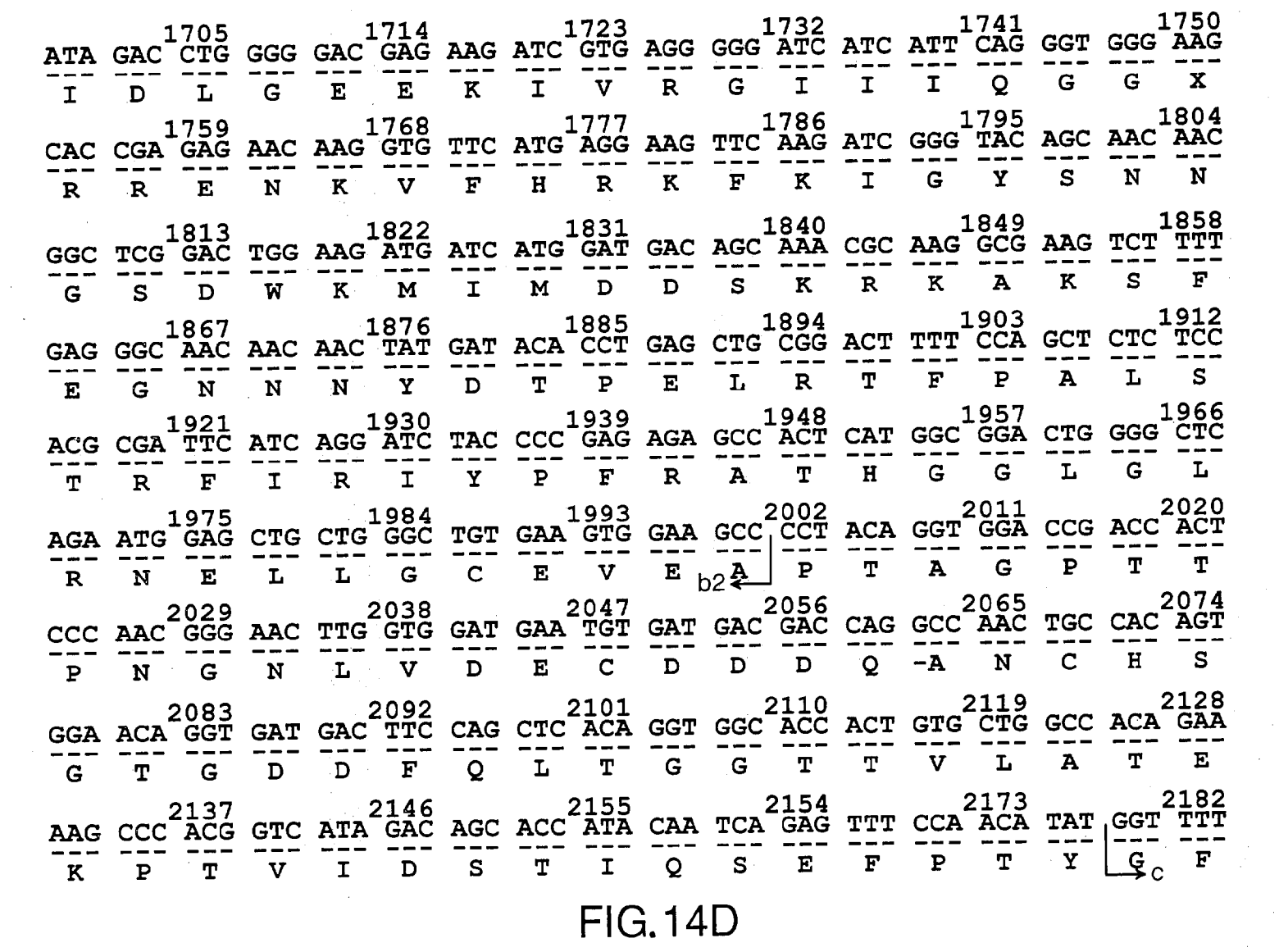
Figure 14E:
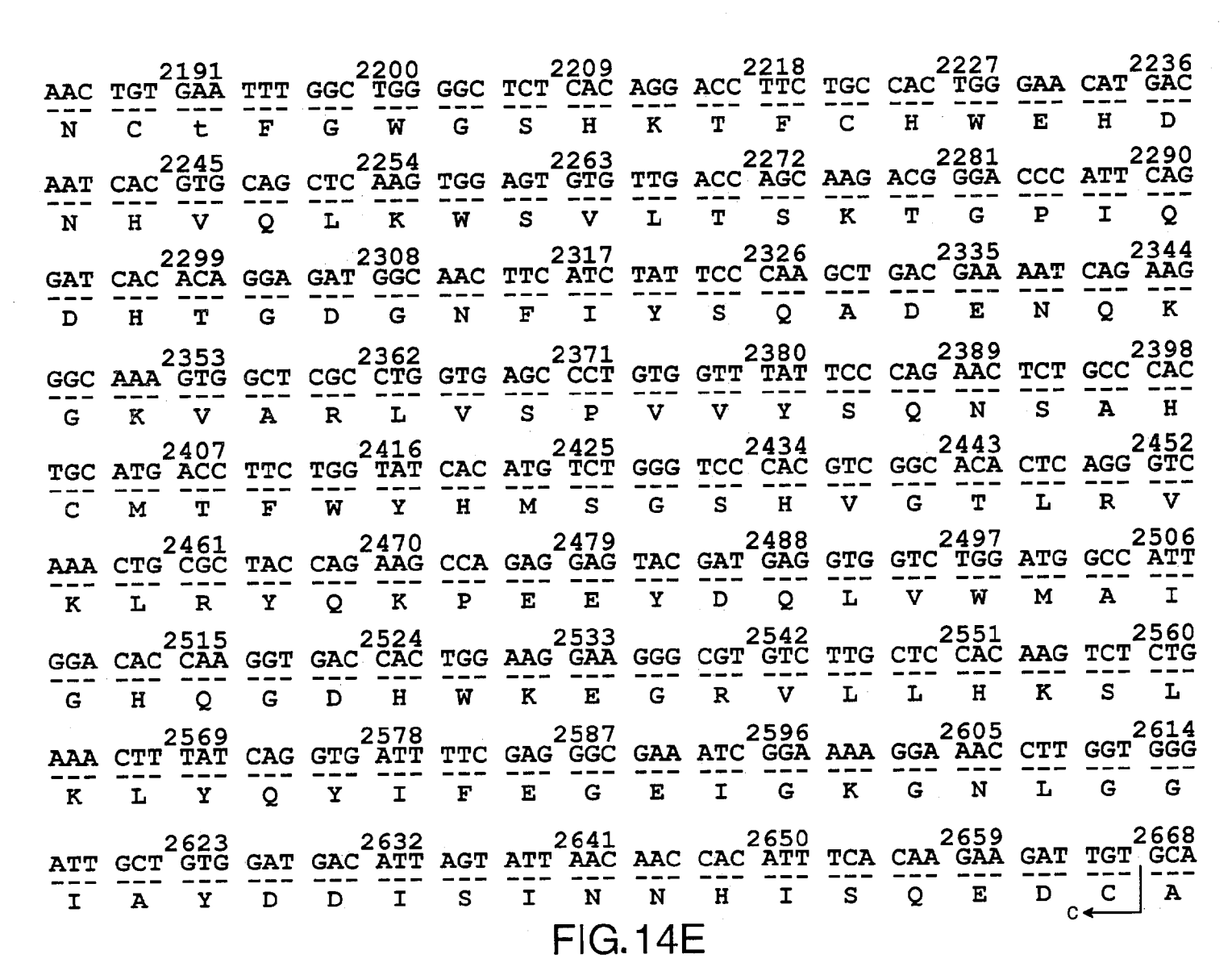

FIGS. 14A-14F show nucleotide SEQ ID NO: 1 and amino acid sequences (SEQ ID NO:2) of $VEGF_{165}R/NP-1$. The domains are indicated.

Figure 15A:
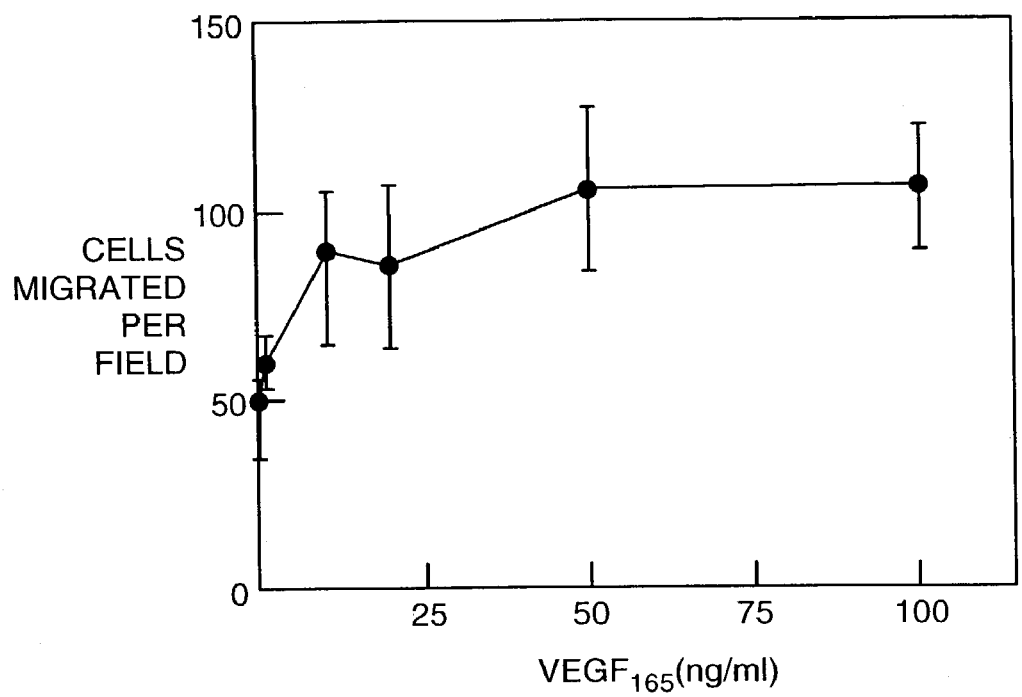
Figure 15B:
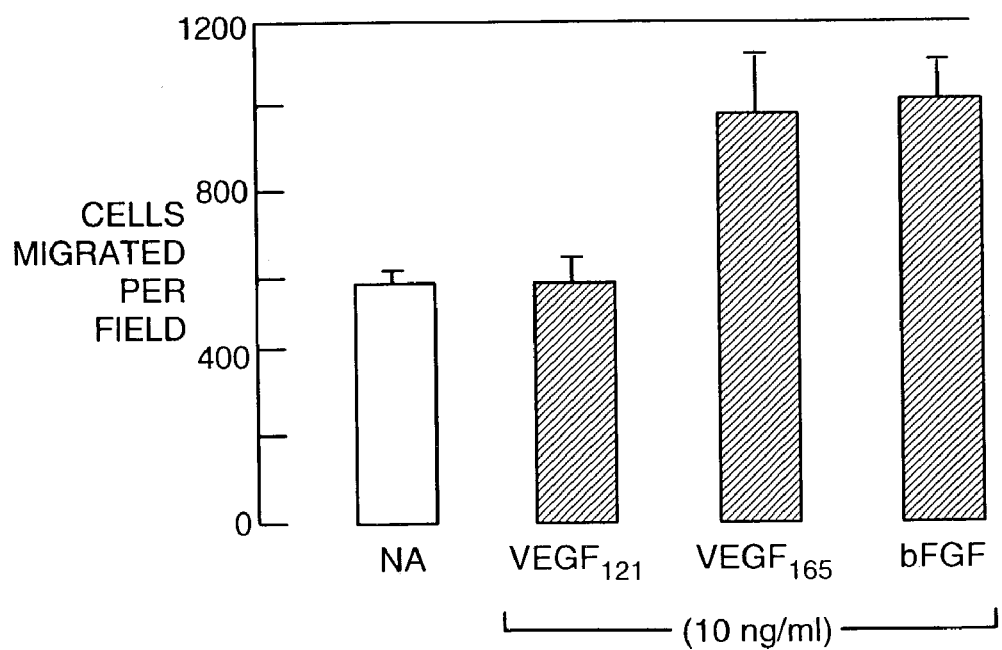

FIGS. 15A and 15B. $VEGF_{165}$ stimulation of MDA MB 231 cell motility. (15A) Dose response of $VEGF_{165}$ motility activity. (15B) Both $VEGF_{165}$ and bFGF stimulate motility but $VEGF_{121}$ does not.

Figure 16A:
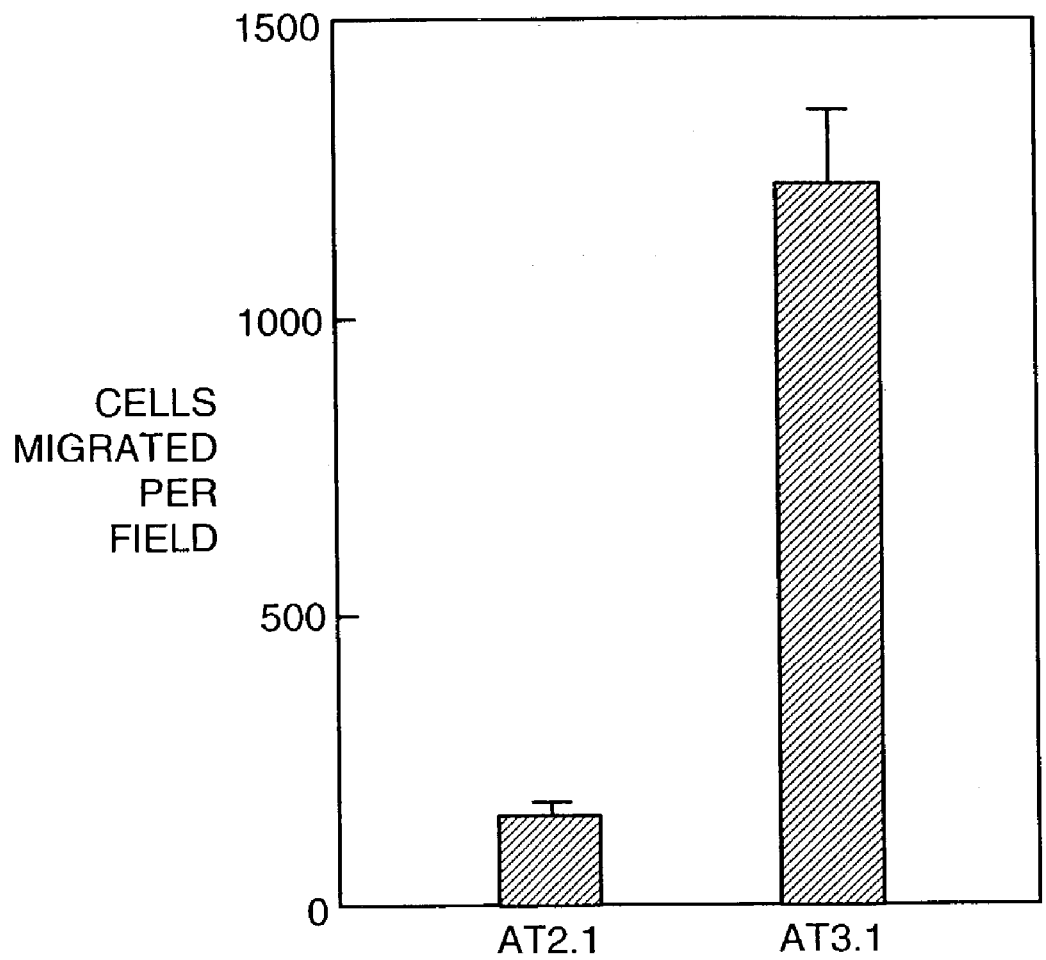
Figures 16B, 16C:
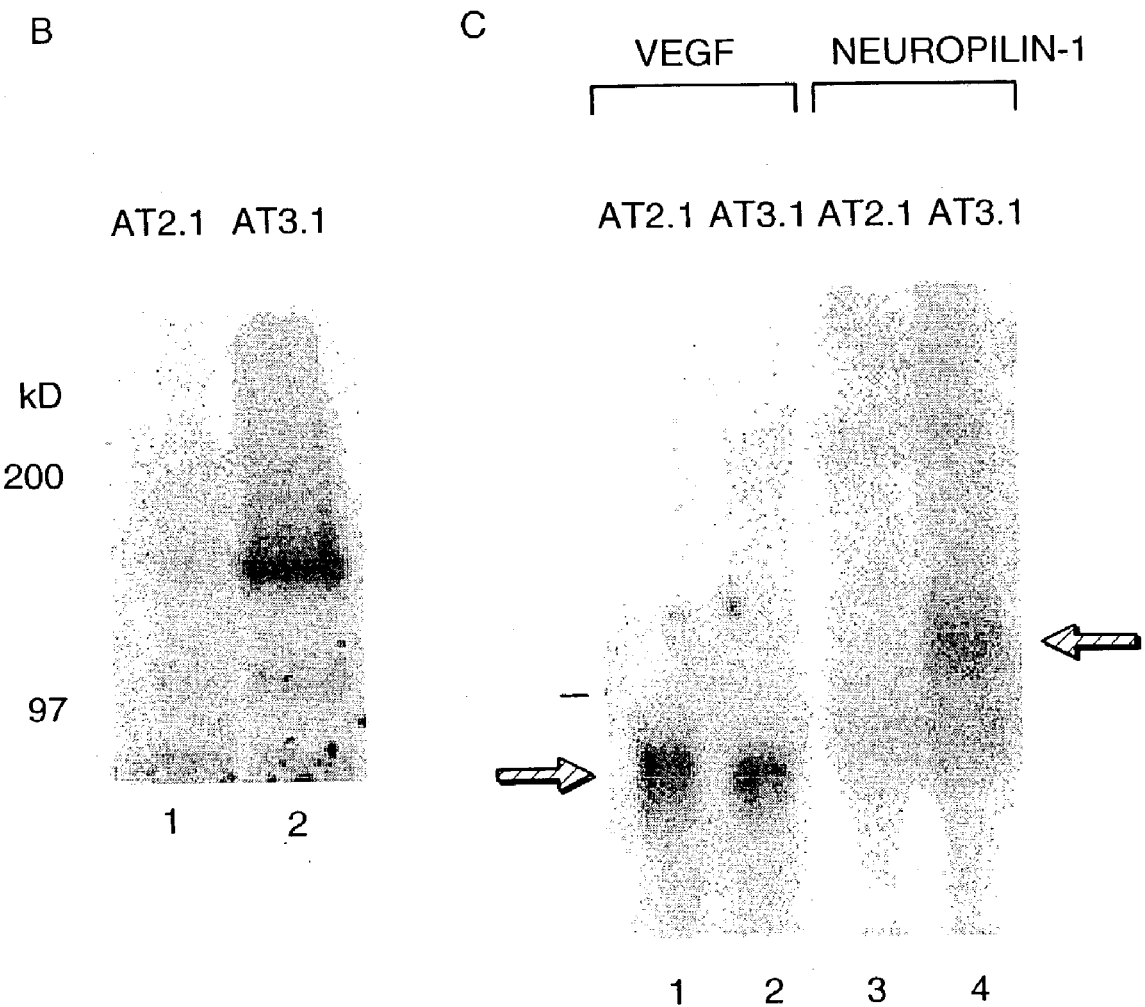

FIGS. 16A, 16B and 16C show motility and neuropilin-1 expression of Dunning rat prostate carcinoma cell lines AT3-1 (high motility, high metastatic potential) and AT2.1 (low motility, low metastatic potential) cells. (FIG. 16A) AT3.1 cells are more motile than AT2.1 cells in a Boyden chamber assay. (FIG. 16B) 125I-$VEGF_{165}$ cross-links neuropilin-1 on AT3.1 cells but does not cross-link to AT2.1 cells. (FIG. 16C) AT3.1 but not AT2.1 cells express neuropilin-1, while both cell types express VEGF.

Figure 17A:
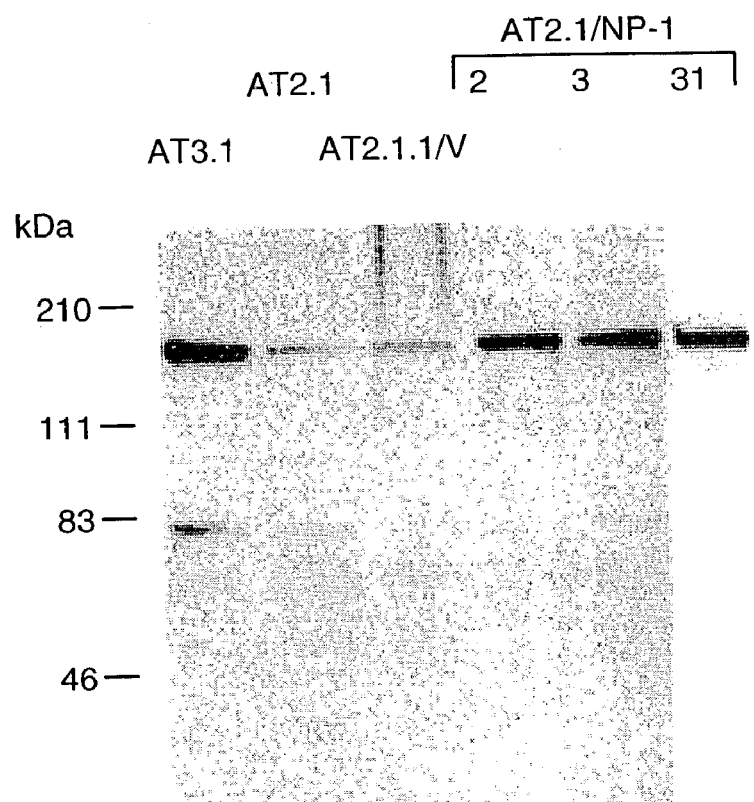
Figure 17B:
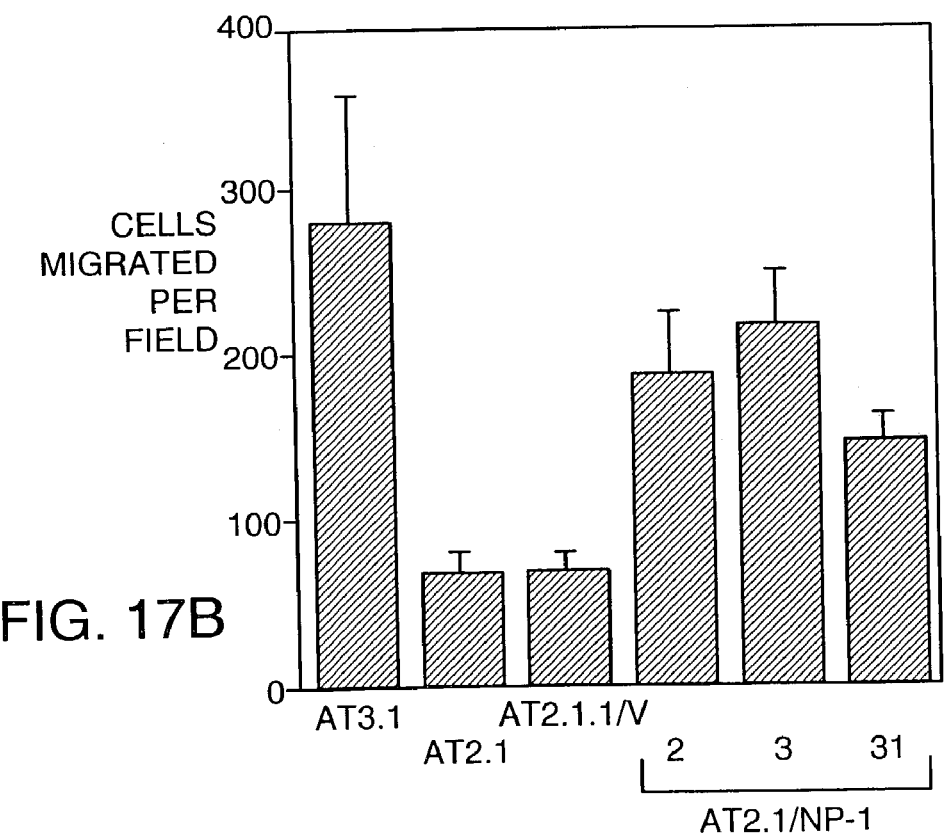

FIGS. 17A and 17B. Overexpression of neuropilin-1 in AT2.1 cells. (17A) Western blot, (17B) motility activity. Three AT2.1 clones (lanes 4,5,6) express higher amounts of neuropilin-1 protein and are more motile compared to parental AT2.1 cells or AT2.1 vector (AT2.1/V) controls and approach AT3.1 cell neuropilin-1 levels and migration activity.

Figure 18:
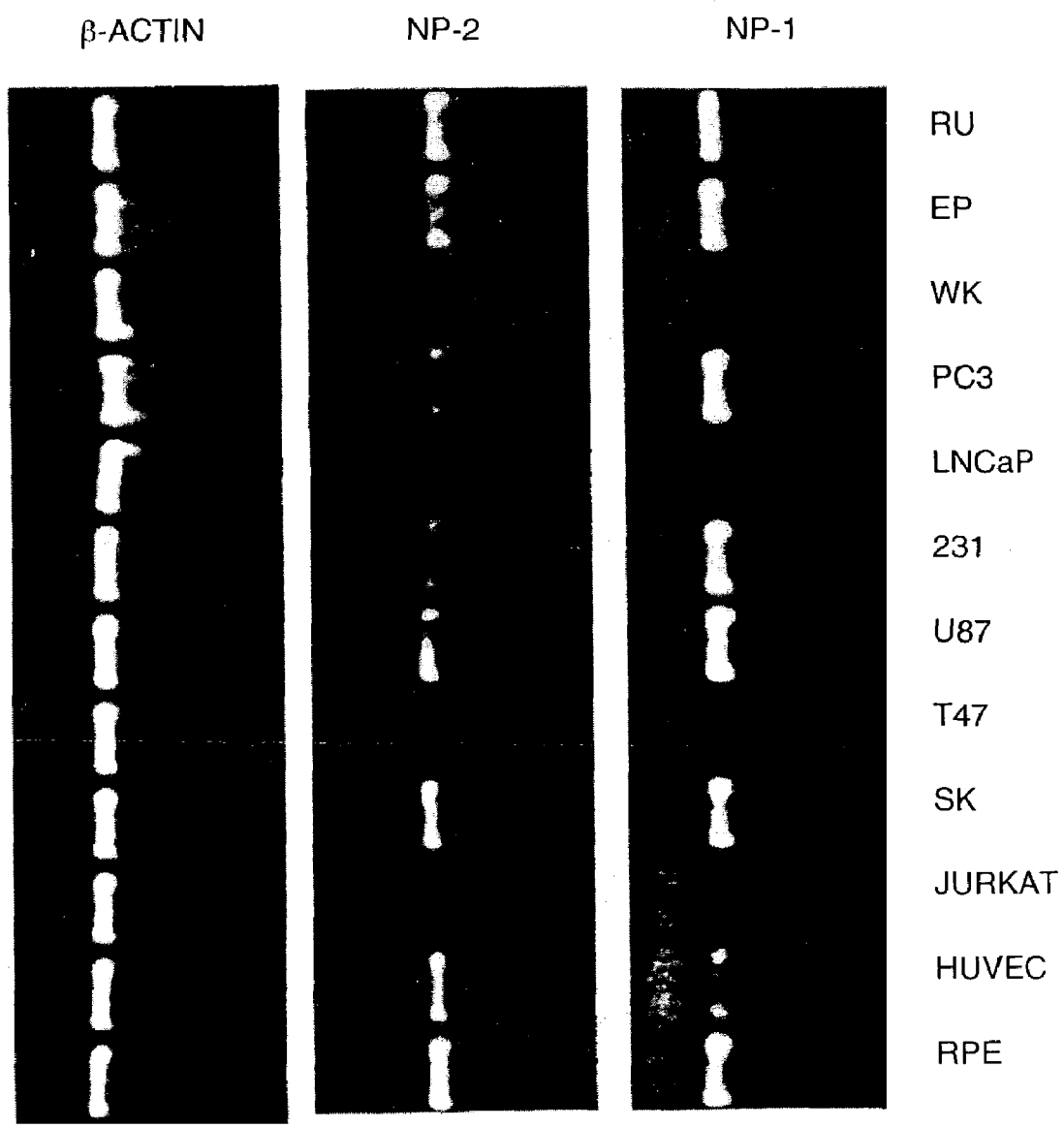

FIG. 18 shows expression of NP-1, NP-2 and β-actin in cancer cell lines and endothelial cells using reverse transcriptase PCR with the following primers:

```
Human NP-1
Forward (328-351):
5' TTTCGCAACGATAAATGTGGCGAT 3'   (SEQ ID NO:11)

Reverse (738-719):
5' TATCACTCCACTAGGTGTTG 3'       (SEQ ID NO:12)

Human NP-2
Forward (513-532):
5' CCAACCAGAAGATTGTCCTC 3'       (SEQ ID NO:13)

Reverse (1181-1162):
5' GTAGGTAGATGAGGCACTGA 3'.      (SEQ ID NO:14)
```

Figure 19:
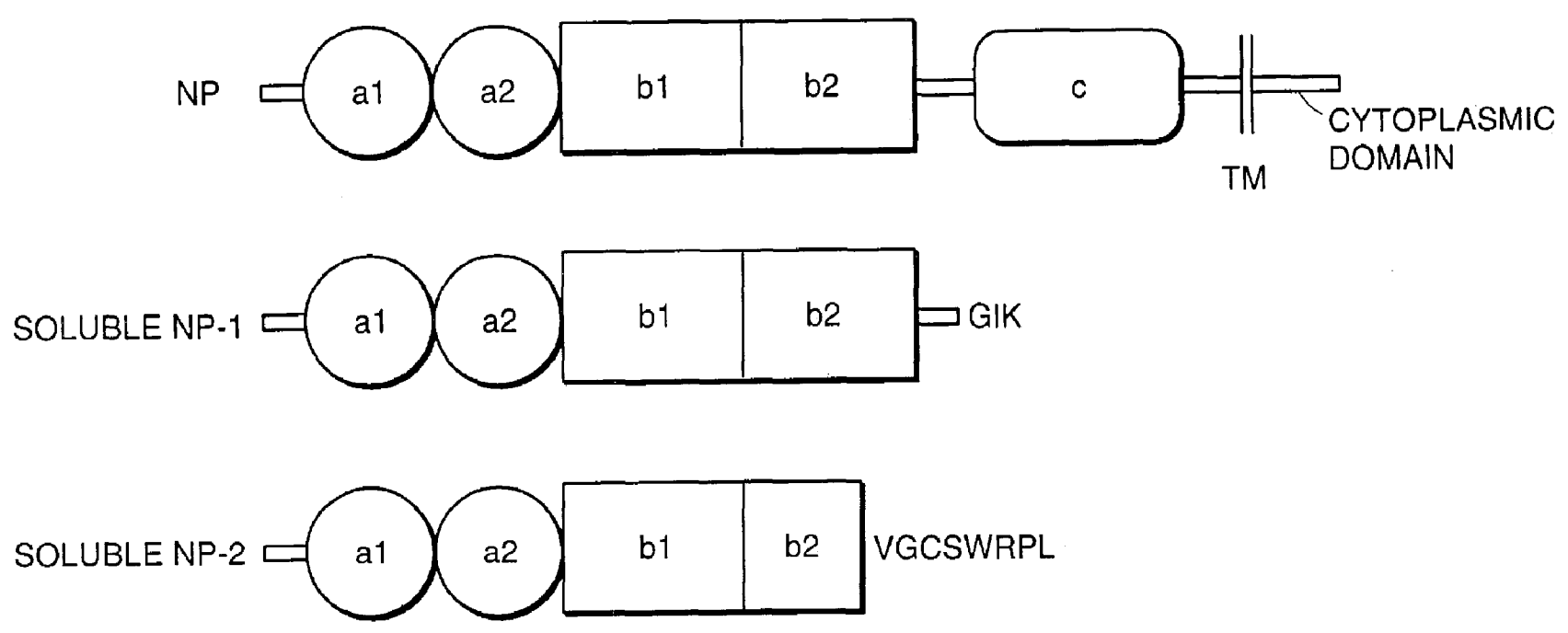

FIG. 19 is a schematic presentation of structures of (top) intact neuropilin (−1 and −2), of (middle) a newly cloned cDNA that encodes an ectodomain of neuropilin-1, and (bottom) of a newly cloned cDNA that encodes an ectodomain of neuropilin-2. These two new cDNAs represent alternative spliced isoforms.

Figure 20:
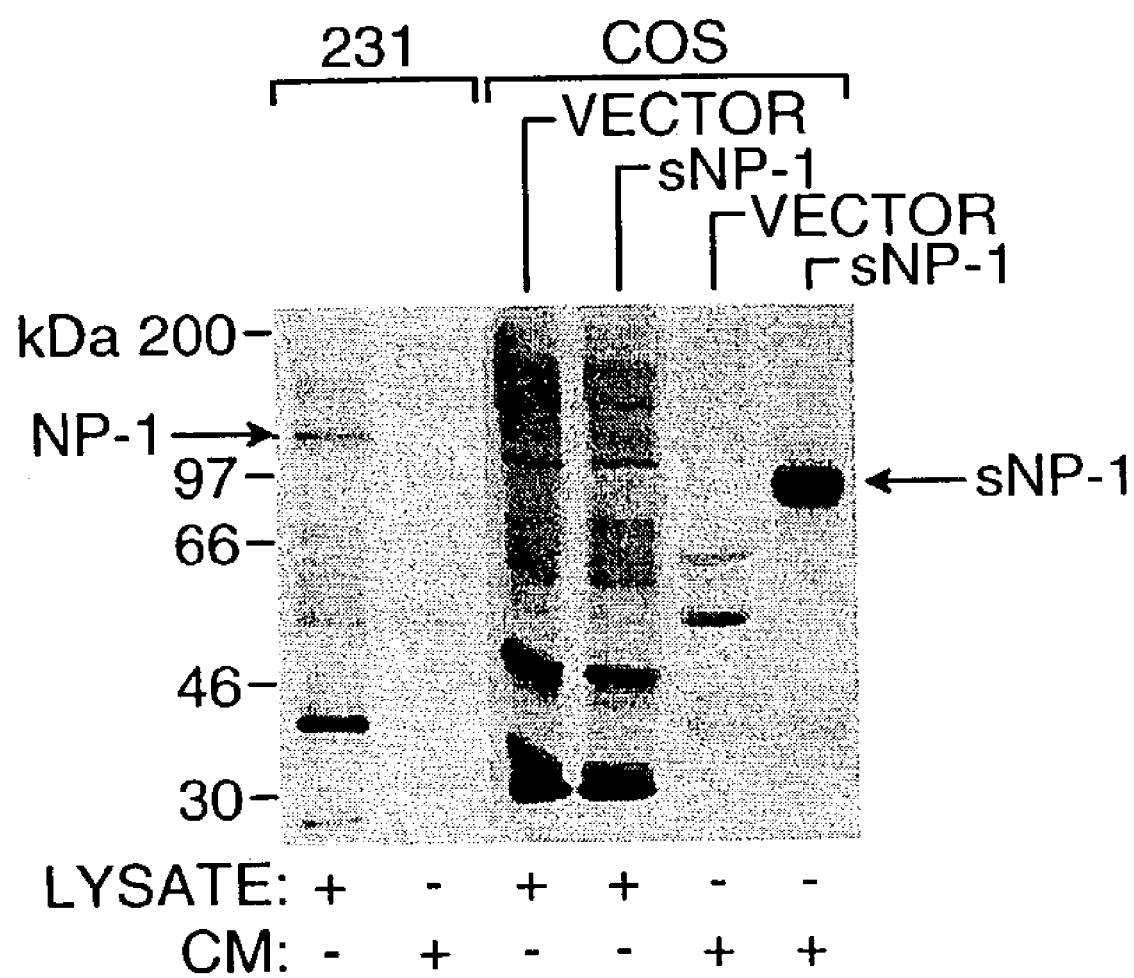

FIG. 20 shows cDNA encoding the C-terminally truncated neuropilin-1 isoform was transfected into COS cells. A soluble 90 kDa protein (sNP1) was detected by Western blot in the conditioned medium of cells expressing sNP1 but not in the vector control. Intact 130 kDa neuropilin-1 expressed by MDA MB 231 cells is shown in the first lane.

Figures 21A, 21B:
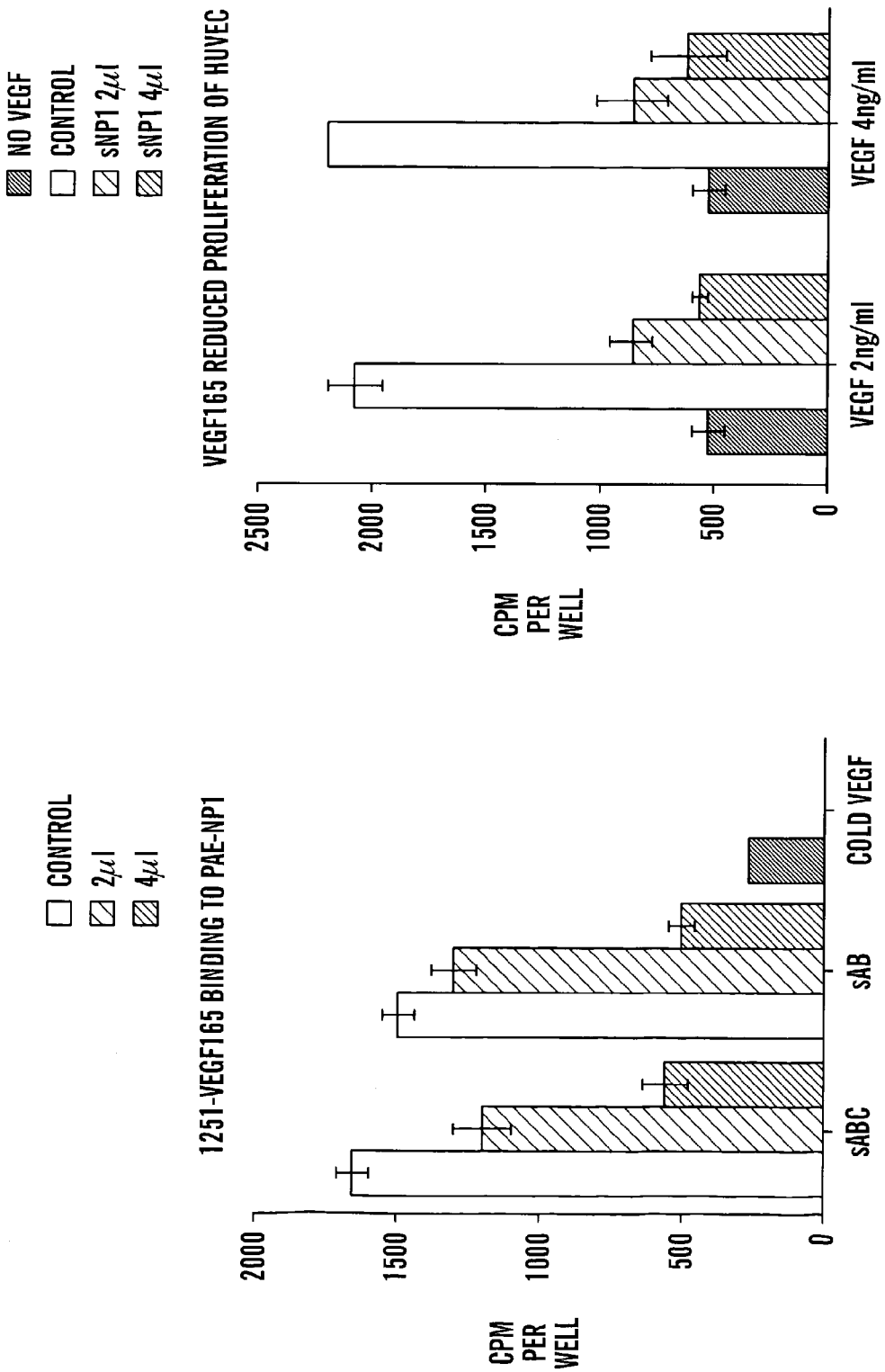

FIGS. 21A and 21B show Soluble neuropilin-1 protein preparations (FIG. 21A) inhibit $^{125}$I-VEGF$_{165}$ binding to PAE/NP cells and (Right) inhibit VEGF$_{165}$ mediated HUVEC proliferation. sABC is an engineered soluble neuropilin-1 truncated in the juxtamembrane region. sAB is a naturally occurring neuropilin-1 isoform missing c, TM and cytoplasmic domains. In this experiment sNP1 (FIG. 21B) is sABC produced in Example 3.

DETAILED DESCRIPTION OF THE INVENTION

The present invention relates to cDNA encoding a soluble neuropilin protein (sNP) which is isolated from neuropilin (NP) producing cells or is recombinantly engineered from NP-encoding DNA. NP-1 and NP-2 are preferred NPs but any neuropilin or VEGF receptor (VEGFR), where the constituents share at least about 85% homology with either of the above VEGF$_{165}$R/NP-1 and NP-2. More preferably, such constituent shares at least 90% homology. Still more preferably, each constituent shares at least 95% homology.

Homology is measured by means well known in the art. For example % homology can be determined by any standard algorithm used to compare homologies. These include, but are not limited to BLAST 2.0 such as BLAST 2.0.4 and i. 2.0.5 available from the NIH (See www.ncbi.ilm.nkh.gov/BLAST/newblast.html) (Altschul, S. F., et al. Nucleic Acids Res. 25: 3389-3402 (1997))and DNASIS (Hitachi Software Engineering America, Ltd.). These programs should preferably be set to an automatic setting such as the standard default setting for homology comparisons. As explained by the NIH, the scoring of gapped results tends to be more biologically meaningful than ungapped results.

For ease of reference, this disclosure will generally talk about VEGF$_{165}$R/NP-1 and NP-2 and/or homologs thereof but all teaching are applicable to the above-described homologs.

The present invention further relates to isolated and purified sNP protein. sNP, as used herein, refers to a protein which can specifically bind to a vascular endothelial cell growth factor containing exon 7 (SEQ ID NO:15), e.g., VEGF$_{165}$, and has VEGF antagonist activity as determined, for example, by the human umbilical vein endothelial cell (HUVEC) proliferation assay using VEGF$_{165}$ as set forth in Soker et al., J. Biol. Chem. 272, 31582-31588 (1997). Preferably, the sNP has at least a 25% reduction in HUVEC proliferation, more preferably a 50% reduction, even more preferably a 75% reduction, most preferably a 95% reduction.

VEGF antagonist activity of the sNPs may also be determined by inhibition of binding of labeled VEGF$_{165}$ to VEGF$_{165}$R as disclosed in Soker et al., J. Biol. Chem. 271, 5761-5767 (1996)) or to PAE/NP cells as set forth in the Examples. Preferably, the portion inhibits binding by at least 25%, more preferably 50%, most preferably 75%.

The term "isolated" means that the polypeptide or polynucleotide, e.g., DNA, is removed from its original environment. For example, a naturally-occurring polynucleotides or polypeptides present in a living animal is not isolated, but the same polynucleotides or DNA or polypeptides, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The nucleotide and amino acid sequence of fill length NP-1 is set forth in the Sequence listing as SEQ ID Nos: 1 and 2, respectively. The nucleotide and amino acid sequence of fill length NP-2 is set forth in the Sequence listing as SEQ ID Nos: 3 and 4, respectively.

DNA encoding human VEGF$_{165}$R/NP-1 or NP-2 and recombinant human VEGF$_{165}$R/NP-1 or NP-2 may be produced according to the methods set forth in the Examples.

Mammalian cell lines which produce NP-1 or NP-2 include, but are not limited to, MDA-MB-231 cells (ATCC HTB-26), PC3 prostate carcinoma cells and human umbilical vein endothelial cells (HUVEC) (ATCC CRL 1730).

Other cells and cell lines may also be suitable for use to isolate sNP. Selection of suitable cells may be done by screening for sNP binding activity on cell surfaces, in cell extracts or conditioned medium or by screening for gene expression by PCR or hybridization. Methods for detecting soluble receptor activity are well known in the art (Duan, D-S. R. et al., (1991) J. Biol. Chem., 266, pp. 413-418).

Full length NP producing cells such as human HUVEC cells (American Type Culture Collection, ATCC CRL 1730) [Hoshi, H. and McKeehan, W. L., Proc. Natl. Acad. Sci. U.S.A., (1984) 81, pp. 6413-6417] are grown according to the recommended culture conditions of the ATCC. Intact NP as well as extracellular region (sNP-1 and sNP-2) are shown in FIG. 8. The intact receptors have a domains homologous to complement components, b domains homologous to coagulation factors, a c domain homologous to MAM, a transmembrane domain (TM) and a short 40 amino acid cytoplasmic domain (cyto). Two of the inhibitory forms of this receptor, which are the subject of the present invention, are also shown in FIG. 8 and set forth in the sequence listing as SEQ ID NOS:6 and 8 and lack all of the c domain, the transmembrane domain and the cytoplasmic domain. Preferred sNPs of the invention additionally lack the a domains.

Neuropilin-1 (SEQ ID NO:2) domains are as follows: a1(amino acids 22-146), a2(amino acids 147-273), b1 (amino acids 275-430), b2 (amino acids 431-587), c (amino acids 646-809), TM (amino acids 857-884), cyto (amino acids 885-923)

Neuropilin-2 (SEQ ID NO:4) domains are as follows: a1(amino acids 24-148), a2(amino acids 149-275), b1 (amino acids 277-433), b2 (amino acids 434-594), c (amino acids 642-800), TM (amino acids 865-893), cyto (amino acids 894-931).

Any of a variety of procedures may be used to molecularly clone sNP cDNA. These methods include, but are not limited to, direct functional expression of the sNP gene following the construction of an sNP containing cDNA library in an appropriate expression vector system.

Another method is to screen a sNP containing cDNA library constructed in a bacteriophage or plasmid shuttle vector with a labelled oligonucleotide probe designed from the predicted amino acid sequence of sNP. One method consists of screening a sNP containing cDNA library constructed in a bacteriophage or plasmid shuttle vector with a partial cDNA encoding at least part of the full length NP protein. This partial cDNA is obtained by the specific PCR amplification of sNP DNA fragments through the design of oligonucleotide primers from the known sequence of full length NP-encoding DNA.

It is readily apparent to those skilled in the art that other types of libraries, as well as libraries constructed from other cells or cell types, may be useful for isolating sNP-encoding DNA. Additionally, suitable cDNA libraries may be prepared from cells or cell lines which have sNP activity. The selection of cells or cell lines for use in preparing a cDNA library to isolate sNP cDNA may be done by first measuring secreted sNP activity using the methods described herein.

Preparation of cDNA libraries can be performed by standard techniques well known in the art. Well known cDNA library construction techniques can be found for example, in *Molecular Cloning, A Laboratory Manual* (2nd Ed., Sambrook, Fritsch and Maniatis, Cold Spring Harbor, N.Y. 1989).

It is also readily apparent to those skilled in the art that DNA encoding sNP may also be isolated from a suitable genomic DNA library. Construction of genomic DNA libraries can be performed by standard techniques well known in the art. Well known genomic DNA library construction techniques can be found in Sambrook, et. al., supra.

Another means of obtaining sNP molecules is to recombinantly engineer them from DNA encoding the partial or complete amino acid sequence of an NP, e.g., NP-1 or NP-2. Using recombinant DNA techniques, DNA molecules are constructed which encode at least a portion of the NP capable of binding VEGF containing exon 7 without stimulating mitogenesis. Standard recombinant DNA techniques are used such as those found in Sambrook, et al., supra.

Using one of the preferred methods of the present invention, cDNA clones encoding sNP are isolated in a two-stage approach employing polymerase chain reaction (PCR) based technology and cDNA library screening. In the first stage, DNA oligonucleotides derived from the extracellular domain sequence information from the known full length NP is used to design degenerate oligonucleotide primers for the amplification of sNP-specific DNA fragments. In the second stage, these fragments are cloned to serve as probes for the isolation of complete sNP cDNA from a commercially available lambda gt10 cDNA library (Clontech) derived from HUVEC cells (ATCC CRL 1730).

Using another method, DNA encoding sNP is constructed from a DNA sequence encoding an NP. For purposes of illustration, DNA encoding NP-1 is utilized. Using the receptor DNA sequence, a DNA molecule is constructed which encodes the extracellular domain of the receptor, or the VEGF binding domain only. Restriction endonuclease cleavage sites are identified within the receptor DNA and can be utilized directly to excise the extracellular-encoding portion. In addition, PCR techniques as described above may be utilized to produce the desired portion of DNA. It is readily apparent to those skilled in the art that other techniques, which are standard in the art, may be utilized to produce sNP molecules in a manner analagous to those described above. Such techniques are found, for example, in Sambrook et al., supra.

In a preferred method sNP cDNAs are tagged with a His domain in the N-terminus of the a domain and subcloned into the pcDNA3.1 mammalian expression plasmid. Each of the plasmids is transfected into CHO-K1 cells and G418 resistant clones are isolated. Conditioned medium is collected and applied to a Con A Sepharose column, washed and Con A binding proteins are eluted. The eluate is applied to a Nickel column, washed and $Ni^{++}$ binding sNP proteins are eluted. Purified sNP is assayed for the ability to inhibit $^{125}I$-$VEGF_{165}$ binding to PAE/NP cells and $VEGF_{165}$ stimulation of C proliferation and motility. Smaller fragments are produced by PCR.

Our results indicate that VEGF binds to the b domain of neuropilin and that the a and c domains are not needed. See, FIG. 19 Smaller portions of b domain lacking increasingly larger segments of the N- and C-termini can be prepared by PCR using appropriate oligonucleotide primers. The amplified cDNA is then ligated into an expression vector, expressed in COS cells and conditioned medium tested for the ability to inhibit $^{125}I$-$VEGF_{165}$ binding to PAE/NP1 cells as shown for sNPs in FIG. 21A.

Additional truncated forms of NP can be constructed which contain the transmembrane region. Retention of the transmembrane may facilitate orientation of the inhibitor molecule at the target cell surface. Construction of transmembrane region containing molecules is done by standard techniques known in the art including but not limited to utilizing convenient restriction endonuclease cleavage sites or PCR techniques as described herein.

The cloned sNP cDNA obtained through the methods described above may be recombinantly expressed by molecular cloning into an expression vector containing a suitable promoter and other appropriate transcription regulatory elements, and transferred into prokaryotic or eukaryotic host cells to produce recombinant sNP. Techniques for such manipulations are fully described in Sambrook, et al., supra, and are well known in the art.

Expression vectors are defined herein as DNA sequences that are required for the transcription of cloned copies of genes and the translation of their mRNAs in an appropriate host. Such vectors can be used to express eukaryotic genes in a variety of hosts such as bacteria, bluegreen algae, fungal cells, yeast cells, plant cells, insect cells and animal cells.

Specifically designed vectors allow the shuttling of DNA between hosts such as bacteria-yeast or bacteria-animal or bacteria-insect cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency. Expression vectors may include, but are not limited to, cloning vectors, modified cloning vectors, specifically designed plasmids or viruses.

A variety of mammalian expression vectors may be used to express recombinant sNP in mammalian cells. Commercially available mammalian expression vectors which may be suitable for recombinant sVEGF-R expression, include but are not limited to, pMC1neo (Stratagene), pXT1 (Stratagene), pSG5 (Stratagene), EBO-pSV2-neo (ATCC 37593) pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUCTag (ATCC 37460), and gZD35 (ATCC 37565).

DNA encoding sNP may also be cloned into an expression vector for expression in a recombinant host cell. Recombinant host cells may be prokaryotic or eukaryotic, including but not limited to bacteria, yeast, mammalian cells including but not limited to cell lines of human, bovine, porcine, monkey and rodent origin, and insect cells including but not limited to *drosophila*, moth, mosquito and armyworm derived cell lines. Cell lines derived from mammalian species which may be suitable and which are commercially available, include but are not limited to, CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26) and MRC-5 (ATCC CCL 171). Insect cell lines which may be suitable and are commercially available include but are not limited to 3M-S (ATCC CRL 8851) moth (ATCC CCL 80) mosquito (ATCC CCL 194 and 195; ATCC CRL 1660 and 1591) and armyworm (Sf9, ATCC CRL 1711).

The expression vector may be introduced into host cells via any one of a number of techniques including but not limited to transformation, transfection, liposome or protoplast fusion, and electroporation. The expression vector-containing cells are clonally propagated and individually analyzed to determine whether they produce sNP protein. Identification of sNP expressing host cell clones may be done by several means, including but not limited to immunological reactivity with anti-sNP antibodies, binding to radiolabelled VEGF, and the presence of host cell-secreted sNP activity.

Following expression of sNP in a recombinant host cell, sNP protein may be recovered to provide sNP in active form, capable of binding VEGF without stimulating mitogenesis. Several sNP purification procedures are suitable for use. sNP may be purified from cell lysates and extracts, or from conditioned culture medium, by various combinations of, or individual application of salt fractionation, ion exchange chromatography, size exclusion chromatography, hydroxylapatite adsorption chromatography, reversed phase chromatography, heparin sepharose chromatography, VEGF165 ligand affinity chromatography, and hydrophobic interaction chromatography.

In addition, recombinant sNP can be separated from other cellular proteins by use of an immuno-affinity column made with monoclonal or polyclonal antibodies specific for full length sNP, or polypeptide fragments of sNP.

Preferably, sNPs can be purified by transfecting sNP containing DNA constructs into COS cells (transient transfection) and CHO cells (stable transfectants). The constructs used can be double tagged near the N-termini of the neuropilin (in the a domain which is not needed for VEGF binding) with, for example, both His and myc tags. Lectin column chromatography, is useful as a first step in sNP purification. The second step in the purification is to use a nickel column to bind the His-tagged proteins, and if necessary, anti-myc antibodies. The present inventors have shown that tagged sNPs are fully active in inhibiting VEGF binding to cells (FIG. 21A). To purify non-tagged sNPs, a combination of lectin and VEGF affinity chromatography is sufficient as shown in the examples for purification of intact neuropilin-1.

Purified sNP proteins can then be tested for effects on VEGF-mediated endothelial cell (e.g. HUVEC) migration and proliferation and the migration of endothelial cells out of rat aortic rings (in vitro angiogenesis). sNP proteins can also be tested in vivo for inhibition of VEGF-mediated angiogenesis in chick CAM, and mouse cornea models. FGF-2, which should not interact with sNPs can be used as a control. Purified sNP protein and DNA encoding the protein can also be test mouse models, in particular PC3 tumors grown subcutaneously or orthotopically into nude mice, to look for inhibition of angiogenesis, tumor growth and metastases.

The inhibitor of the present invention can be used for the inhibition of VEGF mediated activity including angiogenesis and tumor cell motility. The inhibitor can be used either topically or intravascularly. For topical applications the formulation would be applied directly at a rate of about 10 ng to about 1 mg/cm2/day. For intravaneous applications, the inhibitor is used at a rate of about 1 mg to about 10 mg/kg/day of body weight. For internal use, the formulation may be released directly into the region to be treated either from implanted slow release polymeric material or from slow release pumps or repeated injections. The release rate in either case is about 100 ng to about 100 mg/day/cm3.

For non-topical application the inhibitor is administered in combination with pharmaceutically acceptable carders or diluents such as phosphate buffer, saline, phosphate buffered saline, Ringer's solution, and the like, in a pharmaceutical composition, according to standard pharmaceutical practice. For topical application, various pharmaceutical formulations are useful for the administration of the active compound of this invention. Such formulations include, but are not limited to, the following: ointments such as hydrophilic petrolatum or polyethylene glycol ointment; pastes which may contain gums such as xanthan gum, solutions such as alcoholic or aqueous solutions; gels such as aluminum hydroxide or sodium alginate gels; albumins such as human or animal albumins; collagens such as human or animal collagens; celluloses such as alkyl celluloses, hydroxy alkyl celluloses and alkylhydroxyalkyl celluloses, for example methylcellulose, hydroxyethyl cellulose, carboxymethyl cellulose, hydroxypropyl methylcellulose, and hydroxypropyl cellulose; polyoxamers such as Pluronic.RTM. Polyols exemplified by Pluronic.RTM. F-127; tetronics such as tetronic 1508; and alginates such as sodium alginate.

The sNPs of the invention can be combined with a therapeutically effective amount of another molecule which negatively regulates angiogenesis which may be, but is not limited to, TNP470, platelet factor 4, thrombospondin-1, tissue inhibitors of metalloproteases (TIMP1 and TIMP2), prolactin (16-Kd fragment), angiostatin (38-Kd fragment of plasminogen), endostatin, bFGF soluble receptor, transforming growth factor beta, interferon alfa, soluble KDR and FLT-1 receptors and placental proliferin-related protein.

A sNP of the invention may also be combined with chemotherapeutic agents.

The DNA encoding a sNP of the invention can be used in the form of gene therapy and delivered to a host by any method known to those of skill in the art to treat disorders associated with VEGF.

A preferred embodiment of the present invention relates to methods of inhibiting angiogenesis of solid tumors to prevent further tumor growth and eventual metastasis. To this end, any solid tumor or the region surrounding the tumor accessible to gene transfer will be a target for the disclosed therapeutic applications. A DNA encoding an sNP, housed within a recombinant viral- or non-viral-based gene transfer system may be directed to target cells within proximity of the tumor by any number of procedures known in the art, including but not limited to (a) surgical procedures coupled with administration of an effective amount of the DNA to the site in and around the tumor (involving initial removal of a portion or the entire tumor, if possible); (b) injection of the gene transfer vehicle directly into or adjacent to the site of the tumor; and, (c) localized or systemic delivery of the gene transfer vector and/or gene product using techniques known in the art.

Any solid tumor that contains VEGF or neuropilin expressing cells will be a potential target for treatment. Examples, but by no means listed as a limitation of solid tumors which will be particularly vulnerable to gene therapy applications are (a) neoplasms of the central nervous system such as, but again not necessarily limited to glioblastomas, astrocytomas, neuroblastomas, meningiomas, ependymomas; (b) cancers of hormone-dependent, tissues such as protstate, testicles, uterus, cervix, ovary, mammary carcinomas including but not limited to carcinoma in situ, medullary carcinoma, tubular carcinoma, invasive (infiltrating) carcinomas and mucinous carcinomas; (c) melanomas, including but not limited to cutaneous and ocular melanomas; (d) cancers of the lung which at least include squamous cell carcinoma, spindle carcinoma, small cell carcinoma, adenocarcinoma and large cell carcinoma; and (e) cancers of the gastrointestinal system such as esophageal, stomach, small intestine, colon, colorectal, rectal and anal region which at least include adenocarcinomas of the large bowel.

A DNA fragment encoding an sNP may be delivered either systemically or to target cells in the proximity of a solid tumor of the mammalian host by viral or non-viral based methods. Viral vector systems which may be utilized in the present invention include, but are not limited to, (a) adenovirus vectors; (b) retrovirus vectors; (c) adeno-associated virus vectors; (d) herpes simplex virus vectors; (e) SV 40 vectors; (f) polyoma virus vectors; (g) papilloma virus vectors; (h) picarnovirus vectors; and (i) vaccinia virus vectors.

The recombinant virus or vector containing the DNA encoding the sNP of the present invention is preferably administered to the host by direct injection into a solid tumor and/or quiescent tissue proximal to the solid tumor, such as adipose or muscle tissue. It will of course be useful to transfect tumor cells in the region of targeted adipose and muscle tissue. Transient expression of the sNPs in these surrounding cells will result in a local extracellular increase in these proteins and will promote binding with VEGF, thus inhibiting binding of VEGF to the receptors.

Non-viral vectors which are also suitable include DNA-lipid complexes for example liposome-mediated or ligand/poly-L-Lysine conjugates, such as asialoglyco-protein-mediated delivery systems (see. e.g. Felgner et al., 1994, J. Biol. Chem. 269: 2550-2561; Derossi et al., 1995, Restor. Neurol. Neuros. 8: 7-10: and Abcallah et al., 1995, Biol. Cell 85:1-7). Direct injection of "naked" DNA may also be used.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

All references cited above or below are herein incorporated by reference.

The present invention is further illustrated by the following Examples. These Examples are provided to aid in the understanding of the invention and are not construed as a limitation thereof.

EXAMPLE 1

Experimental Procedures

Materials

Cell culture media, lipofectin and lipofectamin reagents for transfection were purchased from Life Technologies. Human recombinant $VEGF_{165}$ and $VEGF_{121}$ were produced in Sf-21 insect cells infected with recombinant baculovirus vectors encoding either human $VEGF_{165}$ or $VEGF_{121}$ as previously described (Cohen et al., *Growth Factors*, 7, 131-138 (1992); Cohen et al., *J. Biol. Chem.*, 270, 11322-11326 (1995)). GST VEGF exons 7+8 fusion protein was prepared in *E. Coli* and purified as previously described (Soker et al., *J. Biol. Chem.*, 271, 5761-5767 (1996)). Heparin, hygromycin B and protease inhibitors were purchased from Sigma (St. Louis, Mo.). $^{125}$I-Sodium, $^{32}$P-dCTP, and GeneScreen-Plus hybridization transfer membrane were purchased from DuPont NEN (Boston, Mass.). Disuccinimidyl suberate (DSS) and IODO-BEADS were purchased from Pierce Chemical Co. (Rockford, Ill.). Con A Sepharose was purchased from Pharmacia LKB Biotechnology Inc. (Piscataway, N.J.). RNAzol-B was purchased from TEL-TEST Inc. (Friendswood, Tex.). Silver Stain kit and Trans-Blot PVDF membranes were purchased from Bio-Rad Laboratories (Hercules, Calif.). Multiple tissue northern blot membranes were purchased from Clontech (Palo Alto, Calif.). PolyATract mRNA isolation kits were purchased from Promega (Madison, Wis.). RediPrime DNA labeling kits and molecular weight markers were purchased from Amersham (Arlington Heights, Ill.). Plasmids: pcDNA3.1 was purchased from Invitrogen (Carlsbad, Calif.), and pCPhygro, containing the CMV promoter and encoding hygromycin B phosphorylase, was kindly provided by Dr. Urban Deutsch (Max Plank Institute, Bad Nauheim, Germany). Restriction endonucleases and Ligase were purchased from New England Biolabs, Inc (Beverly, Mass.). NT-B2 photographic emulsion and x-ray film were purchased from the Eastman Kodak company (Rochester N.Y.).

Cell culture

Human umbilical vein EC (HUVEC) were obtained from American Type Culture Collection (ATCC) (Rockville, Md.), and grown on gelatin coated dishes in M-199 medium containing 20% fetal calf serum (FCS) and a mixture of glutamine, penicillin and streptomycin (GPS). Basic FGF (2 ng/ml) was added to the culture medium every other day. Parental porcine aortic endothelial (PAE) cells and PAE cells expressing KDR (PAE/KDR) (Waltenberger et al., *J. Biol. Chem.* 269, 26988-26995 (1994)) were kindly provided by Dr. Lena Claesson-Welsh and were grown in F12 medium containing 10% FCS and GPS. MDA-MB-231 cells and MDA-MB453 cells were obtained from ATCC, and grown in DMEM containing 10% FCS and GPS. The human melanoma cell lines, RU-mel, EP-mel and WK-mel were kindly provided by Dr. Randolf Byer (Boston University Medical School, Boston, Mass.), and grown in DMEM containing 2% FCS, 8% calf serum and GPS. Human metastatic prostate adenocarcinoma, LNCaP and prostate carcinoma, PC3 cells were kindly provided by Dr. Michael Freeman (Children's Hospital, Boston, Mass.), and grown in RPMI 1640 containing 5% FCS and GPS.

Purification and Protein Sequencing

Approximately $5\times10^8$ MDA-MB-231 cells grown in 150 cm dishes were washed with PBS containing 5 mM EDTA, scraped and centrifuged for 5 min at 500 g. The cell pellet was lysed with 150 ml of 20 mM HEPES, pH 8.0, 0.5% triton X-100 and protease inhibitors including 1 mM AEBSF, 5 µg/ml leupeptin and 5 µg/ml aprotinin for 30 min on ice, and the lysate was centrifuged at 30,000×g for 30 min. $MnCl_2$ and $CaCl_2$ were added to the supernatant to obtain a final concentration of 1 mM each. The lysate was absorbed onto a Con A Sepharose column (7 ml) and bound proteins were eluted with 15 ml 20 mM HEPES, pH 8.0, 0.2 M NaCl, 0.1% triton X-100 and 1 M methyl-α-D-mannopyranoside at 0.2 ml/min. The elution was repeated twice more at 30 minute intervals. The Con A column eluates were pooled and incubated for 12 h at 4° C. with 0.5 ml of $VEGF_{165}$-Sepharose beads, containing about 150 µg $VEGF_{165}$, prepared as described previously (Wilchek and Miron, *Biochem. Int.* 4, 629-635. (1982)). The $VEGF_{165}$-Sepharose beads were washed with 50 ml of 20 mM HEPES, pH 8.0, 0.2 M NaCl and 0.1% triton X-100 and then with 25 ml of 20 mM HEPES, pH 8.0. The beads were then boiled in SDS-PAGE buffer and bound proteins were separated by 6% SDS-PAGE. Proteins were transferred to a TransBlot PVDF membrane using a semi-dry electric blotter (Hoeffer Scientific), and the PVDF membrane was stained with 0.1% Coomassie Brilliant Blue in 40% methanol. The two prominent proteins in a 130-140 kDa doublet were cut out separately and N-terminally sequenced using an Applied Biosystems model 477A microsequenator as a service provided by Dr. William Lane of the Harvard Microchemistry facility (Cambridge, Mass.).

Expression Cloning and DNA Sequencing

Complementary DNA (cDNA) was synthesized from 5 µg 231 mRNA. Double-stranded cDNA was ligated to EcoRI adaptors, and size-fractionated on a 5-20% potassium acetate gradient. DNA fragments larger than 2 kb were ligated to an eukaryotic expression plasmid, pcDNA3.1. The plasmid library was transfected into *E. coli* to yield a primary library of approximately $1\times10^7$ individual clones. A portion of the transformed bacteria was divided into 240 pools, each representing approximately $3\times10^3$ individual clones. DNA prepared from each pool was used to transfect COS-7 cells seeded in 12 well dishes, using the Lipofectin reagent according to the manufacturer's instructions. Three days after transfection, the cells were incubated on ice for 2 h with $^{125}$I-$VEGF_{165}$ (10 ng/ml) in the presence of 1 µg/ml heparin, washed and fixed with 4% paraformaldehyde in PBS. $^{125}$I-$VEGF_{165}$ binding to individual cells was detected by overlaying the monolayers with photographic emulsion, NT-B2, and developing the emulsion after two days as described (Gearing et al., 1989). Seven positive DNA pools were identified and DNA from one of the positive pools was used to transform *E. Coli*. The *E. coli* were sub-divided into 50 separate pools and plated onto 50 LB ampicillin dishes, with each pool representing approximately 100 clones. DNA made from these pools was transfected into COS-7 cells which were screened for $^{125}$I-$VEGF_{165}$ binding as described above. Twenty positive pools were detected at this step, and their corresponding DNAs were used to transform *E. Coli*. Each pool was plated onto separate LB ampicillin dishes and DNA was prepared from 96 individual colonies and screened in a 96-well two dimensional grid for $_{125}$I-$VEGF_{165}$ binding to tranfected COS-7 cells as described above. Seven single clones were identified as being positive at this step. The seven positive plasmid clones were amplified and their DNA was analyzed by restriction enzyme digestion. Six clones showed an identical digestion pattern of digest and one was different. One clone from each group was submitted for automated DNA sequencing.

Northern Analysis

Total RNA was prepared from cells in culture using RNAzol according to the manufacturer's instructions. Samples of 20 µg RNA were separated on a 1% formaldehide-agarose gel, and transferred to a GeneScreen-Plus membrane. The membrane was hybridized with a $^{32}$P labeled fragment of human $VEGF_{165}R$/NP-1 cDNA, corresponding to nucleotides 63454 in the ORF, at 63° C. for 18 h. The membrane was washed and exposed to an x-ray film for 18 h. A commercially-obtained multiple human adult tissue mRNA blot (Clonetech, 2 µg/lane) was probed for human NP-1 in a similar manner. The multiple tissue blot was stripped by boiling in the presence of 0.5% SDS and re-probed with a $^{32}$P labeled fragment of KDR cDNA corresponding to nucleotides 2841-3251 of the ORF (Terman et al., *Oncogene* 6, 1677-1683 (1991))

Transfection of PAE Cells

Parental PAE cells and PAE cells expressing KDR (PAE/KDR) (Waltenberger et al., 1994) were obtained from Dr. Lena Claesson-Welsh. Human NP-1 cDNA was digested with XhoI and XbaI restriction enzymes and subcloned into the corresponding sites of pCPhygro, to yield pCPhyg-NP-1. PAE and PAE/KDR cells were grown in 6 cm dishes and transfected with 5 µg of pCPhyg-NP-1 using Lipofectamine, according to the manufacturer's instructions. Cells were allowed to grow for an additional 48 h and the medium was replaced with fresh medium containing 200 µg/ml hygromycin B. After 2 weeks, isolated colonies ($5-10\times10^3$ cell/colony) were transferred to separate wells of a 48 well dish and grown in the presence of 200 µg/ml hygromycin B. Stable PAE cell clones expressing $VEGF_{165}R$/NP-1 (PAE/NP-1) or co-expressing $VEGF_{165}R$/NP-1 and KDR (PAE/KDR/NP-1) were screened for $VEGF_{165}$ receptor expression by binding and cross linking of $^{125}$I-$VEGF_{165}$. For transient transfection, PAE/KDR cells were transfected with $VEGF_{165}R$/NP-1 as described above and after three days $_{125}$I-$VEGF_{165}$ cross-linking analysis was carried out.

Radio-iodination of VEGF, Binding and Cross-linking Experiments.

The radio-iodination of $VEGF_{165}$ and $VEGF_{121}$ using IODO-BEADS was carried out as previously described (Soker et al., *J. Biol. Chem.* 272,31582-31588 (1997)). The specific activity ranged from 40,000-100,000 cpm/ng protein. Binding and cross-linking experiments using $_{125}$I-$VEGF_{165}$ and $^{125}$I-$VEGF_{121}$ were performed as previously described (Gitay-Goren et al., *J. Biol. Chem.* 267, 6093-6098 (1992); Soker et al., *J. Biol. Chem.* 271, 5761-5767 (1996)). VEGF binding was quantitated by measuring the cell-associated radioactivity in a γ-counter (Beckman, Gamma 5500). The counts represent the average of three wells. All experiments were repeated at least three times and similar results were obtained. The results of the binding experiments were analyzed by the method of Scatchard using the LIGAND program (Munson and Rodbard, 1980). $^{125}$I-VEGF$_{165}$ and $^{125}$I-VEGF$_{121}$ cross linked complexes were resolved by 6% SDS/PAGE and the gels were exposed to an X-Ray film. X-ray films were subsequently scanned by using an IS-1000 digital imaging system (Alpha Innotech Corporation)

Purification of VEGF$_{165}$R

Figure 1:
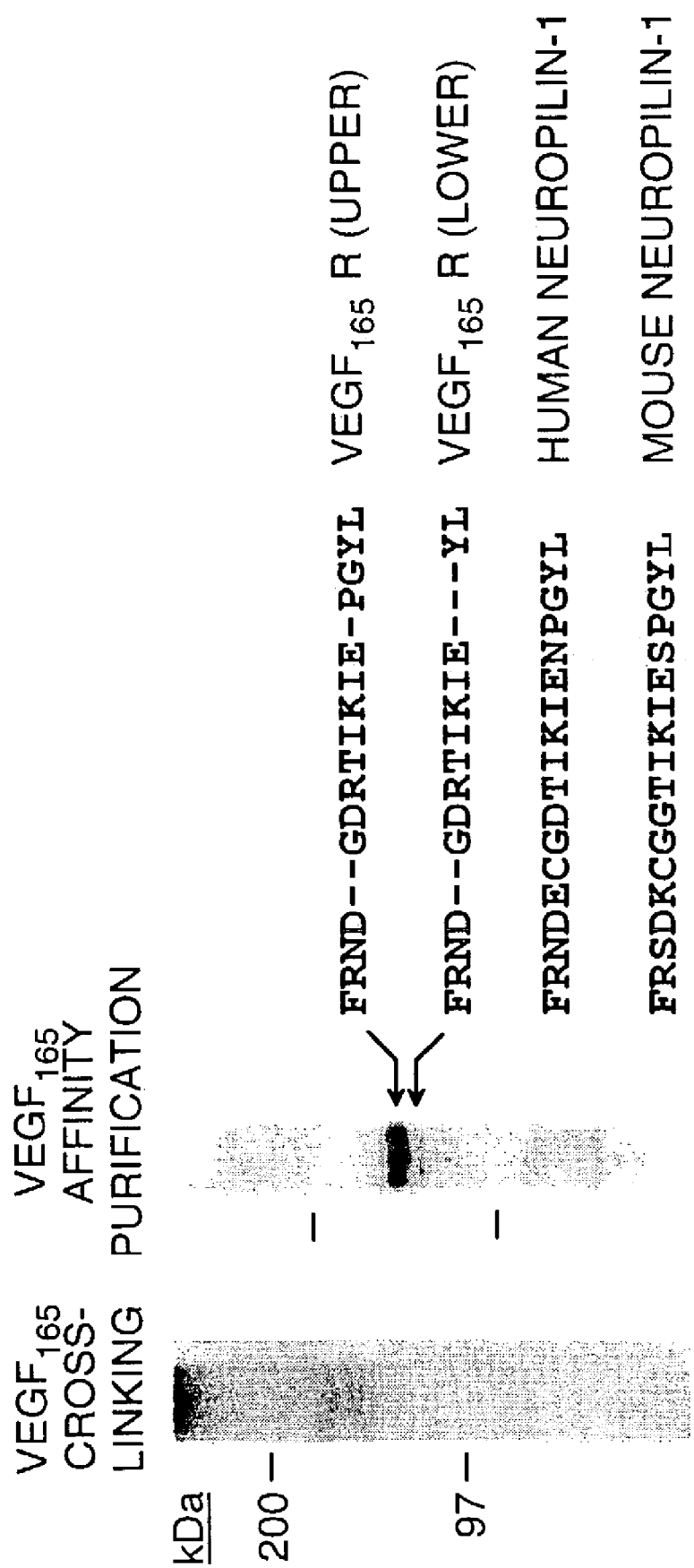
FIG. 1. Purification of $VEGF_{165}R$ From 231 Cells.
$^{125}I$-$VEGF_{165}$ (5 ng ml) was bound and cross-linked to receptors on 231 cells and analyzed by SDS PAGE and autoradiograpy (lane 1) $VEGF_{165}R$ was purified by Con A and $VEGF_{165}$ affinity column chromatograpy and analyzed by SDS-PAGE and silver stain (lane 2) Two prominent bands were detected (arrows) and N-terminally sequenced seperately. Their N-terminal 18 amino acid sequences are shown to the right of the arrows; SEQ ID NO:25 (upper) and SEQ ID NO:26 (Lower). The published N-terminal sequences of human (SEQ ID NO:9) and mouse neurophlin (SEQ ID NO:10)(Kawakami et al. *J. Neurobiol,* 29:1-17 (1995); He and Tesseier-Lavigne, *Cell* 90, 739-751 1997) are shown below .

Cross-linking of $^{125}$I-VEGF$_{165}$ to cell surface receptors of 231 cells results in formation of a 165-175 kDa labeled complex (Soker et al., *J. Biol. Chem.* 271, 5761-5767 (1996)). These cells have about 1-2×10$^5$ VEGF$_{165}$ binding sites/cell. In contrast to VEGF$_{165}$, VEGF$_{121}$ does not bind to the 231 cells and does not form a ligand-receptor complex (Soker et al., *J. Biol. Chem.* 271, 5761-5767 (1996)). The relatively high VEGF$_{165}$R number and the lack of any detectable KDR or Flt-1 mRNA in 231 cells (not shown) suggested that these cells would be a useful source for VEGF$_{165}$R purification. Preliminary characterization indicated that VEGF$_{165}$R is a glycoprotein and accordingly, a 231 cell lysate prepared from approximately 5×10$^8$ cells was absorbed onto a Con A Sepharose column. Bound proteins, eluted from the Con A column, were incubated with VEGF$_{165}$-Sepharose and the VEGF$_{165}$-affinity purified proteins were analyzed by SDS-PAGE and silver staining (FIG. 9, lane 2). A prominent doublet with a molecular mass of about 130-135 kDa was detected. This size is consistent with the formation of a 165-175 kDa complex of 40-45 kDa VEGF$_{165}$ bound to receptors approximately 130-135 kDa in size (FIG. 9, lane 1). The two bands were excised separately and N-terminal amino acid sequencing was carried out (FIG. 1, right). Both the upper and lower bands had similar N-terminal amino acid sequences which showed high degrees of sequence homology to the predicted amino acid sequences in the N-terminal regions of mouse (Kawakami et al., *J. Neurobiol,* 29, 1-17 (1995)) and human neuroplilin-1 (NP-1) (He and Tessier-Lavigne, *Cell* 90 739-751 (1997)).

Expression Cloning of VEGF$_{165}$R from 231 Cell-derived mRNA

Figure 2A:
FIGS. 2A and 2B. Isolation of $VEGF_{165}R$ cDNA by Expression Cloning. Photomicrographs (dark field illumination) of COS 7 cells binding $^{125}I$-$VEGF_{165}$. $^{125}I$-$VEGF_{165}$ was bound to transfected COS 7 cells which were then washed, fixed, and overlayed with photographic emulsion that was developed as described in the example.
Figure 2B:

Concomitant with the purification, VEGF$_{165}$R was cloned by expression cloning (Aruffo and Seed, *Proc. Natl. Acad. Sci. USA* 84, 8573-8577 (1987a); Aruffo and Seed, *EMBO J.,* 6, 3313-3316 (1987b); Gearing et al., *EMBO J.* 8, 3667-3676 (1989)). For expression cloning, 231 cell mRNA was used to prepare a cDNA library of approximately 10$^7$ clones in a eukaryotic expression plasmid. *E. coli* transformed with the plasmid library were divided into pools. The DNA prepared from each pool were transfected into COS-7 cells in separate wells and individual cells were screened for the ability to bind $^{125}$I-VEGF$_{165}$ as detected by autoradiography of monolayers overlayed with photographic emulsion (FIG. 2A). After three rounds of subpooling and screening, seven single positive cDNA clones were obtained. FIG. 2B shows binding of $^{125}$I-VEGF$_{165}$ to COS-7 cells transfected with one of these single positive clones (clone A2).

Restriction enzyme analysis revealed that six of the seven positive single clones had identical restriction digestion patterns but that one clone had a pattern that was different (not shown). Sequencing of one of these similar cDNA clones, clone A2 (FIG. 3), showed it to be identical to a sequence derived from a human-expressed sequence tag data bank (dbEST). This sequence also showed a high percentage of homology to the sequence of mouse neuropilin, NP-1 (Kawakami et al., *J. Neurobiol* 29, 1-17 (1995)). After we had cloned human VEGF$_{165}$R, two groups reported the cloning of rat and human receptors for semaphorin III and identified them to be NP-1 (He and Tessier-Lavigne, *Cell* 90, 739-751 (1997); Kolodkin al., *Cell* 90, 753-762 (1997)). The 231 cell-derived VEGF$_{165}$R cDNA sequence is virtually identical (see figure legend 3 for exceptions) to the human NP-1 sequence (He and Tessier-Lavigne, *Cell* 90, 739-751 (1997)). Significantly, the predicted amino acid sequence obtained by expression cloning (FIG. 3) confirmed the identification of VEGF$_{165}$R as NP-1 that was determined by N-terminal sequencing (FIG. 1), and we have therefore named this VEGF receptor, VEGF$_{165}$R/NP-1.

The human VEGF$_{165}$R/NP-1 cDNA sequence predicts an open reading frame (ORF) of 923 amino acids with two hydrophobic regions representing putative signal peptide and transmembrane domains (FIG. 3). Overall, the sequence predicts ectodomain, transmembrane and cytoplasmic domains consistent with the structure of a cell surface receptor. The N-terminal sequence obtained via protein purification as shown in FIG. 1 is downstream of a 21 amino acid putative hydrophobic signal peptide domain, thereby indicating directly where the signal peptide domain is cleaved and removed. The short cytoplasmic tail of 40 amino acids is consistent with results demonstrating that soluble VEGF$_{165}$R/NP-1 released by partial trypsin digestion of 231 cells is similar in size to intact VEGF$_{165}$R/NP-1 (not shown).

Sequence analysis of the one clone obtained by expression cloning that had a different restriction enzyme profile predicted an open reading frame of 931 amino acids with about a 47% homology to VEGF$_{165}$R/NP-1 (FIG. 4). This human cDNA has a 93% sequence homology with rat neuropilin-2 (NP-2) and is identical to the recently cloned human NP-2 (Chen et al., *Neuron,* 19, 547-559 (1997)).

Expression of VEGF$_{165}$R/NP-1 in Adult Cell Lines and Tissues

Reports of NP-1 gene expression have been limited so far to the nervous system of the developing embryo (Takagi et al., *Dev. Biol.* 122, 90-100 (1987); Kawakami et al., *J. Neurobiol.* 29, 1-17 (1995); Takagi et al., *Dev. Biol.* 170, 207-222 (1995)). Cell surface VEGF$_{165}$R/NP-1, however, is associated with non-neuronal adult cell types such as EC and a variety of tumor-derived cells (Soker et al., *J. Biol. Chem.* 271, 5761-5767 (1996)). Northern blot analysis was carried out to determine whether cells that crossed-linked $^{125}$I-VEGF$_{165}$ also synthesized VEGF$_{165}$R/NP-1 mRNA. (FIG. 5). VEGF$_{165}$R/N-1 mRNA levels were highest in 231 and PC3 cells. VEGF$_{165}$R/NP-1 mRNA was detected to a lesser degree in HUVEC, LNCaP, EP-mel and RU-mel cells. There was little if any expression in MDA-MB-453 and WK-mel cells. The VEGF$_{165}$R/NP-1 gene expression patterns were consistent with our previous results showing that HUVEC, 231, PC3, LNCaP, EP-mel and RU-mel cells bind $^{125}$I-VEGF$_{165}$ to cell surface VEGF$_{165}$R/NP-1 but that MDA-MB-453 and WK-mel cells do not (Soker et al., *J. Biol. Chem.* 271, 5761-5767 (1996)).

VEGF$_{165}$RN-1 gene expression was analyzed also by Northern blot in a variety of adult tissues in comparison to KDR gene expression (FIG. 6). VEGF$_{165}$R/NP-1 mRNA levels were relatively highly in adult heart and placenta and relatively moderate in lung, liver, skeletal muscle, kidney and pancreas. A relatively low level of VEGF$_{165}$R/NP-1 mRNA was detected in adult brain. Interestingly, previous analysis of NP-1 gene expression in mouse and chicken brain suggested that this gene was expressed primarily during embryonic development and was greatly diminished after birth (Kawakami et al., *J. Neurobiol.* 29, 1-17 (1995); Takagi et al., *Dev. Biol.* 170, 207-222 (1995)). The tissue distribution of KDR mRNA was similar to that of VEGF$_{165}$R/NP-1 with the exception that it was not expressed highly in the heart. These results indicate that VEGF$_{165}$R/NP-1 is expressed widely in adult non-neuronal tissue, including tissues in which anaiogenesis occurs such as heart and placenta.

Characterization of VEGF$_{165}$ Binding to VEGF$_{165}$R/NP-1

In order to characterize the binding properties of VEGF$_{165}$R/NP-1, porcine aortic endothelial (PAE) cells were transfected with the cDNA of VEGF$_{165}$R/NP-1 The PAE cells were chosen for these expression studies because they express neither KDR, Flt-1 (Waltenberger et al., *J. Biol. Chem.* 269, 26988-26995 (1994)) nor VEGF$_{165}$R. Stable cell lines synthesizing VEGF$_{165}$R/NP-1 (PAE/NP-1) were established and $^{125}$I-VEGF$_{165}$ binding experiments were carried out (FIG. 7). $^{125}$I-VEGF$_{165}$ binding to PAE/NP-1 cells increased in a dose-dependent manner and reached saturation at approximately 30 ng/ml demonstrating that VEGF$_{165}$R/NP-1 is a specific VEGF$_{165}$ receptor (FIG. 7A). Scatchard analysis of VEGF$_{165}$ binding revealed a single class of VEGF$_{165}$ binding sites with a $K_d$ of approximately $3.2 \times 10^{-10}$M and approximately $3 \times 10^5$ $^{125}$I-VEGF$_{165}$ binding sites per cell (FIG. 7B). Similar $K_d$ values were obtained for several independently-generated PAE/NP-1 clones, although the receptor number varied from clone to clone (not shown). The $K_d$ of $3 \times 10^{-10}$ M for the PAE/NP-1 cell lines is consistent with the $2$-$2.8 \times 10^{-10}$ M $K_d$ values obtained for VEGF$_{165}$R/NP-1 expressed naturally by HUVEC and 231 cells (Gitay-Goren et al., *J. Biol. Chem.* 267, 6093-6098 (1992); Soker et al., *J. Biol. Chem.* 271, 5761-5767 (1996)). The binding of $^{125}$I-VEGF$_{165}$ to PAE/NP-1 cells was enhanced by 1 μg/ml heparin (not shown), consistent with previous studies showing that heparin enhances $^{125}$I-VEGF$_{165}$ binding to VEGF$_{165}$R/NP-1 on HUVEC and 231 cells (Gitay-Goren et al., *J. Biol. Chem.* 267, 6093-6098 (1992); Soker et al., *J. Biol. Chem.* 271, 5761-5767 (1996)).

Isoform-specific Binding of VEGF to Cells Expressing VEGF$_{165}$R/NP-1

VEGF$_{165}$, but not VEGF$_{121}$, binds to VEGF$_{165}$R/NP-1 on HUVEC and 231 cells (Gitay-Goren et al., *J. Biol. Chem.* 271, 5519-5523 (1992); Soker et al., *J. Biol. Chem.* 271, 5761-5767 (1996)). To ascertain whether cells transfected with VEGF$_{165}$R/NP-1 had the same binding specificity. PAE/NP-1 cells were incubated with $^{125}$I-VEGF$_{165}$ or $^{125}$I-VEGF$_{121}$ followed by cross-linking (FIG. 8). $^{125}$I-VEGF$_{165}$ did not bind to parental PAE cells (FIG. 8, lane 3) but did bind to PAE/NP-1 cells via VEGF$_{165}$R/NP-1 (FIG. 8, lane 4). The radiolabeled complexes formed with VEGF$_{165}$R/NP-1 were similar in size to those formed in HUVEC (FIG. 8, lane 1) and PC3 cells (FIG. 8, lane 2). On the other hand, $^{125}$I-VEGF$_{121}$, did not bind to either parental PAE (FIG. 8, lane 7) or to PAE/NP-1 cells (FIG. 8, lane 8). These results demonstrate that the VEGF isoform-specific binding that occurs with cells expressing endogenous VEGF$_{165}$R/NP-1 such as HUVEC, 231 and PC3 cells, can be replicated in cells transfected with VEGF$_{165}$R/NP-1 cDNA and support the finding that VEGF$_{165}$R and NP-1 are identical.

Co-expression of VEGF$_{165}$R/NP-1 and KDR Modulates VEGF$_{165}$ Binding to KDR To determine whether expression of VEGF$_{165}$R/NP-1 had any effect on VEGF$_{165}$ interactions with KDR, PAE cells that were previously transfected with KDR cDNA to produce stable clones of PAE/KDR cells (Waltenberger et al., *J. Biol. Chem.* 269, 26988-26995 (1994)), were transfected with VEGF$_{165}$R/NP-1 cDNA and stable clones expressing both receptors (PAE/KDR/NP-1) were obtained. These cells bound $^{125}$I-VEGF$_{165}$ to KDR (FIG. 8, lane 6, upper complex) and to VEGF$_{165}$R/NP-1 (FIG. 8, lane 6, lower complex) to yield a cross-linking profile similar to HUVEC (FIG. 8, lane 1). On the other hand, the PAE/KDR/NP-1 cells bound $^{125}$I-VEGF$_{121}$ to form a complex only with KDR (FIG. 8, lanes 9 and 10), consistent with the inability of VEGF$_{121}$ to bind VEGF$_{165}$R/NP-1.

It appeared that in cells co-expressing KDR and VEGF$_{165}$R/NP-1 (FIG. 8, lane 6), the degree of $^{125}$I-VEGF$_{165}$-KDR 240 kDa complex formation was enhanced compared to the parental PAE/KDR cells (FIG. 8, lane 5). These results were reproducible and the degree of $^{125}$I-VEGF$_{165}$-KDR 240 kDa complex formation in different clones was correlated positively with the levels of VEGF$_{165}$R/NP-1 expressed (not shown). However, it could not be ruled out definitively that these differential KDR binding results were possibly due to clonal selection post-transfection. Therefore, parental PAE/KDR cells were transfected with VEGF$_{165}$R/NP-1 cDNA and $^{125}$I-VEGF$_{165}$ was bound and cross-linked to the cells three days later in order to avoid any diversity of KDR expression among individual clones (FIG. 9). A labeled 240 kDa complex containing KDR was formed in parental PAE/KDR cells (FIG. 9, lane 1) and in PAE/KDR cells transfected with the expression vector (FIG. 9, lane 2). However, when $^{125}$I-VEGF$_{165}$ was cross-linked to PAE/KDR cells transiently expressing VEGF$_{165}$R/NP-1, a more intensely labeled 240 kDa complex, about 4 times greater, was observed (FIG. 9, lane 3), compared to parental PAE/KDR cells (FIG. 9, lane 1) and PAE/KDR cells transfected with expression vector (FIG. 9, lane 2). These results suggest that co-expression of KDR and VEGF$_{165}$R/NP-1 genes in the same cell enhances the ability of VEGF$_{165}$ to bind to KDR.

A GST-VEGF Exon 7+8 Fusion Protein Inhibits VEGF$_{165}$ Binding to VEGF$_{165}$R/NP-1 and KDR We have shown that $^{125}$I-VEGF$_{165}$ binds to VEGF$_{165}$R/NP-1 through its exon 7-encoded domain (Soker et al., *J. Biol. Chem.* 271, 5761-5767 (1996)). In addition, a GST fusion protein containing the peptide encoded by VEGF exon 7+8 (GST-Ex 7+8), inhibits completely the binding of $^{125}$I-VEGF$_{165}$ to VEGF$_{165}$R/NP-1 associated with 231 cells and HUVEC (Soker et al., *J. Biol. Chem.* 271, 5761-5767 (1996); Soker et al., *J. Biol. Chem.* 272, 31582-31588 (1997)). When, added to PAE/NP-1 cells, the fusion protein completely inhibited binding to VEGF$_{165}$R/NP-1 (FIG. 10, lane 2 compared to lane 1). On the other hand, it did not inhibit $^{125}$I-VEGF$_{165}$ binding at all to KDR (FIG. 10, lane 4 compared to lane 3). Thus, these results demonstrate that GST-Ex 7+8 binds directly to VEGF$_{165}$R/NP-1 but does not bind to KDR. The effects of GST-Ex 7+8 are different, however, in cells co-expressing both VEGF$_{165}$R/NP-1 and KDR (PAE/KDR/NP-1). Consistent with the results in FIGS. 8 and 9, the degree of $^{125}$I-VEGF$_{165}$ binding to KDR in PAE/KDR/NP-1 cells (FIG. 10, lane 5) was greater than to the parental PAE/KDR cells (FIG. 10, lane 3). Interestingly, in PAE/KDR/NP-1 cells, GST-Ex 7+8 inhibited not only $^{125}$I-VEGF$_{165}$ binding to VEGF$_{165}$R/NP-1 completely as expected, but it also inhibited binding to KDR substantially which was unexpected (FIG. 10, lane 6 compared to lane 5). In the presence of GST-Ex 7+8, binding of $^{125}$I-VEGF$_{165}$ to KDR in these cells was reduced to the levels seen in parental PAE/KDR cells not expressing VEGF$_{165}$R/

NP-1 (FIG. 10, lane 6 compared to lanes 3 and 4). Since the fusion protein does not bind directly to KDR, these results suggest that inhibiting the binding of $^{125}$I-VEGF$_{165}$ to VEGF$_{165}$R/NP-1 directly, inhibits its binding to KDR indirectly. Taken together, the results in FIGS. 8, 9 and 10 suggest that interactions of VEGF$_{165}$ with VEGF$_{165}$R/NP-1 enhance VEGF interactions with KDR.

Neuropilin-1 is an Isoform-specific VEGF$_{165}$ Receptor

Recently, we described a novel 130-135 kDa VEGF cell surface receptor that binds VEGF$_{165}$ but not VEGF$_{121}$ and that we named, accordingly, VEGF$_{165}$R (Soker et al., *J. Biol. Chem.* 271, 5761-5767 (1996)). We have now purified VEGF$_{165}$R, expression cloned its cDNA, and shown it to be identical to human neuropilin-1 (NP-1) (He and Tessier-Lavigne, *Cell* 90 739-751 (1997)). The evidence that VEGF$_{165}$R is identical to NP-1 and that NP-1 serves as a receptor for VEGF$_{165}$ is as follows: i) purification of VEGF$_{165}$R protein from human MDA-MB-231 (231) cells using VEGF affinity, yielded a 130-140 kDa doublet upon SDS-PAGE and silver stain. N-terminal sequencing of both proteins yielded the same N-terminal sequence of 18 amino acids that demonstrated a high degree of homology to mouse NP-1 (Kawakami et al., *J. Neurobiol.* 29, 1-17 (1995)); ii) After we purified VEGF$_{165}$R from human 231 cells, the cloning of human NP-1 was reported (He and Tessier-Lavigne, *Cell* 90, 739-751 (1997)) and the N-terminal sequence of human VEGF$_{165}$R was found to be identical to a sequence in the N-terminal region of human NP-1; iii) Expression cloning using a 231 cell cDNA library resulted in isolation of several cDNA clones and their sequences were identical to the human NP-1 cDNA sequence (He and Tessier-Lavigne, *Cell* 90, 739-751 (1997)). The combination of purification and expression cloning has the advantage over previous studies where only expression cloning was used (He and Tessier-Lavigne, *Cell* 90, 739-751 (1997); Kolodkin et al., *Cell* 90, 753-767 (1997)), in allowing unambiguous identification of the NP-1 protein N-terminus, iv) Northern blot analysis of NP-1 gene expression was consistent with previous $^{125}$I-VEGF$_{165}$ cross-linking experiments (Soker et al., *J. Biol. Chem.* 271, 5761-5767 (1996)). Cells that bound VEGF$_{165}$ to VEGF$_{165}$R synthesized relatively abundant NP-1 mRNA while cells that showed very little if any VEGF$_{165}$ binding, did not synthesize much if any NP-1 mRNA; v) when NP-1 was expressed in PAE cells, the transfected, but not the parental cells, were able to bind VEGF$_{165}$ but not VEGF$_{121}$, consistent with the isoform specificity of binding previously shown for HUVEC and 231 cells (Soker et al., *J. Biol. Chem.* 271, 5761-5767 (1996)). Furthermore, the K$_d$ of $^{125}$I-VEGF$_{165}$ binding of to PAE expressing NP-1 was about $3 \times 10^{-10}$ M, consistent with previous K$_d$ binding values of $2\text{-}2.8 \times 10^{-10}$ M for 231 cells and HUVEC (Soker et al., *J. Biol. Chem.* 271, 5761-5767 (1996)); and vi) The binding of VEGF$_{165}$ to cells expressing NP-1 post-transfection was more efficient in the presence of heparin as was the binding of this ligand to HUVEC and 231 cells (Gitay-Goren et al., *J. Biol. Chem.* 267, 6093-6098 (1992); Soker et al., *J. Biol. Chem.* 271, 5761-5767 (1996)). Taken together, these results show not only that VEGF$_{165}$R is identical to NP-1 but that it is a functional receptor that binds VEGF$_{165}$ in an isoform-specific manner. Accordingly, we have named this VEGF receptor VEGF$_{165}$R/NP-1.

In addition to the expression cloning of VEGF$_{165}$R/NP-1 cDNA, another human cDNA clone was isolated whose predicted amino acid sequence was 47% homologous to that of VEGF$_{165}$R/NP-1 and over 90% homologous to rat neuropilin-2 (NP-2) which was recently cloned (Kolodkin et al., *Cell* 90, 753-762 (1997)). NP-2 binds members of the collapsin/semaphorin family selectively (Chen et al., *Neuron* 19, 547-559 (1997)).

The discovery that NP-1 serves as a receptor for VEGF$_{165}$ was a surprise since NP-1 had previously been shown to be associated solely with the nervous system during embryonic development (Kawakami et al., *J. Neurobiol.* 29, 1-17 (1995); Takagi et al., *Dev. Biol.* 170, 207-222 (1995)) and more recently as a receptor for members of the collapsin/semaphorin family (He and Tessier-Lavigne, *Cell* 90739-751 (1997); Kolodkin et al., *Cell* 90, 753-762 (1997)). NP-1 is a 130-140 kDa transmembrane glycoprotein first identified in the developing *Xenopus* optic system (Takagi et al., *Dev. Biol.* 122, 90-100 (1987); Takagi et al., *Neuron* 7, 295-307 (1991)). NP-1 expression in the nervous system is highly regulated spatially and temporally during development and in particular is associated with those developmental stages when axons are actively growing to form neuronal connections. (Fujisawa et al., *Dev. Nezirosci.* 17, 343-349 (1995); Kawakami et al., *J. Neurobiol* 29, 1-17 (1995); Takagi et al., *Dev. Biol.* 170, 207-222 (1995)). The NP-1 protein is associated with neuronal axons but not the stomata (Kawakami et al., *J. Neurobiol* 29, 1-17 (1995)). Functionally, neuropilin has been shown to promote neurite outgrowth of optic nerve fibers in vitro (Hirata et al., *Neurosci. Res.* 17, 159-169 (1993)) and to promote cell adhesiveness (Tagaki et al., *Dev. Biol* 170, 207-222 (1995)). Targeted disruption of NP-1 results in severe abnormalities in the trajectory of efferent fibers of the peripheral nervous system (Kitsukawa et al., *Neuron* 19, 995-1005 (1997)). Based on the these studies, it has been suggested that NP-1 is a neuronal cell recognition molecule that plays a role in axon growth and guidance (Kawakami et al., *J. Neurobiol.* 29, 1-17 (1995); He and Tessier-Lavigne, *Cell* 90, 739-751 (1997); Kitsukawa et al., *Neuron* 19, 995-1005 1997; Kolodkin et al., *Cell* 90, 753-762 (1997)).

Our results are the first to show that VEGF$_{165}$R/NP-1 is also expressed in adult tissues, in contrast to the earlier studies that have shown that NP-1 expression in *Xenopus*, chicken and mouse is limited to the developmental and early post-natal stages (Fujisawa et al., *Dev. Neurosci.* 17, 343-349 (1995); Kawakami et al., *J. Neurobiol.* 29, 1-17 (1995); Takagi et al., *Dev. Biol.* 170, 207-222 (1995)). For example, in mice, NP-1 is expressed in the developing nervous system starting in the dorsal root ganglia at day 9 and ceases at day 15 (Kawakami et al., *J. Neurobiol.* 29, 11-17 (1995). Our Northern blot analysis of human adult tissue demonstrates relatively high levels of VEGF$_{165}$R/NP-1 mRNA transcripts in heart, placenta, lung, liver, skeletal muscle, kidney and pancreas. Interestingly, there is very little relative expression in adult brain, consistent with the mouse nervous system expression studies (Kawakami et al., *J. Neurobiol.* 29, 1-17 (1995)). VEGF$_{165}$R/NP-1 is also expressed in a number of cultured non-neuronal cell lines including EC and a variety of tumor-derived cells. A possible function of VEGF$_{165}$R/NP-1 in these cells is to mediate angiogenesis as will be discussed below.

In addition, NP-1 has been identified as a receptor for the collapsin/semaphorin family by expression cloning of a cDNA library obtained from rat E14 spinal cord and dorsal root ganglion (DRG) tissue (He and Tessier-Lavigne. *Cell* 90, 739-751 (1997); Kolodkin et al., *Cell* 90, 753-762 (1997)). The collapsin/semaphorins (collapsin-D-1/Sema III/Sem D) comprise a large family of transmembrane and secreted glycoproteins that function in repulsive growth cone and axon guidance (Kolodkin et al., *Cell* 75, 1389-1399 (1993)). The repulsive effect of sema III for DRG cells was blocked by anti-NP-1 antibodies (He and Tessier-Lavigne, *Cell* 90, 739-751 (1997); Kolodkin et al., *Cell* 90, 753-762 (1997)). The $K_d$ of sema III binding to NP-1, 0.15-3.25×10$^{-10}$ M (He and Tessier-Lavigne, *Cell* 90, 739-751 (1997); Kolodkin et al., *Cell* 90, 753-762 (1997)) is similar to that of VEGF$_{165}$ binding VEGF$_{165}$/NP-1, which is about 3×10$^{-10}$ M. These results indicate that two structurally different ligands with markedly different biological activities, VEGF-induced stimulation of EC migration and proliferation on one hand, and sema III-induced chemorepulsion of neuronal cells, on the other hand, bind to the same receptor and with similar affinity. An interesting question is whether the two ligands bind to the same site on VEGF$_{165}$R/NP-1 or to different sites. VEGF$_{165}$R/NP-1 has five discrete domains in its ectodomain, and it has been suggested that this diversity of protein modules in NP-1 is consistent with the possibility of multiple binding ligands for NP-1 (Takagi et al., *Neuron* 7, 295-307 (1991); Feiner et al., *Neuron* 19 539-545 (1997); He and Tessier-Lavigne, *Cell* 90 739-751 (1997). Preliminary analysis does not indicate any large degree of sequence homology between sema III and VEGF exon 7 which is responsible for VEGF binding to VEGF$_{165}$R/NP-1 (Soker et al., *J. Biol Chem.* 271, 5761-5767 (1996)). However there may be some 3-dimensional structural similarities between the two ligands. Since both neurons and blood vessels display branching and directional migration, the question also arises as to whether VEGF$_{165}$ displays any neuronal guidance activity and whether sema III has any EC growth factor activity. These possibilities have not been examined yet. However, it may be that VEGF requires two receptors, KDR and NP-1 for optimal EC growth factor activity (Soker et al., *J. Biol. Chem.* 272, 31582-31588 (1997)) and that sema III requires NP-1 and an as yet undetermined high affinity receptor for optimal chemorepulsive activity (Feiner et al., *Neuron* 19, 539-545 (1997;) He and Tessier-Lavigne. *Cell* 90, 739-751 (1997): Kitsukawa et al., *Neuron* 19, 995-1005 (1997)), so that the presence of NP-1 alone might not be sufficient for these ligands to display novel biological activities. Future studies will determine whether there are any connections between the mechanisms that regulate neurogenesis and angiogenesis. VEGF$_{165}$R/NP-1 role in angiogenesis VEGF$_{165}$R/NP-1 modulates the binding of VEGF$_{165}$ to KDR, a high affinity RTK that is an important regulator of angiogenesis as evidenced by KDR knock out experiments in mice (Shalaby et al., *Nature* 376, 62-66 (1995). The affinity of KDR for VEGF$_{165}$ is about 50 times greater than for VEGF$_{165}$R/NP-1 (Gitay-Goren et al., *J. Biol. Chem.* 287, 6003-6096 (1992); Waltenberger et al., *J. Biol. Chem.* 269, 26988-26995 (1994)). When VEGF$_{165}$R/NP-1 and KDR are co-expressed, the binding of $^{125}$I-VEGF$_{165}$ to KDR is enhanced by about 4-fold compared to cells expressing KDR alone. The enhanced binding can be demonstrated in stable clones co-expressing VEGF$_{165}$R/NP-1 and KDR (PAE/KDR/NP-1 cells), and also in PAE/KDR cells transfected transiently with VEGF$_{165}$R/NP-1 cDNA where clonal selection does not take place. Conversely, when the binding of $^{125}$I-VEGF$_{165}$ to VEGF$_{165}$R/NP-1 in PAE/KDR/NP-1 cells is inhibited completely by a GST fusion protein containing VEGF exons 7+8 (GST-Ex 7+8), the binding to KDR is inhibited substantially, down to the levels observed in cells expressing KDR alone. The fusion protein binds to VEGF$_{165}$R/NP-1 directly but is incapable of binding to KDR directly (Soker et al., *J. Biol. Chem.* 272, 31582-31588 (1997)). Although, not wishing to be bound by theory, we believe that VEGF$_{165}$ binds to VEGF$_{165}$R/NP-1 via the exon 7-encoded domain and facilitates VEGF$_{165}$ binding to KDR via the exon 4-encoded domain (FIG. 11). VEGF$_{165}$R/NP-1, with its relatively high receptor/cell number, about 0.2-2× 10$^5$ (Gitay-Goren et al., *J. Biol Chem.* 287, 6003-6096 (1992); Soker et al., *J. Biol. Chem.* 271, 5761-5767 (1996)), appears to serve to concentrate VEGF$_{165}$ on the cell surface, thereby providing greater access of VEGF$_{165}$ to KDR. Alternatively, binding to VEGF$_{165}$R/NP-1, VEGF$_{165}$ undergoes a conformational change that enhances its binding to KDR. The end result would be elevated KDR signaling and increased VEGF activity. Although we can demonstrate enhanced binding to KDR to date we have not been able to demonstrate enhanced VEGF mitogenicity for PAE/KDR/NP-1 cells compared to PAE/KDR cells. One reason is that these cell lines do not proliferate readily in response to VEGF as do HUVEC (Waltenberger et al., *J. Biol. Chem.* 269, 26988-26995 (1994). Nevertheless, we have shown that VEGF$_{165}$, which binds to both KDR and VEGF$_{165}$R/NP-1, is a better mitogen for HUVEC than is VEGF$_{121}$, which binds only to KDR (Keyt et al., *J. Biol. Chem.* 271, 5638-5646 (1996b); Soker et al., *J. Biol. Chem.* 272, 31582-31588 (1997). Furthermore, inhibiting VEGF$_{165}$ binding to VEGF$_{165}$R/NP-1 on HUVEC by GST-EX 7+8, inhibits binding to KDR and also inhibits VEGF$_{165}$-induced HUVEC proliferation, down to the level induced by VEGF$_{121}$ (Soker et al., *J. Biol. Chem.* 272, 31582-31588 (1997)). Taken together, these results suggest a role for VEGF$_{165}$R/NP-1 in mediating VEGF$_{165}$, but not VEGF$_{121}$ mitogenic activity. The concept that dual receptors regulate growth factor binding and activity has been previously demonstrated for TGF-β, bFGF and NGF (Lopez-Casillas et al., *Cell* 67, 785-795 (1991); Yayon et al., *Cell* 64, 841-848 (1991; Barbacid, *Curr. Opin. Cell Biol.* 7, 148-155 (1995)).

Another connection between VEGF$_{165}$R/NP-1 and angiogenesis comes from studies in which NP-1 was overexpressed ectopically in transgenic mice (Kitsuskawa et al., *Develop.* 121, 4309-4318 (1995)). NP-1 overexpression resulted in embryonic lethality and the mice died in utero no later than on embryonic day 15.5 and those that survived the best had lower levels of NP-1 expression. Mice overexpressing NP-1 displayed morphologic abnormalities in a limited number of non-neural tissues such as blood vessels, the heart and the limbs. NP-1 was expressed in both the EC and in the mesenchymal cells surrounding the EC. The embryos possessed excess and abnormal capillaries and blood vessels compared to normal counterparts and in some cases dilated blood vessels as well. Some of the chimeric mice showed hemorrhaging, mainly in the head and neck. These results are consistent with the possibility that ectopic overexpression of VEGF$_{165}$R/NP-1 results in inappropriate VEGF$_{165}$ activity, thereby mediating enhanced and/or aberrant angiogenesis. Another piece of evidence for a link between NP-1 and angiogenesis comes from a recent report showing that in mice targeted for disruption of the NP-1 gene, the embryos have severe abnormalities in the peripheral nervous system but that their death in utero at days 10.5-12.5 is most probably due to anomalies in the cardiovascular system (Kitsukawa et al., *Neuron* 19. 995-1005 (1997)). VEGF$_{165}$R/NP-1 is associated with tumor-derived cells The greatest degree of VEGF$_{165}$R/NP-1 expression that we have detected so far occurs in tumor-derived cells such as 231 breast carcinoma cells and PC3 prostate carcinoma cells, far more than occurs in HUVEC. The tumor cells express abundant levels of VEGF$_{165}$R/NP-1 mRNA and about 200,000 VEGF$_{165}$ receptors/cell (Soker et al., *J. Biol. Chem.* 271, 5761-5767 (1996)). On the other hand, these tumor cells do not express KDR or Flt-1 so that VEGF$_{165}$R/NP-1 is the only VEGF receptor associated with these cells.

The tumor cells are therefore useful for testing whether VEGF$_{165}$R/NP-1 is a functional receptor for VEGF$_{165}$ in the absence of a KDR background. To date, we have not been able to show that VEGF$_{165}$R/NP-1 mediates a VEGF$_{165}$ signal in tumor-derived cells as measured by receptor tyrosine phopshorylation. Nevertheless, VEGF$_{165}$ might have an effect on tumor cells by inducing some, as yet undetermined activity such as enhanced survival, differentiation, or motility. A recent report has demonstrated that glioma cells express a 190 kDa protein that binds VEGF$_{165}$ but not VEGF$_{121}$, efficiently (Omura et al., *J. Biol Chem.* 272, 23317-23322 (1997)). No stimulation of tyrosine phosphorylation could be demonstrated upon binding of VEGF$_{165}$ to this receptor. Whether the 190 kDa isoform-specific receptor is related to VEGF$_{165}$R/NP-1 is not known presently.

VEGF$_{165}$R/NP-1 may have a storage and sequestration function for VEGF$_{165}$. One might envision that VEGF$_{165}$ is produced by a tumor cell and binds to VEGF$_{165}$R/NP-1 on that cell via the exon 7-encoded domain (Soker et al., *J. Biol. Chem.* 271, 5761-5767 (1996)). The stored VEGF$_{165}$ could be then released to stimulate tumor angiogenesis in a paracrine manner. Alternatively, VEGF$_{165}$R/NP-1 may mediate a juxtacrine effect in which VEGF$_{165}$ is bound to VEGF$_{165}$R/NP-1 on a tumor cell via the exon 7-encoded domain and is also bound to KDR on a neighboring EC via the exon 4-encoded domain (Keyt et al., *J. Biol. Chem.* 271, 5638-5646 (1996b)). Such a mechanism could result in a more efficient way for tumor cells to attract EC, thereby enhancing tumor angiogenesis.

In summary, we have demonstrated by independent purification and expression cloning methods that the VEGF isoform specific receptor, VEGF$_{165}$R, is identical to NP-1, a cell surface protein previously identified as playing a role in embryonic development of the nervous system and as being a receptor for the collapsins/semaphorins. Furthermore, binding to VEGF$_{165}$R/NP-1 enhances the binding of VEGF$_{165}$ to KDR on EC and tumor cells.

Experimental Rationale

We have discovered that tumor cell neuropilin-1 mediates tumor cell motility and thereby metastasis. In a Boyden chamber motility assay, VEGF$_{165}$ (50 ng/ml) stimulates 231 breast carcinoma cell motility in a dose-response manner, with a maximal 2-fold stimulation (FIG. 15A). On the other hand, VEGF$_{121}$, has no effect on motility of these cells (FIG. 15B). Since 231 cells do not express KDR or Flt-1, these results suggest that tumor cells are directly responsive to VEGF$_{165}$ and that VEGF$_{165}$ might signal tumor cells via neuropilin-1. Possible candidates for mediating VEGF$_{165}$-induced motility of carcinoma cells are PI3-kinase (PI3-K) (Carpenter, et al. (1996) *Curr. Opin. Cell Biol.* 8: 153-158.). Since 231 cells do not express KDR or Flt-1, these results suggest that tumor cells are directly responsive to VEGF$_{165}$ and that VEGF$_{165}$ might signal tumor cells via neuropilin-1.

The other type of evidence is that neuropilin-1 expression might be associated with tumor cell motility. We have analyzed two variants of Dunning rat prostate carcinoma cells, AT2.1 cells, which are of low motility and low metastatic potential, and AT3.1 cells, which are highly motile, and metastatic. Cross-linking and Northern blot analysis show that AT3.1 cells express abundant neuropilin-1, capable of binding VEGF$_{165}$, while AT2.1 cells don't express neuropilin-1 (FIG. 16). Immunostaining of tumor sections confirms the expression of neuropilin-1 in AT3.1, but not AT2.1 tumors. Furthermore, the immunostaining shows that in subcutaneous AT3.1 and PC3 tumors, the tumor cells expressing neuropilin-1 are found preferentially at the invading front of the tumor/dermis boundary. To determine more directly whether neuropilin-1 expression is correlated with enhanced motility, neuropilin-1 was overexpressed in AT2.1 cells (FIG. 17). Three stable clones of AT2.1 cells overexpressing neuropilin-1 had enhanced motility in the Boyden chamber assay. These results indicate that expression of neuropilin-1 in AT2.1 cells enhances their motility. Taken together, it appears that neuropilin-1 expression on tumor cells is associated with the motile, metastatic phenotype.

EXAMPLE 2

Construction of sNP-1 and sNP-2

The cDNAs encoding the soluble forms of neuropilin-1 and neuropilin-2 were cloned from an oligo dT-primed cDNA library which was synthesized from PC3 cell mRNA.

Soluble Neuropilin-1 (sNP-1) cDNA Cloning:

The sNP-1 cDNA deviates from the full length NP-1 cDNA between the b2 and c domains after amino acid 641, at the position of an exon-exon boundary. The 3' end of the sNP-1 clone possesses 28 bp of intron sequence, encoding three novel amino acids and a translation stop codon.

An oligonucleotide (GAAGTATACGGTTGCAAGATA SEQ ID NO: 16) designed from within the b1 domain was used in 3' RACE (rapid amplification of cDNA ends) to clone the 3' end of the sNP-1 cDNA. The full length sNP-1 cDNA was subsequently cloned from the PC3 library by RT-PCR using primers at the 5' (GCGTTCCTCTCGGATC-CAGGC SEQ ID NO:17) and 3' (CAGGTAT-CAAATAAAATAC SEQ ID NO:18) ends of the sNP-1 open reading frame (ORF). The sNP-1 cDNA was tagged with His and c-myc domains (amino acids HHHHHHQQKLISQQNL SEQ ID NO:19) in the N-terminus of the a1 domain between amino acids 43 and 44 of sNP-1. The complete tagged sNP-1 cDNA was subcloned into the pcDNA3.1 mammalian expression plasmid. The nucleotide and amino acid sequence of the sNP-1 are set forth in the sequence listing as SEQ ID NOS:5 and 6, respectively.

Soluble Neuropilin-2 (sNP-2) cDNA Cloning:

The sNP-2 cDNA deviates from the full length NP-2 cDNA within the b2 domain after amino acid 547, at the position of an exon-exon boundary. The 3' end of the sNP-2 clone possesses 146 bp of intron sequence encoding 8 novel amino acids and a translation stop codon.

An oligonucleotide GGCTGCCGGGTAACAGATGC SEQ ID NO:20) designed from within the b1 domain was used in 3' RACE (rapid amplification of cDNA ends) to clone the 3' end of the sNP-2 cDNA. The full length sNP-2 cDNA was subsequently cloned from the PC3 library by RT-PCR using primers at the 5' (ATGGATATGTTTC-CTCTC SEQ ID NO:21) and 3' (GTTCTTGGAGGCCTCT-GTAA SEQ ID NO:22) ends of the sNP-2 open reading frame (ORF). The sNP-2 cDNA was tagged with His and c-myc domains (amino acids HHHHHHQQKLISQQNL SEQ ID NO:19) in the N-terminus of the a1 domain between amino acids 31 and 32 of sNP-2. The complete tagged sNP-2 cDNA was subcloned into the pcDNA3.1 mammalian expression plasmid. The nucleotide and amino acid sequence of sNP-2 are set forth in the sequence listing as SEQ ID NOS:7 and 8 respectively.

EXAMPLE 3

Preparation of Soluble NP-1 (Domains AB and C)
1. The Sequence of NP-1 between the BamHI site (base 100) and the XbaI site (base 4687) was subcloned between the BamHI and XbaI site in pBluscript II KS (+) (Stratagene, La Jola Calif.) to yield pBS-NP1.
2. PCR was performed on NP-1 sequence with the following primers:
Primer 1 (Forward): NdeI site (bold and underlined) at NP-1 base 2200) GGAATTC<u>CATATG</u>GTTTTAACTGTGAA (SEQ ID NO:23)
Primer 2 (Reverse): Outside the transmembrane membrane domain at NP-1 base 2823 including 6 histidine (his-tag) and an XbaI site (bold and underlined) GC<u>TCTAGA</u>TTAATGATGATGATGATGATGGGTCTTCA-ACACATTGCC (SEQ ID NO:24) The PCR DNA product (approx. 600 bp) was digested with NdeI and XbaI and purified from an agarose gel. The plasmid pBS-NP1 was digested with NdeI and XbaI and the large fragment containing the extracellular portion of NP-1 was purified from an agarose gel and was served as the vector. Ligation of the above PCR product and the vector was performed and the resulting plasmid was named pBS-sNPhis.
3. The plasmid pBS-sNPhis was digested with BamHI and XbaI and the fragment containing the extracellular part of NP-1 (including the his-tag) was subcloned in the BamHI and XbaI sites of pCPhygro (described in the above examples and in Soker et al., *Cell* 92:735 (1998) to yield pCPhyg-sNPhis.
4. The plasmid pCPhyg-sNPhis was transfected to CHO cells and hygromycin resistant clones were selected and tested for expression of soluble NP-1, soluble NP-1 was purified from the medium by using nickel Sepharose beads.
5. Clones were tested for sNP-1 expression in the following manner. Medium was conditioned for 24 hours and the conditioned medium was incubated with the lectin ConA for 24 hours. ConA bound material was analyzed by SDS-PAGE and Western blotting using an antibody against the A domain of neuropilin-1.

The references cited throughout the specification are incorporated herein by reference.

The present invention has been described with reference to specific embodiments. However, this application is intended to cover those changes and substitutions which may be made by those skilled in the art without departing from the spirit and the scope of the appended claims.

---

What is claimed:

1. A method of inhibiting endothelial cell proliferation, comprising contacting endothelial cells with a soluble neuropilin consisting of the amino acid sequence of SEQ ID NO:6.

2. A method for inhibiting angiogenesis of a solid tumor, comprising administering a soluble neuropilin consisting of the amino acid sequence of SEQ ID NO: 6.

* * * * *

SEQUENCE LISTING

<160> NUMBER OF SEQ ID NOS: 24

<210> SEQ ID NO 1
<211> LENGTH: 5653
<212> TYPE: DNA
<213> ORGANISM: human

<400> SEQUENCE: 1

```
aagggagagg aagccggagc taaatgacag gatgcaggcg acttgagaca caaaaagaga      60
agcgttcctc tcggatccag gcattgcctc gctgctttct tttctccaag acgggctgag     120
gattgtacag ctctaggcgg agttggggct cttcggatcg cttagattct cctctttgct     180
gcatttcccc ccacgtcctc gttctcccgc gtctgcctgc ggacccggag aagggagaat     240 ggagagggg ctgccgctcc tctgcgccgt gctcgccctc gtcctcgccc cggccggcgc      300
ttttcgcaac gataaatgtg gcgatactat aaaaattgaa agcccgggt accttacatc      360 tcctggttat cctcattctt atcacccaag tgaaaaatgc gaatggctga ttcaggctcc     420
ggacccatac cagagaatta tgatcaactt caaccctcac ttcgatttgg aggacagaga     480
ctgcaagtat gactacgtgg aagtgttcga tggagaaaat gaaaatggac attttaggg     540 aaagttctgt ggaaagatag cccctcctcc tgttgtgtct tcagggccat ttcttttat      600 caaatttgtc tctgactacg aaacacatgg tgcaggattt tccatacgtt atgaaaattt      660
caagagaggt cctgaatgtt cccagaacta cacaacacct agtggagtga taaagtcccc     720
cggattccct gaaaaatatc ccaacagcct tgaatgcact tatattgtct ttgcgccaaa     780
gatgtcagag attatcctgg aatttgaaag ctttgacctg gagcctgact caaatcctcc     840 agggggatg ttctgtcgct acgaccggct agaaatctgg gatggattcc ctgatgttgg     900
ccctcacatt gggcgttact gtggacagaa acaccaggt cgaatccgat cctcatcggg      960 cattctctc atggtttttt acaccgacag cgcgatagca aaagaaggtt tctcagcaaa     1020
ctacagtgtc ttgcagagca gtgtctcaga agattcaaa tgtatggaag ctctgggcat     1080
```

```
ggaatcagga gaaattcatt ctgaccagat cacagcttct tcccagtata gcaccaactg   1140
gtctgcagag cgctcccgcc tgaactaccc tgagaatggg tggactcccg gagaggattc   1200
ctaccgagag tggatacagg tagacttggg ccttctgcgc tttgtcacgg ctgtcgggac   1260
acagggcgcc atttcaaaag aaaccaagaa gaaatattat gtcaagactt acaagatcga   1320
cgttagctcc aacggggaag actggatcac cataaaagaa ggaaacaaac ctgttctctt   1380
tcagggaaac accaacccca cagatgttgt ggttgcagta ttccccaaac cactgataac   1440
tcgatttgtc cgaatcaagc ctgcaacttg ggaaactggc atatctatga gatttgaagt   1500
atacggttgc aagataacag attatccttg ctctggaatg ttgggtatgg tgtctggact   1560
tatttctgac tcccagatca catcatccaa ccaaggggac agaaactgga tgcctgaaaa   1620
catccgcctg gtaaccagtc gctctggctg gcacttcca cccgcacctc attcctacat    1680
caatgagtgg ctccaaatag acctggggga ggagaagatc gtgagggca tcatcattca    1740 gggtgggaag caccgagaga caaggtgtt catgaggaag ttcaagatcg ggtacagcaa    1800
caacggctcg gactggaaga tgatcatgga tgacagcaaa cgcaaggcga agtcttttga    1860
gggcaacaac aactatgata cacctgagct gcggactttt ccagctctct ccacgcgatt    1920
catcaggatc taccccgaga gagccactca tggcggactg gggctcagaa tggagctgct    1980
gggctgtgaa gtggaagccc ctacagctgg accgaccact cccaacggga acttggtgga    2040
tgaatgtgat gacgaccagg ccaactgcca cagtggaaca ggtgatgact ccagctcac    2100 aggtggcacc actgtgctgg ccacagaaaa gcccacggtc atagacagca ccatacaatc    2160
agagtttcca acatatggtt ttaactgtga atttggctgg ggctctcaca agaccttctg    2220
ccactgggaa catgacaatc acgtgcagct caagtgagt gtgttgacca gcaagacggg    2280
acccattcag gatcacacag gagatggcaa cttcatctat tcccaagctg acgaaaatca    2340
gaagggcaaa gtggctcgcc tggtgagccc tgtggttat tcccagaact ctgcccactg    2400
catgaccttc tggtatcaca tgtctgggtc ccacgtcggc acactcaggg tcaaactgcg    2460
ctaccagaag ccagaggagt acgatacgct ggtctggatg gccattggac accaaggtga    2520
ccactggaag gaagggcgtg tcttgctcca caagtctctg aaactttatc aggtgatttt    2580
cgagggcgaa atcggaaaag gaaaccttgg tgggattgct gtggatgaca ttagtattaa    2640
caaccacatt tcacaagaag attgtgcaaa accagcagac ctggataaaa agaacccaga    2700
aattaaaatt gatgaaacag ggagcacgcc aggatacgaa ggtgaaggag aaggtgacaa    2760
gaacatctcc aggaagccag gcaatgtgtt gaagacctta gatcccatcc tcatcaccat    2820
catagccatg agtgccctgg gggtcctcct ggggctgtc tgtggggtcg tgctgtactg    2880
tgcctgttgg cataatggga tgtcagaaag aaacttgtct gccctggaga actataactt    2940
tgaacttgtg gatggtgtga gttgaaaaa agacaaactg aatacacaga gtacttattc    3000
ggaggcatga aggcagacag agatgaaaag acagtcaaag gacggaagtg aaggacggg    3060 agtgagctgg ggagctgttg atctttcact atacaggctg ggaagtgtgt tgatgaccac    3120
tgagccaggc ttttctcagg agcttcaatg agtatggccg acagacatgg acaaggagct    3180
gtgttcacca tcggactcat gtgcagtcag cttttttcct gttggttca tttgaataat    3240 cagatgctgg tgttgagacc aagtatgatt gacataatca ttcatttcga cccctcctgc    3300
ccctctctct ctctctcctc tcccctttgt ggattctttt tggaaactga gcgaaatcca    3360
agatgctggg accaagcgta ttccgtgtgg ccctttggat ggacatgcta cctgaaaccc    3420
```

-continued

```
agtgcccaga atatactaga atcaccgcat ttcagtggac tcctgaagtt gtacttgtgt    3480
ataattgccc gcgtcgtgca taggcaaaga aggattaggc tgttttcttt ttaaagtact    3540
gtagcctcag tactggtgta gtgtgtcagc tctgtttacg aagcaatact gtccagtttt    3600
cttgctgttt ttccggtgtt gtactaaacc tcgtgcttgt gaactccata cagaaaacgg    3660
tgccatccct gaacacggct ggccactggg tatactgctg acaaccgcaa caacaaaaac    3720
acaaatcctt ggcactggct agtctatgtc ctctcaagtg cctttttgtt tgtactggtt    3780
cattgtgtta cattaacgac ccactctgct tcttgctggt gaaagccctg ctctttaatc    3840
aaactctggt ggcccactga ctaagaagaa agtttatttt cgtgtgagat gccagcccct    3900
ccgggcaggc aagggctctg aagatttggc aacgtggctt aattgttctg cttttttctgt   3960
agttcaattt catgtttctt gacccttttg tataaagcta caatattctc tcttattgtt    4020
cttcatatg gaatgtattt tcaaatgtaa actctcttct ctttctctct cctatctctc     4080
tgtctttttt ctctcttaga attggaggat ttgccattgt ccaggaaaga aacttgcagc    4140
tttaacctgc tgggaatggc aaacgatttt actagacttt atgtttaaaa ataaataaat    4200
aagggaaatt cctaactttg ccctccaaag tctaactttg gttttcttgt taactggtta    4260
aagtgacagt atcttttttc cttatctatt ctattcaaaa tgacctttga tagaaatgtt    4320
ggcatttagt agaaatagtg ataagttgag gaaagaaata atacaaattg gctttcaagt    4380
gagacccaaa ggaagaactg gataaaatct tccaaatcca aaagcatgag atttttctat    4440
ccaaatatgc aaaaatgacc caagagaact ttcttatttt gctactgagt cacacaaggg    4500
aagtggaagg aagaacagtt aatttaagaa tgaaactata aatcctgatg cctgggggtc    4560
aagtattta agataagagg gggaaaaaca cataaagtca aacaaatgtt ttaaaaattc      4620
ataacagcaa ccttgaaaaa atagacttaa atgaatgctt ctagaaactt ccagcggctc    4680
acaaagaata agcctgcctt agggctggca acatctaagc ctctaacagc cagggaagc     4740
aaatatctta ccaggcagcc tatgaattaa cccaaagaag ctttggttgg ttttggtgga    4800
ttttatcat gccatgttgg acatgagatt ttttagatct tccttcccca cattgctaga    4860
cgtctcactc aaagacattt gttgggagtc acatttgcat catagacgag acagtccatt    4920
catcttagtt aaattggatt gagaatgcct tttgtttcca ggaaaatatt gatcaccatg    4980
aaagaagaat agttttttgt ccccagagac attcatttag ttgatataat cctaccagaa    5040
ggaaagcact aagaaacact cgtttgttgt ttttaaaggc aacagactta aagttgtcct    5100
cagccaagga aaaatgatac tgcaacttta aaatttaaag tatcttgcac tgataaatat    5160
atttaaaaat tatatgtttta taagttatt aatttgtaaa ggcagtgtta caaaatgttc     5220
agtttatatt gttttagatt gttttgtaat ttttaaaggt gtaaataac atataaatat     5280
atttaaaaat tatatgtttta taagttatt aatttgtaaa ggcagtgtta caaaatgttc     5340
agtttatatt gttttagatt gttttgtaat ttttaaaggt gtaaataac atattttttc     5400
tttatggaaa tctataaaac tttctgtagt aaaatgtttt cattttactg gtatattatt    5460
gcttcatgtt ttgtaccatc ataagatttt gtgcagattt ttttacaga aattattatt     5520
ttctatgaca atatgacact tgtaaattgt tgtttcaaaa tgaacagcga agccttaact    5580
ttaaatgaca tttgtattct cagacactga gtagcataaa aaccacatga actgaactgt    5640
aacttaaatt ctt                                                       5653
```

<210> SEQ ID NO 2
<211> LENGTH: 923

```
<212> TYPE: PRT
<213> ORGANISM: human

<400> SEQUENCE: 2

Met Glu Arg Gly Leu Pro Leu Leu Cys Ala Val Leu Ala Leu Val Leu
 1               5                  10                  15

Ala Pro Ala Gly Ala Phe Arg Asn Asp Lys Cys Gly Asp Thr Ile Lys
            20                  25                  30

Ile Glu Ser Pro Gly Tyr Leu Thr Ser Pro Gly Tyr Pro His Ser Tyr
        35                  40                  45

His Pro Ser Glu Lys Cys Glu Trp Leu Ile Gln Ala Pro Asp Pro Tyr
    50                  55                  60

Gln Arg Ile Met Ile Asn Phe Asn Pro His Phe Asp Leu Glu Asp Arg
65                  70                  75                  80

Asp Cys Lys Tyr Asp Tyr Val Glu Val Phe Asp Gly Glu Asn Glu Asn
                85                  90                  95

Gly His Phe Arg Gly Lys Phe Cys Gly Lys Ile Ala Pro Pro Pro Val
            100                 105                 110

Val Ser Ser Gly Pro Phe Leu Phe Ile Lys Phe Val Ser Asp Tyr Glu
        115                 120                 125

Thr His Gly Ala Gly Phe Ser Ile Arg Tyr Glu Ile Phe Lys Arg Gly
    130                 135                 140

Pro Glu Cys Ser Gln Asn Tyr Thr Thr Pro Ser Gly Val Ile Lys Ser
145                 150                 155                 160

Pro Gly Phe Pro Glu Lys Tyr Pro Asn Ser Leu Glu Cys Thr Tyr Ile
                165                 170                 175

Val Phe Ala Pro Lys Met Ser Glu Ile Ile Leu Glu Phe Glu Ser Phe
            180                 185                 190

Asp Leu Glu Pro Asp Ser Asn Pro Pro Gly Gly Met Phe Cys Arg Tyr
        195                 200                 205

Asp Arg Leu Glu Ile Trp Asp Gly Phe Pro Asp Val Gly Pro His Ile
    210                 215                 220

Gly Arg Tyr Cys Gly Gln Lys Thr Pro Gly Arg Ile Arg Ser Ser Ser
225                 230                 235                 240

Gly Ile Leu Ser Met Val Phe Tyr Thr Asp Ser Ala Ile Ala Lys Glu
                245                 250                 255

Gly Phe Ser Ala Asn Tyr Ser Val Leu Gln Ser Ser Val Ser Glu Asp
            260                 265                 270

Phe Lys Cys Met Glu Ala Leu Gly Met Glu Ser Gly Glu Ile His Ser
        275                 280                 285

Asp Gln Ile Thr Ala Ser Ser Gln Tyr Ser Thr Asn Trp Ser Ala Glu
    290                 295                 300

Arg Ser Arg Leu Asn Tyr Pro Glu Asn Gly Trp Thr Pro Gly Glu Asp
305                 310                 315                 320

Ser Tyr Arg Glu Trp Ile Gln Val Asp Leu Gly Leu Leu Arg Phe Val
                325                 330                 335

Thr Ala Val Gly Thr Gln Gly Ala Ile Ser Lys Glu Thr Lys Lys Lys
            340                 345                 350

Tyr Tyr Val Lys Thr Tyr Lys Ile Asp Val Ser Ser Asn Gly Glu Asp
        355                 360                 365

Trp Ile Thr Ile Lys Glu Gly Asn Lys Pro Val Leu Phe Gln Gly Asn
    370                 375                 380

Thr Asn Pro Thr Asp Val Val Val Ala Val Phe Pro Lys Pro Leu Ile
385                 390                 395                 400
```

```
Thr Arg Phe Val Arg Ile Lys Pro Ala Thr Trp Glu Thr Gly Ile Ser
                405                 410                 415
Met Arg Phe Glu Val Tyr Gly Cys Lys Ile Thr Asp Tyr Pro Cys Ser
                420                 425                 430
Gly Met Leu Gly Met Val Ser Gly Leu Ile Ser Asp Ser Gln Ile Thr
                435                 440                 445
Ser Ser Asn Gln Gly Asp Arg Asn Trp Met Pro Glu Asn Ile Arg Leu
450                 455                 460
Val Thr Ser Arg Ser Gly Trp Ala Leu Pro Pro Ala Pro His Ser Tyr
465                 470                 475                 480
Ile Asn Glu Trp Leu Gln Ile Asp Leu Gly Glu Lys Ile Val Arg
                485                 490                 495
Gly Ile Ile Ile Gln Gly Gly Lys His Arg Glu Asn Lys Val Phe Met
                500                 505                 510
Arg Lys Phe Lys Ile Gly Tyr Ser Asn Asn Gly Ser Asp Trp Lys Met
                515                 520                 525
Ile Met Asp Asp Ser Lys Arg Lys Ala Lys Ser Phe Glu Gly Asn Asn
530                 535                 540
Asn Tyr Asp Thr Pro Glu Leu Arg Thr Phe Pro Ala Leu Ser Thr Arg
545                 550                 555                 560
Phe Ile Arg Ile Tyr Pro Glu Arg Ala Thr His Gly Gly Leu Gly Leu
                565                 570                 575
Arg Met Glu Leu Leu Gly Cys Glu Val Glu Ala Pro Thr Ala Gly Pro
                580                 585                 590
Thr Thr Pro Asn Gly Asn Leu Val Asp Glu Cys Asp Asp Gln Ala
                595                 600                 605
Asn Cys His Ser Gly Thr Gly Asp Asp Phe Gln Leu Thr Gly Gly Thr
                610                 615                 620
Thr Val Leu Ala Thr Glu Lys Pro Thr Val Ile Asp Ser Thr Ile Gln
625                 630                 635                 640
Ser Glu Phe Pro Thr Tyr Gly Phe Asn Cys Glu Phe Gly Trp Gly Ser
                645                 650                 655
His Lys Thr Phe Cys His Trp Glu His Asp Asn His Val Gln Leu Lys
                660                 665                 670
Trp Ser Val Leu Thr Ser Lys Thr Gly Pro Ile Gln Asp His Thr Gly
                675                 680                 685
Asp Gly Asn Phe Ile Tyr Ser Gln Ala Asp Glu Asn Gln Lys Gly Lys
                690                 695                 700
Val Ala Arg Leu Val Ser Pro Val Val Tyr Ser Gln Asn Ser Ala His
705                 710                 715                 720
Cys Met Thr Phe Trp Tyr His Met Ser Gly Ser His Val Gly Thr Leu
                725                 730                 735
Arg Val Lys Leu Arg Tyr Gln Lys Pro Glu Glu Tyr Asp Gln Leu Val
                740                 745                 750
Trp Met Ala Ile Gly His Gln Gly Asp His Trp Lys Glu Gly Arg Val
                755                 760                 765
Leu Leu His Lys Ser Leu Lys Leu Tyr Gln Val Ile Phe Glu Gly Glu
770                 775                 780
Ile Gly Lys Gly Asn Leu Gly Gly Ile Ala Val Asp Asp Ile Ser Ile
785                 790                 795                 800
Asn Asn His Ile Ser Gln Glu Asp Cys Ala Lys Pro Ala Asp Leu Asp
                805                 810                 815
```

-continued

| | | | | | | | | | | | |
|---|---|---|---|---|---|---|---|---|---|---|---|
| Lys | Lys | Asn | Pro | Glu | Ile | Lys | Ile | Asp | Glu | Thr | Gly | Ser | Thr | Pro | Gly |
| | | | 820 | | | | 825 | | | | 830 | | | | |
| Tyr | Glu | Gly | Glu | Gly | Glu | Gly | Asp | Lys | Asn | Ile | Ser | Arg | Lys | Pro | Gly |
| | | 835 | | | | | 840 | | | | 845 | | | | |
| Asn | Val | Leu | Lys | Thr | Leu | Asp | Pro | Ile | Leu | Ile | Thr | Ile | Ile | Ala | Met |
| | 850 | | | | | 855 | | | | | 860 | | | | |
| Ser | Ala | Leu | Gly | Val | Leu | Leu | Gly | Ala | Val | Cys | Gly | Val | Val | Leu | Tyr |
| 865 | | | | 870 | | | | 875 | | | | | 880 | | |
| Cys | Ala | Cys | Trp | His | Asn | Gly | Met | Ser | Glu | Arg | Asn | Leu | Ser | Ala | Leu |
| | | | 885 | | | | 890 | | | | | 895 | | | |
| Glu | Asn | Tyr | Asn | Phe | Glu | Leu | Val | Asp | Gly | Val | Lys | Leu | Lys | Lys | Asp |
| | | 900 | | | | | 905 | | | | 910 | | | | |
| Lys | Leu | Asn | Thr | Gln | Ser | Thr | Tyr | Ser | Glu | Ala | | | | | |
| | 915 | | | | | 920 | | | | | | | | | |

<210> SEQ ID NO 3
<211> LENGTH: 3404
<212> TYPE: DNA
<213> ORGANISM: human

<400> SEQUENCE: 3

```
gaattcggca cgaggggaaa ataaaagaga gaaaaacaca aagatttaaa caagaaacct    60
acgaacccag ctctggaaag agccaccttc tccaaaatgg atatgtttcc tctcacctgg   120
gttttcttag ccctctactt ttcaagacac caagtgagag ccaaccagac ccaccgtgc    180
ggaggtcgtt tgaattccaa agatgctggc tatatcacct ctcccggtta cccccaggac   240
taccctccc accagaactg cgagtggatt gtttacgccc cgaacccaa ccagaagatt     300
gtcctcaact tcaaccctca ctttgaaatc gagaagcacg actgcaagta tgactttatc   360
gagattcggg atggggacag tgaatccgca gacctcctgg gcaaacactg tgggaacatc   420
gccccgccca ccatcatctc ctcgggctcc atgctctaca tcaagttcac ctccgactac   480
gcccggcagg gggcaggctt ctctctgcgc tacgagatct tcaagacagg ctctgaagat   540
tgctcaaaaa acttcacaag ccccaacggg accatcgaat ctcctgggtt tcctgagaag   600
tatccacaca acttggactg cacctttacc atcctggcca aacccaagat ggagatcatc   660
ctgcagttcc tgatctttga cctggagcat gacccctttgc aggtgggaga ggggactgc   720
aagtacgatt ggctggacat ctgggatggc attccacatg ttggccccct gattggcaag   780
tactgtggga ccaaaacacc ctctgaactt cgttcatcga cggggatcct ctccctgacc   840
tttcacacgg acatggcggt ggccaaggat ggcttctctg cgcgttacta cctggtccac   900
caagagccac tagagaactt tcagtgcaat gttcctctgg gcatggagtc tggccggatt   960
gctaatgaac agatcagtgc ctcatctacc tactctgatg ggaggtggac ccctcaacaa  1020
agccggctcc atggtgatga caatggctgg acccccaact tggattccaa caaggagtat  1080
ctccaggtgg acctgcgctt tttaaccatg ctcacggcca tcgcaacaca gggagcgatt  1140
tccagggaaa cacagaatgg ctactacgtc aaatcctaca agctggaagt cagcactaat  1200
ggagaggact ggatggtgta ccggcatggc aaaaaccaca aggtatttca agccaacaac  1260
gatgcaactg aggtggttct gaacaagctc acgctccac tgctgacaag gtttgttaga   1320
atccgccctc agacctggca ctcaggtatc gccctccggc tggagctctt cggctgccgg  1380
gtcacagatg ctccctgctc caacatgctg gggatgctct caggcctcat tgcagactcc  1440
cagatctccg cctcttccac ccaggaatac ctctggagcc ccagtgcagc ccgcctggtc  1500
```

-continued

```
agcagccgct cgggctggtt ccctcgaatc cctcaggccc agcccggtga ggagtggctt    1560
caggtagatc tgggaacacc caagacagtg aaaggtgtca tcatccaggg agcccgcgga    1620
ggagacagta tcactgctgt ggaagccaga gcatttgtgc gcaagttcaa agtctcctac    1680
agcctaaacg gcaaggactg ggaatacatt caggacccca ggacccagca gccaaagctg    1740
ttcgaaggga acatgcacta tgacacccct gacatccgaa ggtttgaccc cattccggca    1800
cagtatgtgc gggtataccc ggagaggtgg tcgccggcgg ggattgggat gcggctggag    1860
gtgctgggct gtgactggac agactccaag cccacggtag agacgctggg acccactgtg    1920
aagagcgaag agacaaccac cccctacccc accgaagagg aggccacaga gtgtggggag    1980
aactgcagct ttgaggatga caaagatttg cagctcccct cgggattcaa ttgcaacttc    2040
gatttcctcg aggagccctg tgttggatg tatgaccatg ccaagtggct ccggaccacc    2100
tgggccagca gctccagccc aaacgaccgg acgtttccag atgacaggaa tttcttgcgg    2160
ctgcagagtg acagccagag agagggccag tatgcccggc tcatcagccc ccctgtccac    2220
ctgccccgaa gccggtgtg catggagttc cagtaccagg ccacgggcgg ccgcggggtg    2280
gcgctgcagg tggtgcggga agccagccag gagagcaagt gctgtgggt catccgtgag    2340 gaccagggcg gcgagtggaa gcacgggcgg atcatcctgc ccagctacga catggagtac    2400
cagattgtgt cgagggagt gatagggaaa ggacgttccg gagagattgc cattgatgac    2460
attcggataa gcactgatgt cccactggag aactgcatgg aacccatctc ggcttttgca    2520
ggtgagaatt ttaaagtgga catcccagaa atacatgaga gagaaggata tgaagatgaa    2580
attgatgatg aatacgaggt ggactggagc aattcttctt ctgcaacctc agggtctggc    2640
gccccctcga ccgacaaaga aaagagctgg ctgtacaccc tggatcccat cctcatcacc    2700
atcatcgcca tgagctcact gggcgtcctc ctgggggcca cctgtgcagg cctcctgctc    2760
tactgcacct gttcctactc gggcctgagc tcccgaagct gcaccacact ggagaactac    2820
aacttcgagc tctacgatgg ccttaagcac aaggtcaaga tgaaccacca aaagtgctgc    2880
tccgaggcat gacggattgc acctgaatcc tatctgacgt tcattccag caagaggggc    2940 tggggaagat tacatttttt tttccttttgg aaactgaatg ccataatctc gatcaaaccg    3000
atccagaata ccgaaggtat ggacaggaca gaaaagcgag tcgcaggagg aagggagatg    3060
cagccgcaca ggggatgatt accctcctag gaccgcggtg gctaagtcat tgcaggaacg    3120
gggctgtgtt ctctgctggg acaaaacagg agctcatctc tttggggtca cagttctatt    3180
ttgtttgtga gtttgtatta ttattattat tattattatt atatttttatt tctttggtct    3240 gtgagcaact caaagaggca gaagaggaga atgacttttc cagaatagaa gtggagcagt    3300
gatcattatt ctccgctttc tctttctaat caacacttga aaagcaaagt gtcttttcag    3360
cctttccatc tttacaaata aaactcaaaa agctgtccca gctt                    3404
```

<210> SEQ ID NO 4
<211> LENGTH: 931
<212> TYPE: PRT
<213> ORGANISM: human

<400> SEQUENCE: 4

```
Met Asp Met Phe Pro Leu Thr Trp Val Phe Leu Ala Leu Tyr Phe Ser
 1               5                  10                  15

Arg His Gln Val Arg Gly Gln Pro Asp Pro Pro Cys Gly Gly Arg Leu
                20                  25                  30

Asn Ser Lys Asp Ala Gly Tyr Ile Thr Ser Pro Gly Tyr Pro Gln Asp
```

-continued

```
                35                  40                  45
Tyr Pro Ser His Gln Asn Cys Glu Trp Ile Val Tyr Ala Pro Glu Pro
             50                  55                  60
Asn Gln Lys Ile Val Leu Asn Phe Asn Pro His Phe Glu Ile Glu Lys
 65                  70                  75                  80
His Asp Cys Lys Tyr Asp Phe Ile Glu Ile Arg Asp Gly Asp Ser Glu
                 85                  90                  95
Ser Ala Asp Leu Leu Gly Lys His Cys Gly Asn Ile Ala Pro Pro Thr
                100                 105                 110
Ile Ile Ser Ser Gly Ser Met Leu Tyr Ile Lys Phe Thr Ser Asp Tyr
            115                 120                 125
Ala Arg Gln Gly Ala Gly Phe Ser Leu Arg Tyr Glu Ile Phe Lys Thr
        130                 135                 140
Gly Ser Glu Asp Cys Ser Lys Asn Phe Thr Ser Pro Asn Gly Thr Ile
145                 150                 155                 160
Glu Ser Pro Gly Phe Pro Glu Lys Tyr Pro His Asn Leu Asp Cys Thr
                165                 170                 175
Phe Thr Ile Leu Ala Lys Pro Lys Met Glu Ile Ile Leu Gln Phe Leu
            180                 185                 190
Ile Phe Asp Leu Glu His Asp Pro Leu Gln Val Gly Glu Gly Asp Cys
        195                 200                 205
Lys Tyr Asp Trp Leu Asp Ile Trp Asp Gly Ile Pro His Val Gly Pro
    210                 215                 220
Leu Ile Gly Lys Tyr Cys Gly Thr Lys Thr Pro Ser Glu Leu Arg Ser
225                 230                 235                 240
Ser Thr Gly Ile Leu Ser Leu Thr Phe His Thr Asp Met Ala Val Ala
                245                 250                 255
Lys Asp Gly Phe Ser Ala Arg Tyr Tyr Leu Val His Gln Glu Pro Leu
            260                 265                 270
Glu Asn Phe Gln Cys Asn Val Pro Leu Gly Met Glu Ser Gly Arg Ile
        275                 280                 285
Ala Asn Glu Gln Ile Ser Ala Ser Ser Thr Tyr Ser Asp Gly Arg Trp
    290                 295                 300
Thr Pro Gln Gln Ser Arg Leu His Gly Asp Asp Asn Gly Trp Thr Pro
305                 310                 315                 320
Asn Leu Asp Ser Asn Lys Glu Tyr Leu Gln Val Asp Leu Arg Phe Leu
                325                 330                 335
Thr Met Leu Thr Ala Ile Ala Thr Gln Gly Ala Ile Ser Arg Glu Thr
            340                 345                 350
Gln Asn Gly Tyr Tyr Val Lys Ser Tyr Lys Leu Glu Val Ser Thr Asn
        355                 360                 365
Gly Glu Asp Trp Met Val Tyr Arg His Gly Lys Asn His Lys Val Phe
    370                 375                 380
Gln Ala Asn Asn Asp Ala Thr Glu Val Val Leu Asn Lys Leu His Ala
385                 390                 395                 400
Pro Leu Leu Thr Arg Phe Val Arg Ile Arg Pro Gln Thr Trp His Ser
                405                 410                 415
Gly Ile Ala Leu Arg Leu Glu Leu Phe Gly Cys Arg Val Thr Asp Ala
            420                 425                 430
Pro Cys Ser Asn Met Leu Gly Met Leu Ser Gly Leu Ile Ala Asp Ser
        435                 440                 445
Gln Ile Ser Ala Ser Ser Thr Gln Glu Tyr Leu Trp Ser Pro Ser Ala
    450                 455                 460
```

-continued

```
Ala Arg Leu Val Ser Ser Arg Ser Gly Trp Phe Pro Arg Ile Pro Gln
465                 470                 475                 480

Ala Gln Pro Gly Glu Glu Trp Leu Gln Val Asp Leu Gly Thr Pro Lys
                485                 490                 495

Thr Val Lys Gly Val Ile Ile Gln Gly Ala Arg Gly Gly Asp Ser Ile
            500                 505                 510

Thr Ala Val Glu Ala Arg Ala Phe Val Arg Lys Phe Lys Val Ser Tyr
        515                 520                 525

Ser Leu Asn Gly Lys Asp Trp Glu Tyr Ile Gln Asp Pro Arg Thr Gln
    530                 535                 540

Gln Pro Lys Leu Phe Glu Gly Asn Met His Tyr Asp Thr Pro Asp Ile
545                 550                 555                 560

Arg Arg Phe Asp Pro Ile Pro Ala Gln Tyr Val Arg Val Tyr Pro Glu
                565                 570                 575

Arg Trp Ser Pro Ala Gly Ile Gly Met Arg Leu Glu Val Leu Gly Cys
            580                 585                 590

Asp Trp Thr Asp Ser Lys Pro Thr Val Glu Thr Leu Gly Pro Thr Val
        595                 600                 605

Lys Ser Glu Glu Thr Thr Thr Pro Tyr Pro Thr Glu Glu Ala Thr
    610                 615                 620

Glu Cys Gly Glu Asn Cys Ser Phe Glu Asp Lys Asp Leu Gln Leu
625                 630                 635                 640

Pro Ser Gly Phe Asn Cys Asn Phe Asp Phe Leu Glu Glu Pro Cys Gly
                645                 650                 655

Trp Met Tyr Asp His Ala Lys Trp Leu Arg Thr Thr Trp Ala Ser Ser
            660                 665                 670

Ser Ser Pro Asn Asp Arg Thr Phe Pro Asp Asp Arg Asn Phe Leu Arg
        675                 680                 685

Leu Gln Ser Asp Ser Gln Arg Glu Gly Gln Tyr Ala Arg Leu Ile Ser
    690                 695                 700

Pro Pro Val His Leu Pro Arg Ser Pro Val Cys Met Glu Phe Gln Tyr
705                 710                 715                 720

Gln Ala Thr Gly Gly Arg Gly Val Ala Leu Gln Val Arg Glu Ala
                725                 730                 735

Ser Gln Glu Ser Lys Leu Leu Trp Val Ile Arg Glu Asp Gln Gly Gly
            740                 745                 750

Glu Trp Lys His Gly Arg Ile Ile Leu Pro Ser Tyr Asp Met Glu Tyr
        755                 760                 765

Gln Ile Val Phe Glu Gly Val Ile Gly Lys Gly Arg Ser Gly Glu Ile
    770                 775                 780

Ala Ile Asp Asp Ile Arg Ile Ser Thr Asp Val Pro Leu Glu Asn Cys
785                 790                 795                 800

Met Glu Pro Ile Ser Ala Phe Ala Gly Glu Asn Phe Lys Val Asp Ile
                805                 810                 815

Pro Glu Ile His Glu Arg Glu Gly Tyr Glu Asp Glu Ile Asp Asp Glu
            820                 825                 830

Tyr Glu Val Asp Trp Ser Asn Ser Ser Ala Thr Ser Gly Ser Gly
        835                 840                 845

Ala Pro Ser Thr Asp Lys Glu Lys Ser Trp Leu Tyr Thr Leu Asp Pro
    850                 855                 860

Ile Leu Ile Thr Ile Ile Ala Met Ser Ser Leu Gly Val Leu Leu Gly
865                 870                 875                 880
```

```
Ala Thr Cys Ala Gly Leu Leu Leu Tyr Cys Thr Cys Ser Tyr Ser Gly
            885                 890                 895

Leu Ser Ser Arg Ser Cys Thr Thr Leu Glu Asn Tyr Asn Phe Glu Leu
            900                 905                 910

Tyr Asp Gly Leu Lys His Lys Val Lys Met Asn His Gln Lys Cys Cys
            915                 920                 925

Ser Glu Ala
    930

<210> SEQ ID NO 5
<211> LENGTH: 1972
<212> TYPE: DNA
<213> ORGANISM: human

<400> SEQUENCE: 5
atggagaggg ggctgccgct cctctgcgcc gtgctcgccc tcgtcctcgc cccggccggc      60
gcttttcgca acgataaatg tggcgatact ataaaaattg aaagccccgg gtaccttaca     120
tctcctggtt atcctcattc ttatcaccca agtgaaaaat gcgaatggct gattcaggct     180
ccggacccat accagagaat tatgatcaac ttcaaccctc acttcgattt ggaggacaga     240
gactgcaagt atgactacgt ggaagtgttc gatggagaaa atgaaaatgg acattttagg     300
ggaaagttct gtggaaagat agcccctcct cctgttgtgt cttcagggcc atttcttttt     360
atcaaatttg tctctgacta cgaaacacat ggtgcaggat tttccatacg ttatgaaatt     420
ttcaagagag gtcctgaatg ttcccagaac tacacaacac ctagtggagt gataaagtcc     480
cccggattcc ctgaaaaata tcccaacagc cttgaatgca cttatattgt ctttgcgcca     540
aagatgtcag agattatcct ggaatttgaa agctttgacc tggagcctga ctcaaatcct     600
ccagggggga tgttctgtcg ctacgaccgg ctagaaatct gggatggatt ccctgatgtt     660
ggccctcaca ttgggcgtta ctgtggacaa aaaacaccag gtcgaatccg atcctcatcg     720
ggcattctct ccatggtttt ttacaccgac agcgcgatag caaaagaagg tttctcagca     780
aactacagtg tcttgcagag cagtgtctca gaagatttca atgtatgga agctctgggc     840 atggaatcag gagaaattca ttctgaccag atcacagctt cttcccagta tagcaccaac     900
tggtctgcag agcgctcccg cctgaactac cctgagaatg ggtggactcc cggagaggat     960
tcctaccgag agtggataca gtagacttg ggccttctgc gctttgtcac ggctgtcggg    1020
acacagggcg ccatttcaaa agaaaccaag aagaaatatt atgtcaagac ttacaagatc    1080
gacgttagct ccaacgggga agactggatc accataaaag aaggaaacaa acctgttctc    1140
tttcagggaa acaccaaccc cacagatgtt gtggttgcag tattccccaa accactgata    1200
actcgatttg tccgaatcaa gcctgcaact tgggaaactg gcatatctat gagatttgaa    1260
gtatacggtt gcaagataac agattatcct tgctctggaa tgttgggtat ggtgtctgga    1320
cttatttctg actcccagat cacatcatcc aaccaagggg acagaaactg gatgcctgaa    1380
aacatccgcc tggtaaccag tcgctctggc tgggcacttc cacccgcacc tcattcctac    1440
atcaatgagt ggctccaaat agacctgggg gaggagaaga tcgtgagggg catcatcatt    1500
cagggtggga agcaccgaga gaacaaggtg ttcatgagga agttcaagat cgggtacagc    1560
aacaacggct cggactggaa gatgatcatg gatgacagca acgcaaggc gaagtctttt    1620 gagggcaaca caactatga tacacctgag ctgcggactt ttccagctct ctccacgcga    1680
ttcatcagga tctaccccga gagagccact catggcggac tggggctcag aatggagctg    1740
ctgggctgtg aagtggaagc ccctacagct ggaccgacca ctcccaacgg gaacttggtg    1800
```

-continued

```
gatgaatgtg atgacgacca ggccaactgc cacagtggaa caggtgatga cttccagctc   1860
acaggtggca ccactgtgct ggccacagaa agcccacggt catagacag caccatacaa    1920 tcaggtatca aataaaatac gaaatgtgac agaaaaaaaa aaaaaaaaaa aa            1972
```

<210> SEQ ID NO 6
<211> LENGTH: 644
<212> TYPE: PRT
<213> ORGANISM: human

<400> SEQUENCE: 6

```
Met Glu Arg Gly Leu Pro Leu Leu Cys Ala Val Leu Ala Leu Val Leu
1               5                   10                  15

Ala Pro Ala Gly Ala Phe Arg Asn Asp Lys Cys Gly Asp Thr Ile Lys
            20                  25                  30

Ile Glu Ser Pro Gly Tyr Leu Thr Ser Pro Gly Tyr Pro His Ser Tyr
        35                  40                  45

His Pro Ser Glu Lys Cys Glu Trp Leu Ile Gln Ala Pro Asp Pro Tyr
    50                  55                  60

Gln Arg Ile Met Ile Asn Phe Asn Pro His Phe Asp Leu Glu Asp Arg
65                  70                  75                  80

Asp Cys Lys Tyr Asp Tyr Val Glu Val Phe Asp Gly Glu Asn Glu Asn
                85                  90                  95

Gly His Phe Arg Gly Lys Phe Cys Gly Lys Ile Ala Pro Pro Pro Val
            100                 105                 110 al Ser Ser Gly Pro Phe Leu Phe Ile Lys Phe Val Ser Asp Tyr Glu
        115                 120                 125

Thr His Gly Ala Gly Phe Ser Ile Arg Tyr Glu Ile Phe Lys Arg Gly
    130                 135                 140

Pro Glu Cys Ser Gln Asn Tyr Thr Thr Pro Ser Gly Val Ile Lys Ser
145                 150                 155                 160

Pro Gly Phe Pro Glu Lys Tyr Pro Asn Ser Leu Glu Cys Thr Tyr Ile
                165                 170                 175

Val Phe Ala Pro Lys Met Ser Glu Ile Ile Leu Glu Phe Glu Ser Phe
            180                 185                 190

Asp Leu Glu Pro Asp Ser Asn Pro Pro Gly Gly Met Phe Cys Arg Tyr
        195                 200                 205

Asp Arg Leu Glu Ile Trp Asp Gly Phe Pro Asp Val Gly Pro His Ile
    210                 215                 220

Gly Arg Tyr Cys Gly Gln Lys Thr Pro Gly Arg Ile Arg Ser Ser Ser
225                 230                 235                 240

Gly Ile Leu Ser Met Val Phe Tyr Thr Asp Ser Ala Ile Ala Lys Glu
                245                 250                 255

Gly Phe Ser Ala Asn Tyr Ser Val Leu Gln Ser Ser Val Ser Glu Asp
            260                 265                 270

Phe Lys Cys Met Glu Ala Leu Gly Met Glu Ser Gly Glu Ile His Ser
        275                 280                 285

Asp Gln Ile Thr Ala Ser Ser Gln Tyr Ser Thr Asn Trp Ser Ala Glu
    290                 295                 300

Arg Ser Arg Leu Asn Tyr Pro Glu Asn Gly Trp Thr Pro Gly Glu Asp
305                 310                 315                 320

Ser Tyr Arg Glu Trp Ile Gln Val Asp Leu Gly Leu Leu Arg Phe Val
                325                 330                 335

Thr Ala Val Gly Thr Gln Gly Ala Ile Ser Lys Glu Thr Lys Lys Lys
```

```
                    340             345             350
Tyr Tyr Val Lys Thr Tyr Lys Ile Asp Val Ser Ser Asn Gly Glu Asp
                355             360             365

Trp Ile Thr Ile Lys Glu Gly Asn Lys Pro Val Leu Phe Gln Gly Asn
            370             375             380

Thr Asn Pro Thr Asp Val Val Ala Val Phe Pro Lys Pro Leu Ile
385             390             395             400

Thr Arg Phe Val Arg Ile Lys Pro Ala Thr Trp Glu Thr Gly Ile Ser
                405             410             415

Met Arg Phe Glu Val Tyr Gly Cys Lys Ile Thr Asp Tyr Pro Cys Ser
            420             425             430

Gly Met Leu Gly Met Val Ser Gly Leu Ile Ser Asp Ser Gln Ile Thr
            435             440             445

Ser Ser Asn Gln Gly Asp Arg Asn Trp Met Pro Glu Asn Ile Arg Leu
            450             455             460

Val Thr Ser Arg Ser Gly Trp Ala Leu Pro Ala Pro His Ser Tyr
465             470             475             480

Ile Asn Glu Trp Leu Gln Ile Asp Leu Gly Glu Glu Lys Ile Val Arg
                485             490             495

Gly Ile Ile Gln Gly Gly Lys His Arg Glu Asn Lys Val Phe Met
            500             505             510

Arg Lys Phe Lys Ile Gly Tyr Ser Asn Asn Gly Ser Asp Trp Lys Met
            515             520             525

Ile Met Asp Asp Ser Lys Arg Lys Ala Lys Ser Phe Glu Gly Asn Asn
            530             535             540

Asn Tyr Asp Thr Pro Glu Leu Arg Thr Phe Pro Ala Leu Ser Thr Arg
545             550             555             560

Phe Ile Arg Ile Tyr Pro Glu Arg Ala Thr His Gly Gly Leu Gly Leu
                565             570             575

Arg Met Glu Leu Leu Gly Cys Glu Val Glu Ala Pro Thr Ala Gly Pro
            580             585             590

Thr Thr Pro Asn Gly Asn Leu Val Asp Glu Cys Asp Asp Gln Ala
            595             600             605

Asn Cys His Ser Gly Thr Gly Asp Asp Phe Gln Leu Thr Gly Gly Thr
            610             615             620

Thr Val Leu Ala Thr Glu Lys Pro Thr Val Ile Asp Ser Thr Ile Gln
625             630             635             640

Ser Gly Ile Lys

<210> SEQ ID NO 7
<211> LENGTH: 1787
<212> TYPE: DNA
<213> ORGANISM: human

<400> SEQUENCE: 7
atggatatgt tcctctcac ctgggttttc ttagccctct acttttcaag acaccaagtg      60
agaggccaac cagacccacc gtgcggaggt cgtttgaatt ccaaagatgc tggctatatc    120
acctctcccg gttaccccca ggactacccc tccaccagaa actgcgagtg gattgtttac    180
gcccccgaac caaccagaa gattgtcctc aacttcaacc ctcactttga atcgagaag     240 cacgactgca agtatgactt tatcgagatt cgggatgggg acagtgaatc cgcagacctc    300
ctgggcaaac actgtgggaa catcgcccg cccaccatca tctcctcggg ctccatgctc    360
tacatcaagt tcacctccga ctacgcccgg caggggcag gcttctctct gcgctacgag     420
```

-continued

```
atcttcaaga caggctctga agattgctca aaaaacttca caagccccaa cgggaccatc    480
gaatctcctg ggtttcctga agtatccca cacaacttgg actgcacctt taccatcctg    540
gccaaaccca agatggagat catcctgcag ttcctgatct ttgacctgga gcatgaccct    600
ttgcaggtgg gagaggggga ctgcaagtac gattggctgg acatctggga tggcattcca    660
catgttggcc ccctgattgg caagtactgt gggaccaaaa caccctctga acttcgttca    720
tcgacgggga tcctctccct gacctttcac acggacatgg cggtggccaa ggatggcttc    780
tctgcgcgtt actacctggt ccaccaagag ccactagaga actttcagtg caatgttcct    840
ctgggcatgg agtctggccg gattgctaat gaacagatca gtgcctcatc tacctactct    900
gatgggaggt ggacccctca acaaagccgg ctccatggtg atgacaatgg ctggaccccc    960
aacttggatt ccaacaagga gtatctccag gtggacctgc gcttttaac catgctcacg   1020
gccatcgcaa cacagggagc gatttccagg gaaacacaga atggctacta cgtcaaatcc   1080
tacaagctgg aagtcagcac taatggagag gactggatgg tgtaccggca tggcaaaaac   1140
cacaaggtat ttcaagccaa caacgatgca actgaggtgg ttctgaacaa gctccacgct   1200
ccactgctga caaggtttgt tagaatccgc cctcagacct ggcactcagg tatcgccctc   1260
cggctggagc tcttcggctg ccgggtcaca gatgctccct gctccaacat gctgggatg    1320
ctctcaggcc tcattgcaga ctcccagatc tccgcctctt ccaccaggga ataccctctgg   1380
agccccagtg cagcccgcct ggtcagcagc cgctcgggct ggttccctcg aatccctcag   1440
gcccagcccg gtgaggagtg gcttcaggta gatctgggaa cacccaagac agtgaaaggt   1500
gtcatcatcc agggagcccg cggaggagac agtatcactg ctgtggaagc cagagcattt   1560
gtgcgcaagt tcaaagtctc ctacagccta acggcaagg actgggaata cattcaggac    1620
cccaggaccc agcagccaaa ggtaggctgt tcttggaggc ctctgtaacg ttaccctcaa   1680
cagggaggct aagtgtggta cagggagttg agactgatga tgtcccatct aaacagtcgt   1740
catccaactc ctgaaatcca ataaaacaaa tatcgtttga gagatta                 1787
```

<210> SEQ ID NO 8
<211> LENGTH: 555
<212> TYPE: PRT
<213> ORGANISM: human

<400> SEQUENCE: 8

```
Met Asp Met Phe Pro Leu Thr Trp Val Phe Leu Ala Leu Tyr Phe Ser
  1               5                  10                  15

Arg His Gln Val Arg Gly Gln Pro Asp Pro Cys Gly Gly Arg Leu
             20                  25                  30

Asn Ser Lys Asp Ala Gly Tyr Ile Thr Ser Pro Gly Tyr Pro Gln Asp
         35                  40                  45

Tyr Pro Ser His Gln Asn Cys Glu Trp Ile Val Tyr Ala Pro Glu Pro
     50                  55                  60

Asn Gln Lys Ile Val Leu Asn Phe Asn Pro His Phe Glu Ile Glu Lys
 65                  70                  75                  80

His Asp Cys Lys Tyr Asp Phe Ile Glu Ile Arg Asp Gly Asp Ser Glu
                 85                  90                  95

Ser Ala Asp Leu Leu Gly Lys His Cys Gly Asn Ile Ala Pro Pro Thr
            100                 105                 110

Ile Ile Ser Ser Gly Ser Met Leu Tyr Ile Lys Phe Thr Ser Asp Tyr
        115                 120                 125
```

-continued

```
Ala Arg Gln Gly Ala Gly Phe Ser Leu Arg Tyr Glu Ile Phe Lys Thr
130                 135                 140

Gly Ser Glu Asp Cys Ser Lys Asn Phe Thr Ser Pro Asn Gly Thr Ile
145                 150                 155                 160

Glu Ser Pro Gly Phe Pro Glu Lys Tyr Pro His Asn Leu Asp Cys Thr
                165                 170                 175

Phe Thr Ile Leu Ala Lys Pro Lys Met Glu Ile Ile Leu Gln Phe Leu
            180                 185                 190

Ile Phe Asp Leu Glu His Asp Pro Leu Gln Val Gly Glu Gly Asp Cys
        195                 200                 205

Lys Tyr Asp Trp Leu Asp Ile Trp Asp Gly Ile Pro His Val Gly Pro
210                 215                 220

Leu Ile Gly Lys Tyr Cys Gly Thr Lys Thr Pro Ser Glu Leu Arg Ser
225                 230                 235                 240

Ser Thr Gly Ile Leu Ser Leu Thr Phe His Thr Asp Met Ala Val Ala
                245                 250                 255

Lys Asp Gly Phe Ser Ala Arg Tyr Tyr Leu Val His Gln Glu Pro Leu
            260                 265                 270

Glu Asn Phe Gln Cys Asn Val Pro Leu Gly Met Glu Ser Gly Arg Ile
        275                 280                 285

Ala Asn Glu Gln Ile Ser Ala Ser Ser Thr Tyr Ser Asp Gly Arg Trp
290                 295                 300

Thr Pro Gln Gln Ser Arg Leu His Gly Asp Asp Asn Gly Trp Thr Pro
305                 310                 315                 320

Asn Leu Asp Ser Asn Lys Glu Tyr Leu Gln Val Asp Leu Arg Phe Leu
                325                 330                 335

Thr Met Leu Thr Ala Ile Ala Thr Gln Gly Ala Ile Ser Arg Glu Thr
            340                 345                 350

Gln Asn Gly Tyr Tyr Val Lys Ser Tyr Lys Leu Glu Val Ser Thr Asn
        355                 360                 365

Gly Glu Asp Trp Met Val Tyr Arg His Gly Lys Asn His Lys Val Phe
370                 375                 380

Gln Ala Asn Asn Asp Ala Thr Glu Val Val Leu Asn Lys Leu His Ala
385                 390                 395                 400

Pro Leu Leu Thr Arg Phe Val Arg Ile Arg Pro Gln Thr Trp His Ser
                405                 410                 415

Gly Ile Ala Leu Arg Leu Glu Leu Phe Gly Cys Arg Val Thr Asp Ala
            420                 425                 430

Pro Cys Ser Asn Met Leu Gly Met Leu Ser Gly Leu Ile Ala Asp Ser
        435                 440                 445

Gln Ile Ser Ala Ser Ser Thr Gln Glu Tyr Leu Trp Ser Pro Ser Ala
450                 455                 460

Ala Arg Leu Val Ser Ser Arg Ser Gly Trp Phe Pro Arg Ile Pro Gln
465                 470                 475                 480

Ala Gln Pro Gly Glu Glu Trp Leu Gln Val Asp Leu Gly Thr Pro Lys
                485                 490                 495

Thr Val Lys Gly Val Ile Ile Gln Gly Ala Arg Gly Gly Asp Ser Ile
            500                 505                 510

Thr Ala Val Glu Ala Arg Ala Phe Val Arg Lys Phe Lys Val Ser Tyr
        515                 520                 525

Ser Leu Asn Gly Lys Asp Trp Glu Tyr Ile Gln Asp Pro Arg Thr Gln
530                 535                 540

Gln Pro Lys Val Gly Cys Ser Trp Arg Pro Leu
```

-continued

```
545             550             555
```

<210> SEQ ID NO 9
<211> LENGTH: 18
<212> TYPE: PRT
<213> ORGANISM: human

<400> SEQUENCE: 9

Phe Arg Asn Asp Glu Cys Gly Asp Thr Ile Lys Ile Glu Asn Pro Gly
 1               5                  10                  15

Tyr Leu

<210> SEQ ID NO 10
<211> LENGTH: 18
<212> TYPE: PRT
<213> ORGANISM: human

<400> SEQUENCE: 10

Phe Arg Ser Asp Lys Cys Gly Gly Thr Ile Lys Ile Glu Ser Pro Gly
 1               5                  10                  15

Tyr Leu

<210> SEQ ID NO 11
<211> LENGTH: 24
<212> TYPE: DNA
<213> ORGANISM: human

<400> SEQUENCE: 11
tttcgcaacg ataaatgtgg cgat                                          24

<210> SEQ ID NO 12
<211> LENGTH: 20
<212> TYPE: DNA
<213> ORGANISM: human

<400> SEQUENCE: 12
tatcactcca ctaggtgttg                                               20

<210> SEQ ID NO 13
<211> LENGTH: 20
<212> TYPE: DNA
<213> ORGANISM: human

<400> SEQUENCE: 13
ccaaccagaa gattgtcctc                                               20

<210> SEQ ID NO 14
<211> LENGTH: 20
<212> TYPE: DNA
<213> ORGANISM: human

<400> SEQUENCE: 14
gtaggtagat gaggcactga                                               20

<210> SEQ ID NO 15
<211> LENGTH: 44
<212> TYPE: PRT
<213> ORGANISM: human

<400> SEQUENCE: 15

Pro Cys Gly Pro Cys Ser Glu Arg Arg Lys His Leu Phe Val Gln Asp
 1               5                  10                  15

```
Pro Gln Thr Cys Lys Cys Ser Cys Lys Asn Thr Asp Ser Arg Cys Lys
            20                  25                  30

Ala Arg Gln Leu Glu Leu Asn Glu Arg Thr Cys Arg
        35                  40
```

```
<210> SEQ ID NO 16
<211> LENGTH: 21
<212> TYPE: DNA
<213> ORGANISM: human

<400> SEQUENCE: 16
gaagtatacg gttgcaagat a                                          21

<210> SEQ ID NO 17
<211> LENGTH: 21
<212> TYPE: DNA
<213> ORGANISM: human

<400> SEQUENCE: 17
gcgttcctct cggatccagg c                                          21

<210> SEQ ID NO 18
<211> LENGTH: 19
<212> TYPE: DNA
<213> ORGANISM: human

<400> SEQUENCE: 18
caggtatcaa ataaaatac                                             19

<210> SEQ ID NO 19
<211> LENGTH: 16
<212> TYPE: PRT
<213> ORGANISM: human

<400> SEQUENCE: 19

His His His His His His Gln Gln Lys Leu Ile Ser Gln Gln Asn Leu
  1               5                  10                  15

<210> SEQ ID NO 20
<211> LENGTH: 20
<212> TYPE: DNA
<213> ORGANISM: human

<400> SEQUENCE: 20
ggctgccggg taacagatgc                                            20

<210> SEQ ID NO 21
<211> LENGTH: 18
<212> TYPE: DNA
<213> ORGANISM: human

<400> SEQUENCE: 21
atggatatgt ttcctctc                                              18

<210> SEQ ID NO 22
<211> LENGTH: 20
<212> TYPE: DNA
<213> ORGANISM: human

<400> SEQUENCE: 22
gttcttggag gcctctgtaa                                            20

<210> SEQ ID NO 23
```

-continued

```
<211> LENGTH: 27
<212> TYPE: DNA
<213> ORGANISM: human

<400> SEQUENCE: 23
ggaattccat atggttttaa ctgtgaa                                        27

<210> SEQ ID NO 24
<211> LENGTH: 47
<212> TYPE: DNA
<213> ORGANISM: human

<400> SEQUENCE: 24
gctctagatt aatgatgatg atgatgatgg gtcttcaaca cattgcc                  47
```